US007612255B2

(12) United States Patent
Gressel et al.

(10) Patent No.: US 7,612,255 B2
(45) Date of Patent: Nov. 3, 2009

(54) TRANSGENIC PLANTS FOR MITIGATING INTROGRESSION OF GENETICALLY ENGINEERED GENETIC TRAITS

(76) Inventors: Jonathan Gressel, 15 Hayarden Street, 76604 Rehovot (IL); Hani Al-Ahmad, Al-Makhfiah, Main Street, Nablus, West Bank, Palestinian Authority (IL)

( * ) Notice: Subject to any disclaimer, the term of this patent is extended or adjusted under 35 U.S.C. 154(b) by 73 days.

(21) Appl. No.: 10/774,388

(22) Filed: Feb. 10, 2004

(65) Prior Publication Data

US 2004/0172678 A1    Sep. 2, 2004

Related U.S. Application Data

(63) Continuation-in-part of application No. 09/889,737, filed as application No. PCT/IL00/00046 on Jan. 24, 2000, now abandoned.

(30) Foreign Application Priority Data

Feb. 3, 1999    (IL) ..................................... 128353

(51) Int. Cl.
*C12N 15/82*    (2006.01)
*A01H 1/00*    (2006.01)
(52) U.S. Cl. .................. 800/290; 800/269; 800/279; 800/289; 800/300; 800/302; 800/306; 800/317.3; 800/320.2
(58) Field of Classification Search .................. None
See application file for complete search history.

(56) References Cited

U.S. PATENT DOCUMENTS

| 5,451,514 A | * | 9/1995 | Boudet et al. ............... 800/286 |
| 5,512,466 A | | 4/1996 | Klee et al. |
| 5,723,765 A | | 3/1998 | Oliver et al. |
| 5,731,180 A | * | 3/1998 | Dietrich ...................... 800/278 |
| 5,948,956 A | * | 9/1999 | Lee et al. .................... 800/320 |
| 6,114,603 A | * | 9/2000 | Christou et al. ............. 800/293 |
| 6,198,024 B1 | | 3/2001 | Yanofsky et al. |

FOREIGN PATENT DOCUMENTS

| WO | WO 96/34088 | | 10/1996 |
| WO | WO 97/29123 | * | 8/1997 |
| WO | WO 97/30162 | * | 8/1997 |
| WO | WO 97/42326 | * | 11/1997 |

OTHER PUBLICATIONS

Reichman et al. Molecular Ecology 15(13): 4243-4255 (Nov. 2006; Abstract only).*
Colliver et al. Plant Molecular Biology 35: 509-522 (1997).*
Goldman et al. Crop Science 34: 908-915 (1994).*
Dasgupta et al. "Co-Ordinated Expression of Multiple Enzymes in Different Subcellular Compartments in Plants", The Plant Journal, 16(1): 107-116, 1998.
Azpiroz et al. "An Arabidopsis Brassinosteriod-Dependent Mutant Is Blocked in Cell Elongation", The Plant Cell, 10: 219-230, 1998.
Al-Kaff et al. "Transcriptional and Posttranscriptional Plant Gene Silencing in Response to A Pathogen", Science, 279: 2113-2115, 1998.
Schaller et al. "Overexpression of an Arabidopsis cDNA Encoding A Sterol-C24(1)-Methyltransferase in Tobacco Modifies the Ratio of 24-Methyl Cholesterol to Sitosterol and Is Associated With Growth Reduction", Plant Physiology, 118: 461-469, 1998.
Zemetra et al. "Potential for Gene Transfer Between Wheat (*Triticum aestivum*) and Jointed Goatgrass (*Aegilops cylindrica*)", Weed Science, 46: 313-317, 1998.
Koltunow et al. "Apomixis: Molecular Strategies for the Generation of Genetically Identical Seeds Without Fertilization", Plant Physiology, 108: 1345-1352, 1995.
Young "Heritability of Resistance to Seed Shattering in Kleingrass", Crop Science, 31: 1156-1158, 1991.
Williams "Genetic Engineering for Pollution Control", Trends in Biotechnology, 13: 344-349, 1995.
Crawley et al.. "Ecology of Trangenic Oilseed Rape in Natural Habitats", Nature, 363: 620-623, 1993.
Snow et al. "Fecundity, Phenology, and Seed Dormancy of F1 Wild-Crop Hybrids in Sunflower (*Helianthus annuus*, Asteracae)", American Journal of Botany, 85(6): 794-801, 1998.
Jorgensen et al. "Spontaneous Hybridization Between Oilseed Rape (*Brassica napus*) and Weedy B. Campestris (*Brassicaceae*): A Risk of Growing Genetically Modified Oilseed Rape", American Journal of Botany, 81(12): 1620-1626, 1994.
Paterson et al. "The Weediness of Wild Plants: Molecular Analysis of Genes Influencing Dispersal and Persistence of Johnsongrass, Sorghum Halepense (L.) Pers.", Proc. Natl. Acad. Sci. USA, 92: 6127-6131, 1995.
Vleeshouwers "The Effect of Seed Dormancy on Percentage and Rate of Germination in Polygonum Persicaria, and Its Relevance for Crop-Weed Interaction", Annual of Applied Biology, 132: 289-299, 1998.
Eijlander et al. "Biological Containment of Potato (*Solanum tuberosum*): Outcrossing to the Related Wild Species Black Nightshade (*Solanum nigrum*) and Bittersweet (*Solanum dulcamara*)", Sexual Plant Reproduction, 7: 29-40, 1994. Abstract. [Chem. Abstr., 75(20): 163, Col. 1, Abstract No. 120718k].
Ritala et al. "Measuring Gene Flow in the Cultivation of Transgenic Barley", Crop Science, 42: 278-285, 2002.
Kuvshinov et al. "Molecular Control of Transgene Escape From Genetically Modified Plants", Plant Science, 160(3): 517-522, 2001. Abstract.
Gressel "Tandem Constructs to Mitigate Transgene Flow", Draft Journal Art., 2003.

(Continued)

*Primary Examiner*—David T Fox
(74) *Attorney, Agent, or Firm*—Dodds & Associates; John Dodds; Susanne Somersalo

(57) ABSTRACT

Genetic mechanisms for mitigating the effects of introgression of a genetically engineered genetic trait of a cultivated crop to an undesirable, interbreeding related species.

11 Claims, 7 Drawing Sheets

OTHER PUBLICATIONS

Daniell et al. "Containment of Herbicide Resistance Through Genetic Engineering of the Chloroplast Genome", Nature Biotechnology, 16: 345, 1998.

Oard et al. "Field Evaluation of Seed Production, Shattering, and Dormancy in Hybrid Populations of Transgenic Rice (*Oryra sativa*) and the Weed, Red Rice (*Oryza sativa*)", Plant Science, 157: 13-22, 2000.

Linder "Potential Persistence of Transgenes: Seed Performance of Transgenic Canola and Wild X Canola Hybrids", Ecological Applications, 8(4): 1180-1195, 1998.

Landbo et al. "Seed Germination in Weedy *Brassica campestris* and Its Hybrids With B. Napus: Implications for Risk Assessment of Transgenic Oilseed Rape", Euphytica, 97: 209-216, 1997.

Desplanque et al. "Transgenic Weed Beets: Possible, Probable, Avoidable?", Journal of Applied Ecology, 39: 561-571, 2002.

Wang et al. "Constitutive Expression of the Circadian Clock Associated 1 (CCA1) Gene Disrupts Circadian Rhythms and Suppresses Its Own Expression", Cell, 93: 1207-1217, 1998.

Bartsch et al. "Boisafety of Hybrids Between Transgenic Virus-Resistant Sugar Beet and Swiss Chard", Ecological Appl., 11(1): 142-147, 2001.

Kuvshinov et al. "Barnase Gene Inserted in the Intron of Gus—A Model for Controlling Transgene Flow in Host Plants", Plant Science, 167: 173-182, 2004.

Gressel et al. "Genetic and Ecological Risks From Biotechnologically-Derived Herbicide-Resistant Crops: Decision Trees for Risk Assessment", Plant Breeding Reviews, 18(Chap.5): 251-303, 2000.

Gressel et al. "Containment and Mitigation of Transgene Flow From Crops", The BCPC International Congress—Crop Science & Technology, p. 1175-1180, 2003.

Gressel "Tandem Constructs: Preventing the Rise of Superweeds", Tibtech, 17: 361-366, 1999.

Gressel "Introgressional Failsafes for Transgenic Crops", Xieme Colloque International sur la Biologie des Mauvais Herbes, 8 p. 2000.

Gressel "Potential Failsafe Mechanisms Against the Spread and Introgression of Transgenic Hypervirulent Biocontrol Fungi", Trends in Biotechnology, 19(4): 149-154, 2001.

Al-Ahmad et al. "Tandem Constructs to Mitigate Transgene Persistence: Tobacco as A Model", Molecular Ecology, 13: 697-710, 2004.

* cited by examiner

SCHEMATIC 1: TRANSGENIC MITIGATION

GC = primary gene of choice; TM = transgenic mitigator gene

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
gctttacact ttatgcttcc                                               20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
taacactttt tctttttttg                                               20

<210> SEQ ID NO 3
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 3
ggttatgatg gcaggatgtg g                                             21

<210> SEQ ID NO 4
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 4
cgttacatca ttttctcaca a                                             21

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
```

```
tagaagtggt agtggagtga                                               20

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
cgacggagag agacggtaaa                                               20

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
tcatttcatt tggagaggac                                               20

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
catgatattc ggcaagcagg                                               20

<210> SEQ ID NO 9
<211> LENGTH: 3549
<212> TYPE: DNA
<213> ORGANISM: Brassica napus

<400> SEQUENCE: 9
attatacagt tgaaatcaac cctaaaatcc caaatttgga gttcaaagtt ttttatttg      60 tttgaattac aatctcagct gattgatttt ttagtgacca atcatttga tatatttatt     120 taattttgcc tctcttgatc tgcaaaaata tttgatcata aacttgaata gcatcgctct    180
ctagttcaat atctctccca cttctttttcg gtggtttatt catttggtga cgatatcaca   240
gaagcaatgg atgaaggtgg gagtagtcac gatgcagaga gtagcaagaa gataggtaga    300
gggaagatag agataaagag gatagagaac acaacaaatc gtcaagtaac cttctgcaaa    360
cgacgcaatg gtcttctcaa gaaagcttat gagctctctg tcttgtgtga tgctgaagtt    420
gccctcgtta tcttctccac tcgtggcctt ctttatgagt acgccagcaa caggtatgct    480
tctcctaccc acaccttgat ctagcttct tgattaattt actactacaa tcctagttaa    540
tatgagccaa gattagggtt tgtttaaat tacaatcctg aattttctat tttttatata     600
aaaattagat ctcaataggg ctaccattgt ctctctagat ctgtgtatat ccaaataatg    660
aagacggaag aaagctgtct tgtcttctca acttctcgtt agtctgatct tgttagtttt    720 cactctttttt ctgcagatca ctagaacctg tttcatgtca tgtcagcttc tataaaatgc   780
ttttatcttg acgacccata ctatgtcttt ctttaaatat tattagggtt tcgtcagtaa    840
aaaaaaactg ggtagtacgc aatagcatgc atatatgtaa atatgcaaga cttatgtaac    900
cctcctgtct tgtgaaactt gggacatagc ctaatgatgg ttgtcactat gacactatgg    960
atccccttta atttttttcc taacccaaga aaacaaatgc cgaccgataa aactttagtt    1020
```

```
atatataaaa tatataacat ctatctggag ttcgtatgtt gagaatatat atatgtgact   1080
atttaaaatc taggcccttt aaggatgtaa aatatgtgta ttccattaat atattaatga   1140
gagggagata actcagagag aagtgtctga aatcaaagtg gtacgagcca atgggaatct   1200
atagcactct gagctccatt tatatgtgct gttgtatttg aaaaaaaaca gttaatcatc   1260
cttaaagcat actttgatga cattaaacca tataatatgc atggaccttg ttctgtattc   1320
ctcctcaaac cgtaagtaat taccagtttg aatccatata ttaattaatt gctgcatcag   1380
ccattttaa atatgtacat tgaaaaagta gtttactcga gcacaatgtg tgtcattgaa    1440
gtttctcctc gtagtggtca aaaaactggt ccaaacctca aagccatcac attccttgtc   1500
gattttaagg ttttgccccc aaaataaaca ttccaaaacc ttaatcaaga aatgtcgtcc   1560
caattatctc tgttttaaga gtatattaat taaattaaat ataatggttt ctttaacttt   1620
ctagtgtgaa gggtacaatt gaaaggtaca agaaagcttg ttccgatgcc gttaaccctc   1680
ctactgtcac tgaagctaat accaaggtac cattcttgta tagttttttt tttactagcc   1740
ctctcttttt tcttattttt atgatcaatt attaacgttt agaaagtgaa atctttttaa   1800
aatgtgtata tatatgtggt ttcttgtttc tatgatgatc aattatgtat tcgtgtcaaa   1860
agaacattac taacaaaatt cttaacattt acacccaaaa gtaaaaacat tattaacaaa   1920
aagagtggat tcctgaaatg cattgagacg gttgtatttg tatgcatgga accttcagc   1980
actatcagca agaagcctct aagcttcgga ggcagattcg ggacattcag aattcgaaca   2040
ggtaagtaac tatagctctt ctgaggtttc ttgttttgat cactactttc ctattatata   2100
gctgatcatt tcgattagtt taactgaaaa aattacagaa cctgagtcac gtaagttata   2160
attcattcaa aatcgttcat tccaaataat ttttttttctt ttttggtagg attgttaggt   2220
tggttaactt acttggaatt gcttgaatct ctgcttggtt ttgtgatata tggtatatgg   2280
aaccataaat aaaaacttgg gtttaatttt cgtgtttttt tgccaaatag tttacttta    2340
gttacgtttg aacgagtgca aatgtttatt aatgttcatg tttatgaatt gaaggcatat   2400
tgttggagaa tcacttggtt cattgaactt caaggaactc aaaaacctag aaggacggct   2460
tgaaaaagga atcagccgcg tccgatccaa gaaggtacgt actgataaac ctatacgtct   2520
atgtctctct atagtttata tatagtttcc tcgctcttat atgaatcttt tccagagtga   2580
acttttagtg gcagagatag agtatatgca gaagagggta agtaacgttt cttcccaatc   2640
tttcatcgtt cttttacatg ggttttgagt tttgccataa accatgtagg aaatggagtt   2700
gcagcacgtt aacatgtacc taagagctaa ggttagtcac gtcttcatcc tctaaccgag   2760
ataatgaacg tgtatcacaa ccaaactttg atgttcggtt tgtgcagata gaacaaggcg   2820
cgagattgaa tccggaacaa catggatccg gtgtaataca agggacggcg tttatgagt    2880
ccggtctgtc ttcttctcat gatcagtcgc agcattataa ccggaattat attccggtta   2940
accttcttga accgaatcaa caattctccg gtcaagacca acctcctctt caacttgttt   3000
aagcttaatc atgattaaaa cttctttctc ccctccccc ctccaaacgt ttttcagaga    3060
gagacaaaga gtaaattaca tttatgcgac attcttattc atagttaagg ttccaataat   3120
gataaaaaca aaaatcttgt tcctattaca aaaataaaac ttacaaacat ttattatgtc   3180
atgaatatta tgatatgtag ctataattaa acaataatac attattttag taagctactt   3240
gggataataa tgaaaaaaca agctacatat tcataaaatc tagattactc ttcagtatat   3300
agacatgaga gaaccatgaa gcagaggctg aaggctaaac cttcttccct ccgttctctc   3360
```

```
-continued atacagattt gctaactttt tcttttatct tcttttcatc agttcatgat tttacatttt    3420
ctaacgaaga tgtttgatga atttacgtat ctataccagt aagatcttac cttagggtta    3480
ctaatctcta gccacggttt tgctggaccg ctaaaatgta gaaccgcagc agatttcaga    3540
atctcttca                                                            3549
```

TRANSGENIC PLANTS FOR MITIGATING INTROGRESSION OF GENETICALLY ENGINEERED GENETIC TRAITS

This is a continuation-in-part of U.S. patent application Ser. No. 09/889,737, filed Jul. 20, 2001, now abandoned, which is a U.S. National Phase application of PCT/IL00/00046, filed 24 Jan. 2000, which claims priority from Israeli Patent Application No. 128353, filed 3 Feb. 1999.

FIELD AND BACKGROUND OF THE INVENTION

The present invention relates to a genetic mechanism for mitigating the effects of introgression of a genetically engineered genetic trait of a crop to a weed and of mitigating a weedy potential of the crop and, more particularly, to a genetic mechanism for mitigating the effects of introgression of genetically engineered resistances of crops to weeds.

Crop domestication and weeds: During the prehistoric and historic processes of domestication of crops, farmers selected against a large number of traits that were valuable for wild species, but undesirable in agronomic practice. These differences between wild species and crops were further accentuated by selective breeding, and even more so by genetic engineering, which allowed introducing traits that were non-existent in the gene pool of the species, genus, family, or kingdom of the crop.

Concurrently with domestication, a few wild species evolved to fill the new ecological niches, the disturbed eco-systems known as farmers' fields (Baker, 1974; Holt, 1988; Turner, 1988). Only a few hundred of the tens of thousands of wild species have followed this evolutionary pathway from wild plant to widespread agricultural weed (Holm et al., 1997). Thus, even though some weeds are closely related to crops or are even of the same species as the crops, they vary in a number of traits that distinguish them from wild species, as well as from the crop. These evolutionary processes are not static; indeed they are quite dynamic even on a human generation timescale (Baker, 1991). Changes in agricultural practices (drainage, fertilizer use, tillage and herbicide use) caused some pernicious weeds to return to being wild species, and some wild species to become weeds (Haas and Streibig, 1982). Crops can become "volunteer" weeds in the following crop, or even feral, and re-evolve some weedy traits. Some weeds have even introgressed new traits from conventionally-bred crops (wild barleys in barley have introgressed many new traits; wild sunflowers from sunflowers (Snow et al., 1998). Worse, crops have introgressed weedy traits from related weeds e.g., poor oil quality in canola (Diepenbrock and Leon, 1988), and early bolting in sugar beets from weedy beets (Boudry et al., 1998). These dynamic evolutionary events all occurred before the advent of transgenics.

Crops often possess conventionally-bred traits that would be advantageous to the weeds growing in their midst. Horizontal gene transfer (introgression to totally unrelated species) occurs only rarely to other species within a genus, and even more rarely to species in closely related genera. Thus, even vital traits for weeds such as herbicide resistance have never passed horizontally from non transgenics (Torgersen, 1996), for example from wheat to grass weeds all in the family Poaceae. This lack of horizontal transfer allows the control of these related weeds in the crop. The weeds have had to evolve herbicide resistance from within their own genomes, and not by horizontal gene transfer.

Introgression of genetically engineered traits: The genetic distances between crop and weed were slightly enhanced with the advent of genetic engineering. Traits could be artificially forced horizontally into the crops to enhance cost-effectiveness of agriculture (higher yields, new products, resistances to insects, diseases, and to herbicides). Detractors of both the process of genetic engineering and its products have raised the possibilities that the engineered crops would become uncontrollable weeds, or that the genes would introgress into related weeds, rendering them "weedier", or into wild species, turning them into weeds (Kloppenburg, 1988; Goldberg et al., 1990; Risler and Mellon, 1993). Hyper-generalizations were raised and terminology such as "superweeds" was coined (Kling, 1996). Calls were issued to prohibit or abandon all transgenic crops because of the possibilities of introgression of such traits into some weeds (Risler and Mellon, 1993). The fact that most crops have no interbreeding relatives in much of the world (Keeler et al., 1996) did not allay the fears of detractors of genetically modified crops. The issues aired in the popular press with extreme statements such as "The greatest danger of genetic engineering of plants may come from sex with weeds". The debate surrounding introgression of genetically engineered traits has become as sterile as most of the interspecific hybrids generated using highly unnatural lab tricks to save the $F_1$ hybrids (Darmency, 1994).

However, farmers and foresters in most of the world have begun to realize the benefits that accrue from cultivating transgenic crops and forest trees, whether to prevent soil erosion by using post-emergence herbicides or use less expensive/toxic insecticides while contributing to farmer and environmental health and safety. It has been estimated that as much as 60-70% of basic industrial crops (soybean, corn, rapeseed and cotton) used in the US is produced from genetically modified crops (Genetically Engineered Organism-Public Issues Education Project—www.geo-pie.cornell.edu). Additionally, many other traits have been transformed into crops that provide an added value to the crops. Examples of a number of crops, transformed with genes of choice, which have been tested at the field level in the USA, are presented in Table 1.

TABLE 1

Primary traits being engineered into major crops field tested in the USA requiring containment and mitigation.

| Crop[a] | Primary genes[a] | Main introgressional problems |
|---|---|---|
| Oilseed rape | pharmaceuticals | *Brassica* weeds, |
|  | herbicide resistance | other oilseed rape, |
|  |  | volunteer problems |
|  | disease resistance |  |
|  | insect resistance |  |
|  | improved quality |  |
| Sugar beet | herbicide resistance | Feral and wild beets |
| (Carrot/root | disease resistance | (wild carrot) |
| crops) | insect resistance |  |
| Turf grass | herbicide resistance | related weeds |
|  | disease resistance | anti-GMO neighbors |
|  | insect resistance |  |
| Corn | herbicide resistance |  |
|  | disease resistance |  |
|  | insect resistance |  |
|  | agronomic properties |  |
|  | nutritional quality |  |
|  | polymers |  |
|  | pharmaceuticals |  |
| Rice | herbicide resistance | red (feral) rice |
|  | disease resistance |  |
|  | insect resistance |  |
|  | pharmaceuticals |  |

TABLE 1-continued

Primary traits being engineered into major crops field tested
in the USA requiring containment and mitigation.

| Crop[a] | Primary genes[a] | Main introgressional problems |
|---|---|---|
| Poplar (Pine) | herbicide resistance disease resistance insect resistance decreased lignin increase cellulose | native poplars (native pines) |

[a]Source: USDA-APHIS website.

Herbicide resistant crops are especially useful for controlling crop-related weeds where there had been no herbicide selectivity. Several crops (e.g., wheat, barley, sorghum, rice, squash, sunflower, sugarbeets, oats, and oilseed rape) can naturally interbreed with closely related weedy relatives under field conditions, in both directions (Gressel, J. 2002: Molecular biology of weed control Taylor and Francis, London; Ellstrand, N. C., Prentice, H. C. & Hancock, J. F. 1999: Gene flow and introgression from domestic plants into their wild relatives. Ann. Rev. Ecol. System. 30: 539-563). There is a concern that transgenes may escape from engineered crops into non-transgenic fields of the same crop, or related weedy or wild species, by hybridization and establish themselves by subsequent backcrossing. This concern has been fueled by the growing number of reports of unintentional, or "accidental" leakage of engineered traits into wild type or weedy crops (Kwon and Sim, Weed Biol and Manag, 2001;1:pg 42; and Hall, et al, Weed Sci 2000; 48:688-94). This could potentially result in large, poorly controlled populations of hybrids and their progeny with enhanced invasiveness or weediness (Ellstrand, N. C., Prentice, H. C. & Hancock, J. F. 1999: Gene flow and introgression from domestic plants into their wild relatives. Ann. Rev. Ecol. System. 30: 539-563; Steward, C. N. Jr., Halfhill, M. D. & Warwick, S. I. 2003. Transgene introgression from genetically modified crops to their wild relatives. Nature Reviews Genetics4:806-817). Many of the engineered genes such as those conferring resistance to herbicides, diseases, and to stresses may grant a fitness advantage to a weedy or wild species. Another increasingly important issue is the concern surrounding transgene flow from crops such as maize bearing transgenes encoding pharmaceuticals to other varieties. Engineered pharmaceuticals, especially vaccines, enzymes and antibodies, can be produced inexpensively in plants, without the need for animal tissue culture cells grown in a medium of expensive serum albumin that is all too easily contaminated with pathogenic mycoplasms, prions and viruses (see, for example, U.S. Pat. No. 6,262,561 to Stewart Jr, et al; U.S. Pat. No. 6,303,341 to Hiatt, et al.; and U.S. Pat. No. 6,395,964 to Arntzen et al, all encorporated herein by reference). Still, there is understandable concern over the introgression of these pharmaceutical transgenes into other varieties of the crop.

Risk analysis and risk mitigation: Tomes have been written on how to assess the risks of introgression—some with continuing generalizations and some discussing how and why this assessment must be undertaken on a case by case basis (Regal, 1994; Keeler et al., 1996; Kareiva et al., 1996; de Kathen, 1998; Williamson, 1993; Timmons et al., 1996; Kjellsson et al., 1998; Sindel, 1997; Gressel and Rotteveel, 2000, Galun and Breman, 1997; Krimsky and Wrubel, 1996). Two general approaches deal with the problems of transgene flow: containment of the transgenes within the transgenic crop, and transgenic mitigation of the effects of the primary transgenic trait should it escape and move to an undesired target. Many containment efforts have depended upon inefficient traditional means such as isolation distances (isolation zones) (see Ritala A., et al, Crop Sci 2002;42:278-85) and barrier crops (see Physical Gene Flow Barriers, page 61; in: Environmental issue report, No. 28, European Environmental Agency Publication No. 28, 2002), less conventional, but still problematic biological means such as apomixis, cleistogamy, male sterility and plastid transformation (see Biological Gene Flow Barriers, pages 60 and 61; in: Environmental issue report, No. 28, European Environmental Agency Publication No. 28, 2002, and Daniell H, Nature Biotechnology, 2002; 20:581-86) and the highly complex and uneconomical introduction of lethal traits under control of inducible promoters (see Kuvshinov VV et al, Plant Sci 200; 160:517-522, and U.S. Pat. No. 5,723,765 to Oliver et al). While most containment mechanisms will severely restrict gene flow, some gene flow (leakage) is inevitable and could then spread through the population of undesired species, unless mitigated. Thus, both containment and mitigation strategies are required for efficient and safe use of transgenic crops. Unfortunately, discussions of the hazards and risk assessment have not considered how biotechnologies can be used to mitigate the risk of introgression. No-one, including the governmental panels responsible for authorizing the cultivation of transgenic crops (Anonymous, 1994a, b;, 1997) or those interested in regulatory aspects (Be et al., 1996; Waters, 1996) has seemed to consider the prevention of weeds from using any traits that may introgress from crops, even in the few instances where one can quite surely predict that introgression eventually will occur.

Containing transgene flow—advantages and limitations: Several molecular mechanisms have been suggested to contain transgenes within a genetically modified crop (i.e. to prevent outflow to related species), or to mitigate the effects of transgene flow once it has already occurred (Gressel, 1999, 2002; Daniell, 2002; Steward et al., 2003; Gressel and Al-Almad, 2003). The containment mechanisms include utilization of partial genome incompatibility with crops such as wheat and oilseed rape having multiple genomes derived from different progenitors. When only one of these genomes is compatible for interspecific hybridization with weeds, the risk of introgression could be reduced if the transgene was inserted into the unshared genome where there is presumed to be no homologous introgression between the non-homologous chromosomes. Although it has not yet been reported whether the method of partial genome incompatibility works in wheat, it has been deemed ineffectual for oilseed rape and other similar crops (Tomiuk, J., Hauser, T. P. & Bagger-Jørgensen, R. 2000: A- or C-chromosomes, does it matter for the transfer of transgenes from *Brassica napus*. Theor. Appl. Genet. 100: 750-754), due to considerable recombination between the A and C genomes.

Another containment strategy is the integration of the transgene into the plastid or mitochondrial genomes (U.S. patent application Ser. No. 20020073443 to Heifetz et al, and Maliga, 2002, and U.S. Pat. Nos. 5,530,191, 5,451,513, 5,932,479, 5,693,507, 6,297,054, 6,376,744, 6,388,168, 6,642,053). The opportunity of gene outflow is limited due to maternal inheritance of these genomes. However, this technology does not prevent the weed from pollinating the crop, and then acting as the recurrent pollen parent. The claim of no paternal inheritance of plastome-encoded traits (Bock, R. 2001: Transgenic plastids in basic research and plant biotechnology. J. Mol. Biol. 312: 425-438; Daniell, H. 2002: Molecular strategies for gene containment in transgenic crops. Nature Biotech. 20: 581-586), has not been substantiated by those authors. Indeed, tobacco (Avni, A. & Edelman, M. 1991: Direct selection for paternal inheritance of chloroplasts in sexual progeny of *Nicotiana*. Mol. Gen. Genet. 225: 273-277) and other species (Darmency, H. 1994: Genetics of herbicide resistance in weeds and crops, In: Herbicide Resistance in Plants: Biology and Biochemistry, eds. Powles and Holtum, Lewis, Boca-Raton: 263-298) often have between a $10^{-3}$-$10^{-4}$ frequency of pollen transfer of plastid inherited traits in the laboratory. Pollen transmission of plastome traits can only be easily detected using both large samples and selectable genetic markers. A large-scale field experiment utilized a *Setaria italica* (foxtail or birdseed millet) with chloroplast-inherited atrazine resistance (bearing a nuclear dominant red leaf base marker) crossed with five different male sterile yellow- or green-leafed herbicide susceptible lines. Chloroplast-inherited resistance was pollen transmitted at a $3\times10^{-4}$ frequency in >780,000 hybrid offspring. At this transmission frequency, the probability of herbicide resistance from plastomic gene flow is orders of magnitude greater than by spontaneous nuclear genome mutations. Chloroplast transformation is probably unacceptable for preventing transgene outflow, unless stacked with additional mechanisms. For many species, such as pine, the strategy of mitigation via plastome integration is made further improbable due to complete pollen transmission of plastomic traits.

A novel additional combination that considerably lowers the risk of plastome gene outflow within a field (but not gene influx from related strains or species) can come from utilizing male sterility with transplastomic traits [Wang, T., Li, Y., Shi, Y., Reboud, X., Darmency, H. & Gressel, J. 2004: Low frequency transmission of a plastid encoded trait in *Setaria italica*. Theor. Appl. Genet. 108:315-320]. Introducing plastome-inherited traits into varieties with complete male sterility would vastly reduce the risk of transgene flow, except in the small isolated areas required for line maintenance (see, for example, U.S. Pat. No. 6,372,960 to Michiels et al). Such a double failsafe containment method might be considered sufficient where there are highly stringent requirements for preventing gene outflow to other varieties (e.g. to organically cultivated ones), or where pharmaceutical or industrial traits are engineered into a species. Plastome-encoded transgenes for non-selectable traits (e.g. for pharmaceutical production) could be transformed into the chloroplasts together with a trait such as tentoxin or atrazine resistance as a selectable plastome marker. With such mechanisms to further reduce out-crossing risk, plastome transformation can possibly meet the initial expectations.

Other molecular approaches suggested for crop transgene containment include: seed sterility, utilizing the genetic use restriction technologies (GURT) (U.S. Pat. No. 5,723,765 to Oliver, M. J., et al.), and recoverable block of function (Kuvshinov, V., et al 2001: Molecular control of transgene escape from genetically modified plants. Plant Sci. 160: 517-522). Such proposed technologies control out-crossing and volunteer seed dispersal, but theoretically if the controlling element of the transgene is silenced, expression will occur. Another approach includes the insertion of the transgene under the control of a chemically-induced promoter, so that it will be expressed upon chemical induction (U.S. Pat. No. 6,380,463 to Jepson). However, there remains the distinct possibility of an inducible promoter mutating to become constitutive.

Schernthaner et al (Proc. Natl. Acad. Sci. USA, 2003; 100: 6855-6859) proposed an impractical technology using a "repressible seed-lethal system". In order to achieve containment, the seed-lethal trait and its repressor must be simultaneously inserted at the same locus on homologous chromosomes in the hybrid the farmer sows to prevent recombination (crossing over), a technology that is not yet workable in plants. The hemizygote transgenic seed lethal parent cannot reproduce by itself, as its seeds are not viable. If the hybrid could be made, half the progeny would not carry the seed-lethal trait (or the trait of interest linked to it) and they would have to be culled, which would not be easy without a marker gene. The results of selfing or cross pollination within the crop and leading to volunteer weeds where 100% containment is needed, would leave only 25% dead and 50% like the hybrid parents and 25% with just the repressor. Thus, the repressor can cross from the volunteers to related weeds as can the trait of choice linked with the lethal, and viable hybrid weeds could form (see U.S. Pat. Pub. No. 200200669425 to Fabijanski et al.). The death of some seed in all future weed generations is inconsequential to weeds that copiously produce seed, as long as the transgenic trait provides some selective advantage.

None of the above containment mechanisms is absolute, but risk can be reduced by stacking containment mechanisms together, compounding the infrequency of gene introgression, possibly stacking a containment that precludes pollination to related species with one that precludes pollination by related species. Still, even at very low frequencies of gene transfer, once such "leakage" occurs, the new bearer of the transgene can disperse throughout the population, if even just a small fitness advantage is conferred to the progeny.

As further detailed hereinunder, a case by case analysis of where intra or interspecific introgressions between genetically engineered crops and weeds are possible shows that there are specific genetic strategies conceivable for mitigation of interspecific introgression.

There is thus a widely recognized need for, and it would be highly advantageous to have, failsafe anti-introgression and introgression-mitigating mechanisms to reduce the possibility of intra and interspecific introgression between genetically engineered crops and weeds.

SUMMARY OF THE INVENTION

According to one aspect of the present invention there is provided a method of obtaining a cultivated crop capable of mitigating the effects of introgression of at least one genetically engineered, commercially desirable genetic trait to an undesirable interbreeding species related to the cultivated crop, the method comprising transforming a population of plants of the cultivated crop to co-express at least one male-sterility gene, thereby producing apomictic seeds of said cultivated crop of a type which give rise to male sterile crop plants, thereby obtaining a cultivated crop capable of mitigating the effects of introgression of said genetically engineered, commercially desirable genetic trait of the cultivated crop to said undesirable interbreeding species related thereto.

According to a further aspect of the present invention there is provided a method of obtaining a cultivated crop having multiple genomes derived from different wild sources capable of mitigating the effects of introgression of at least one genetically engineered, commercially desirable genetic trait of the crop to an undesirable interbreeding species having a genome compatible with one of said multiple genomes of the cultivated crop, the method comprising cytogenetically selecting a population of genetically engineered crop plants in which at least one engineered gene responsible for said genetically engineered, commercially desirable trait is localized on one or more of said multiple genomes of said cultivated crop, wherein said one or more of said multiple genomes is genetically incompatible with said genome of said undesirable interbreeding species thereby obtaining a cultivated crop capable of mitigating the effects of introgression of said genetically engineered, commercially desirable genetic trait of the cultivated crop to said undesirable interbreeding species.

According to yet another aspect of the present invention there is provided a method of obtaining a cultivated crop capable of mitigating the effects of introgression of at least one genetically engineered, commercially desirable genetic trait to an undesirable interbreeding species related to the cultivated crop, the method comprising transforming a population of plants of the cultivated crop to express the at least one genetically engineered commercially desirable genetic trait in the crop under genetic control of at least one genetic control element which is inexpressible by said undesirable interbreeding species related to the cultivated crop, thereby obtaining a cultivated crop capable of mitigating the effects of introgression of said genetically engineered, commercially desirable genetic trait of the cultivated crop to said undesirable interbreeding species related thereto.

According to a further aspect of the present invention there is provided a genetic construct for genetically modifying a cultivated crop to express a genetically engineered, commercially desirable genetic trait while mitigating the effects of introgression of said genetically engineered, commercially desirable genetic trait of the crop to an undesirable interbreeding species related to the cultivated crop, the genetic construct comprising a first polynucleotide encoding for said genetic trait and at least one additional polynucleotide comprising at least one control element which is expressible by the cultivated crop, said control element being inexpressible by said undesirable interbreeding species.

According to yet another aspect of the present invention there is provided a method of obtaining a cultivated crop capable of mitigating the effects of introgression of at least one genetically engineered, commercially desirable genetic trait to an undesirable, uncultivated interbreeding species related to the cultivated crop, the method comprising transforming a population of plants of the cultivated crop to co-express the at least one genetically engineered, commercially desirable genetic trait, and at least one genetically linked, mitigating genetic trait, wherein said mitigating genetic trait is selected such that an undesirable, uncultivated interbreeding species related to the cultivated crop expressing said mitigating genetic trait is less fit than an undesirable uncultivated interbreeding species related to the cultivated crop not expressing said mitigating genetic trait, thereby obtaining a cultivated crop capable of mitigating the effects of introgression of the at least one genetically engineered, commercially desirable genetic trait of the cultivated crop to the undesirable, uncultivated interbreeding species related thereto.

According to further features in preferred embodiments of the invention described below the at least one commercially desirable genetic trait is selected from the group consisting of herbicide resistance, disease, insect and nematode resistance, environmental stress resistance, high productivity, modified agronomic quality, enhanced yield, modified ripening, bioremediation, expression of heterologous products and genetically modified plant products.

According to yet further features in preferred embodiments of the invention described below the at least one mitigating genetic trait is selected from the group consisting of anti-seed shattering, abolished secondary dormancy, dwarfism, uniform or delayed ripening, seed stalk bolting, seed coat defects, uniform germination, root storage promotion, biennial growth, non-flowering and sterility.

According to still further features in preferred embodiments of the invention described below the at least one mitigating genetic trait is an endogeneous genetic trait of said cultivated crop.

According to further features in preferred embodiments of the invention described below the cultivated crop is tobacco, rice or oilseed rape, the commercially desirable genetic trait is herbicide resistance, and the mitigating genetic trait is gibberellic acid insensitivity.

According to yet further features in preferred embodiments of the invention described below the cultivated crop is corn, the commercially desirable genetic trait is expression of a heterologous pharmaceutical protein, and the mitigating genetic trait is endosperm-specific expression of a shrunken seed mutation.

According to still further features in preferred embodiments of the invention described below the cultivated crop is beets, the commercially desirable genetic trait is herbicide resistance, and the mitigating genetic trait is antibolting.

According to further features in preferred embodiments of the invention described below the cultivated crop is trees, the commercially desirable genetic trait is modified lignin, and the mitigating genetic trait is tapetum-specific expression of a cytotoxic gene.

According to another aspect of the present invention there is provided a genetic construct for mitigating the effects of introgression of a genetically engineered commercially desirable genetic trait of a cultivated crop to an undesirable, interbreeding species related to the cultivated crop, the genetic construct comprising a first polynucleotide encoding the at least one commercially desirable genetic trait and a second polynucleotide encoding at least one mitigating genetic trait, wherein said at least one mitigating genetic trait is selected such that an undesirable, interbreeding species related to the cultivated crop expressing said at least one mitigating genetic trait is less fit than an undesirable, interbreeding species related to the cultivated crop not expressing said at least one mitigating genetic trait and wherein expression of said commercially desirable and said at least one mitigating genetic trait is genetically linked, and a genetically modified cultivated crop comprising the genetic construct.

According to further features in preferred embodiments of the invention described below said first and said second polynucleotides are covalently linked.

According to still further features in preferred embodiments of the invention described below the first and said second polynucleotides are functionally linked.

According to yet further features in preferred embodiments of the invention described below the first and second polynucleotides are co-transformed.

According to still further features in preferred embodiments of the invention described below the first and second polynucleotides are integrated into the same chromosomal locus.

According to further features in preferred embodiments of the invention described below the at least one commercially desirable genetic trait is selected from the group consisting of herbicide resistance, disease, insect and nematode resistance, environmental stress resistance, high productivity, modified agronomic quality, enhanced yield, modified ripening, bioremediation, expression of heterologous products and genetically modified plant products.

According to still further features in preferred embodiments of the invention described below the at least one mitigating genetic trait is selected from the group consisting of anti-seed shattering, abolished secondary dormancy, dwarfism, uniform or delayed ripening, seed stalk bolting, seed coat defects, uniform germination, root storage promotion, biennial growth, non-flowering and sterility.

The present invention successfully addresses the shortcomings of the presently known configurations by conceiving and providing a mechanism for mitigating the effects of introgression of a genetically engineered genetic trait of a crop to a weed and of mitigating a weedy potential of the crop.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a depicts a circular map of the plasmid pPZP212-ahas$^R$-Δgai-1 (TM 1). Arrows indicate gene orientation; LB, left border; RB, right border; A, B, C and D indicated on the map denote the sites chosen for PCR amplification used to ascertain transformation with intact TM T-DNA. FIG. 1b is a linear map of the tandem genes assembled in direct orientation. FIG. 1c depicts an electrophoretic analysis of the TM construct plasmid DNA through a 1% (w/v) agarose gel at 50 volts for 45 min. Lane TM1 is the linearized TM 1 plasmid; lane M is molecular weight markers. FIG. 1d demonstrates the confirmation of the TM 1 plasmid construction by KpnI/SalI restriction enzyme digestion. The TM plasmid digest (lane 4) shows that the ahas$^R$-Δgai insert (lane 2) was found intact together with the binary vector. Lane 1 (M) is molecular weight markers; lane 3 is the native PZP212 plasmid DNA. FIG. 1e shows the detection of the transformed genes in transgenic tobacco plants by PCR. M, Molecular markers (1 kb DNA ladder); WT, wild type; (−), control without template DNA; P, TM 1 plasmid control; $T_0$, primary TM transgenic plants; lanes 1-10 denote different $T_3$-7 TM transgenic events; A, B, C, and D denote the sites chosen for PCR amplification as shown in FIG. 1a;

DESCRIPTION OF THE PREFERRED EMBODIMENTS

Figure 1:
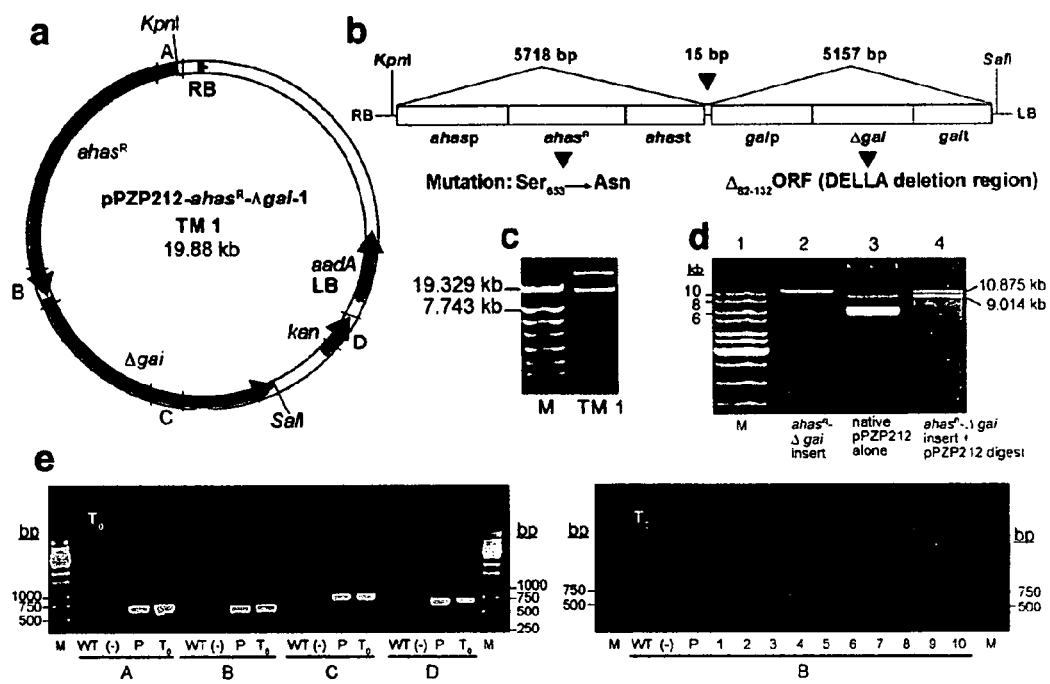
FIGS. 1a-e illustrate the assembly and verification of a TM tandem construct for transformation of tobacco plants.

The present invention is of genetic mechanisms which can be used for mitigating the effects of introgression of a genetically engineered genetic trait of a cultivated crop to an undesirable, interbreeding closely related species of the crop and for mitigating a weedy potential of the cultivated crop. Specifically, the present invention can be used to mitigate the effects of introgression of genetically engineered traits of cultivated crops after they have introgressed into weeds or related varieties of the crop.

The principles and operation of the present invention may be better understood with reference to the accompanying descriptions and examples.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All the information contained therein is incorporated herein by reference.

One of the greatest advantages of herbicide-resistant crops is that they allow control of closely-related weeds that have the same herbicide selectivity spectrum as the crop and could not be previously controlled. Similarly, an advantage of disease and insect resistant crops is that they can be grown where there are secondary hosts, often close relatives, harboring the pests. Other resistant crops, e.g., cold resistance crops, drought resistant crops, etc are also of great advantage. Highly productive crops are also advantageous, as are crops with modified product such as different types of starch and oils. These, and other genetic traits have been introduced into crops of various types by transgenics (see Table 2, herein below).

TABLE 2

Commercially desirable traits that have been engineered into crop plants

| Trait | Genetic Element | Source |
| --- | --- | --- |
| Fatty acid composition | delta(12)-fatty acid dehydrogenase (fad2) | *Glycine max* |
| Fatty acid composition | fatty acid desaturase (chemical mutagenesis) | NULL |
| Fatty acid composition | thioesterase (TE) | *Umbellularia californica* |
| Fertility restoration | barnase ribonuclease inhibitor barnase, barstar, PAT | *Bacillus amyloliquefaciens* |
| Herbicide resistance | 5-enolpyruvylshikimate-3-phosphate synthase (EPSPS) | *Agrobacterium tumefaciens* CP4 |

TABLE 2-continued

Commercially desirable traits that have been engineered into crop plants

| Trait | Genetic Element | Source |
|---|---|---|
| Herbicide resistance | 5-enolpyruvylshikimate-3-phosphate synthase (EPSPS) | *Z. mays* |
| Herbicide resistance | acetolactate synthase | chimera of 2 resistant AHAS genes (S4-Hr4) |
| Herbicide resistance | acetolactate synthase | chlorsulfuron tolerant line of *A. thaliana* |
| Herbicide tresistance | acetolactate synthase | chlorsulfuron tolerant *Nicotiana tabacum* |
| Herbicide resistance | glyphosate oxidoreductase | *Ochrobactrum anthropi* |
| Herbicide resistance | Nitrilase | *Klebsiella pneumoniae* subspecies *ozanae* |
| Herbicide resistance | phosphinothricin N-acetyltransferase | *S. hygroscopicus* |
| Herbicide resistance | phosphinothricin N-acetyltransferase | *S. viridochromogenes* |
| Insect resistance | Cry1 Ab delta-endotoxin (Btk HD-1) | *Bacillus thuringiensis* subsp. *kurstaki* (Btk) |
| Insect resistance | Cry1 Ac delta-endotoxin | *Bacillus thuringiensis* subsp. *kurstaki* (Btk) |
| Insect resistance | cry1F delta-endotoxin | *Bacillus thuringiensis* var. *aizawai* |
| Insect resistance | Cry2Ab delta-endotoxin | *Bacillus thuringiensis* |
| Insect resistance | cry3A delta-endotoxin | *Bacillus thuringiensis* subsp. *Tenebrionis* |
| Insect resistance | cry3Bb1 delta-endotoxin | *Bacillus thuringiensis* subsp. *kumamotoensis* |
| Insect resistance | cry9c delta-endotoxin | *Bacillus thuringiensis* subsp. *Tolworthi* |
| Insect resistance | protease inhibitor | *S. tuberosum* |
| Male sterility | barnase ribonuclease | *Bacillus amyloliquefaciens* |
| Male sterility | DNA adenine methylase | *Escherichia coli* |
| Modified color | dihydroflavonol reductase | *Petunia hybrida* |
| Modified color | flavonoid 3p, 5p hydroxylase | *Petunia hybrida* |
| Modified color | flavonoid 3p, 5p hydroxylase | *Viola* sp. |
| Herbicide resistance mutation | acetolactate synthase (ALS) | *Brassica napus* |
| Herbicide resistance mutation | acetolactate synthase | *Helianthus annus* |
| Herbicide resistance mutation | acetolactate synthase | *Oryza sativa* |
| Herbicide resistance mutation | acetolactate synthase | *Triticum aestivum* |
| Herbicide resistance mutation | acetolactate synthase | *Z. mays* |
| Herbicide resistance mutation | acetyl-CoA-carboxylase | *Z. mays* |
| Nicotine reduced | nicotinate-nucleotide pyrophosphorylase (carboxylating) | *Nicotiana tabacum* |
| Ripening delayed | 1-amino-cyclopropane-1-carboxylic acid synthase | *Dianthus caryophyllus* L. |
| Ripening delayed | 1-amino-cyclopropane-1-carboxylic acid deaminase | *Pseudomonas chlororaphis* |
| Ripening delayed | aminocyclopropane cyclase synthase | Tomato |
| Ripening delayed | polygalacturonase | Tomato |
| Ripening delayed | S-adenosylmethionine hydrolase | *E. coli* bacteriophage T3 |
| Virus resistance | helicase | potato leafroll luteovirus (PLRV) orf2 |
| Virus resistance | replicase (RNA dependent RNA polymerase) | potato leafroll luteovirus (PLRV) orf1 |
| Virus resistance | viral coat protein | Cucumber mosaic cucumovirus |
| Virus resistance | viral coat protein | papaya ringspot potyvirus (PRSV) |
| Virus resistance | viral coat protein | potato potyvirus Y (PVY) strain O (common strain) |
| Virus resistance | viral coat protein | Watermelon mosaic potyvirus 2 |
| Virus resistance | viral coat protein | Zucchini yellow mosaic potyvirus |

Table available at APHIS

Some specific crops have been broadly engineered to include the commercially advantageous traits listed above. For example, some of the more well known transgenic traits, and the genes responsible for them, that have been introduced into use in oilseed rape production, are listed in Table 3 herein below.

TABLE 3

Examples of primary advantageous genes inserted into oilseed rape for potentially commercial purposes in USA

| Type of gene/phenotype | Gene | APHIS # |
|---|---|---|
| *Herbicide Resistance* | | |
| CBI | CBI | 03-254-03 |
| Glyphosate | EPSP synthase | 01-080-04 |
|  | glyphosate oxidoreductase | 96-045-02 |
| Glufosinate | CBI | 00-023-05 |
|  | Phosphinothricin acetyl transferase | 98-274-10 |
| Bromoxynil | nitrilase | 98-243-02 |
| Sulfonylurea | acetolactate synthase | 96-102-01 |
| *Insect Resistance* | | |
| Lepidopteran | CryIA(c) | 02-312-02 |
|  | Trypsin inhibitor | 99-098-05 |
|  | proteinase inhibitor II + CryIA(c) | 94-326-01 |
| *Disease resistance (fungal)* | | |
| *Cylindrosporium* + *Phoma* | chitinase + glucanase | 01-074-11 |
| post harvest | coat protein | 97-078-02 |
| *Agronomic traits* | | |
| Nitrogen metabolism altered | alanine amino transferase | 03-276-04 |
| Cold tolerance | cold regulated gene binding factor | 01-066-07 |
| Male sterility/fertility | CBI | 03-254-03 |
|  | Barnase/Barstar | 98-119-01 |
| Yield increase | sucrose phosphate synthase | 98-064-20 |
| *Product Quality* | | |
| Oil profile altered | Acyl CoA reductases, Acyl-ACP thioesterases, elongase, ketoacyl-ACP synthases | 97-022-02 |
|  | Acyl-ACP-thioesterase + Delta 12 saturase, Delta 9 + 15 desaturases | 01-068-01 |
|  | Acetyl CoA carboxylase | 99-067-02 |
|  | 34 different genes | 96-071-07 |
| Lysine increased | Dihydropicolinate synthase | 98-099-03 |
| Pharmaceutical protein | CBI | 96-215-01 |
| Polymer | CBI | 96-061-02 |
| Industrial enzymes | CBI | 93-048-02 |

The advantages of transgenics are well appreciated, if there is no introgression into an undesirable, interbreeding closely related species (weed) or if the crop itself does not become a "volunteer" weed in subsequent crops. Because the advantages of transgenics are so great, as in the above cases, both industry and farmers are clamoring for the new modified transgenic crops. In fact, genetically modified plants having higher yield or superior herbicide resistance are in great demand, even when it is known that introgression to weeds is possible and imminent. However, if the gene for herbicide resistance introgresses into weedy or volunteer species, the farmers are potentially worse off than before. Considering, for example, the strong competition of red-rice with rice, and the magnitude of yield loss (Pantone and Baker, 199 1; and Chin, Weed Biol Management, 2001;1:pg 37), the desire of the farmers to rapidly deploy new technologies can be understood. One cannot state that this argument is wrong; just that there are a limited number of herbicide resistances one can engineer and thus a limited number of times that one can return to square one.

Hence, while conceiving the present invention, the concept of mitigating the risks of introgression of a genetically engineered trait of a cultivated crop to a weed by coupling the desirable, primary gene of choice having the desired trait in tandem constructs with "antiweediness", mitigating genes conferring a disadvantage on weedy and volunteer recipients, while being benign or advantageous to the cultivated crop was formulated. This coupling can either be physical, where the two genes are covalently linked prior to transformation or by the same physical juxtaposition commonly achieved by co-transformation. Both will heretofore be termed "tandem", as the result in tightly linked genes. These would render weedy recipients or volunteer weeds less fit to act as competitors with crops, weeds and wild species. As further detailed and exemplified herein below, genes that prevent seed shatter, that prevent secondary dormancy, that dwarf the recipient and others would all be useful for that purpose, as they would often be benign or advantageous to the cultivated crop while detrimental to weeds, or to the crop when it is a "volunteer" weed, i.e., when it becomes a weed in the following crop, or if it becomes feral.

As used herein in the specification and in the claims section that follows, the term "weed" includes undesirable plants growing wild, especially those growing on cultivated ground to the disadvantage of a cultivated crop, lawn, or flower bed. In the broadest sense, the term weed is defined as all plants which grow in locations where they are undesired, including, for example: dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolwlus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*, weedy varieties of dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia;* monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*, and weedy varieties of monocotyledonous crops of the genera: *Allium, Ananas, Asparagus, Avena, Hordeum, Oryza, Panicum, Saccharum, Secale, Sorghum, Triticale, Triticum, Zea.* The term further includes various forms of the crop species that are undesirable to agriculture: feral forms that have escaped cultivation and have evolved weedy characters, undesirable, uncultivated interbreeding species related to the cultivated crop, other varieties of the crop that do not possess the same transgenes, and the transgenic crop when it is a volunteer weed in following crops.

According to one aspect of the present invention there is provided a s method of obtaining a cultivated crop capable of mitigating the effects of introgression of at least one genetically engineered, commercially desirable genetic trait to an undesirable interbreeding species related to the cultivated crop The method is effected by producing apomictic seeds of the crop of a type which give rise to male sterile crop plants, to thereby obtain a cultivated crop capable of mitigating the effects of introgression of the genetically engineered, commercially desirable genetic trait to the undesirable interbreeding species related thereto.

Male sterility in plants implies an inability to produce or to release functional (fertile) pollen. Male sterility in plants results in failure of formation or development of functional stamens, microspores or gametes.

From a structural/functional point of view, male sterility in plants may be divided into three categories which include (i) pollen sterility, wherein functional pollen grains are missing; (ii) structural (or staminal) male sterility, wherein male flowers or stamens are malformed and therefore non-functional, or missing altogether; and (iii) functional male sterility, wherein good and viable pollen is trapped in indehiscent anthers and thus prevented from functioning.

From a genetic point of view, male sterility in plants may also be divided into three categories which include (i) nuclear male sterility (NMS), also known in the art as genic or Mendelian male sterility, wherein male sterility is governed solely by one or more nuclear genes; (ii) cytoplasmic male sterility (CMS), wherein male sterility results due to a combined action of nuclear and cytoplasmic organelle (e.g., mitochondria or chloroplasts) genes; and (iii) non-genetic male sterility which is either chemically or mechanically (pollen removal) induced.

As further detailed hereinunder male sterility genes have been isolated and characterized. Such genes can be used to produce the apomictic seeds according to the present invention using genetic engineering techniques which are well known in the art, some of which are further described hereinunder.

According to a further aspect of the present invention there is provided a method of obtaining a cultivated crop having multiple genomes derived from different wild sources capable of mitigating the effects of introgression of at least one genetically engineered, commercially desirable genetic trait of the crop to an undesirable interbreeding species having a genome compatible with one of the multiple genomes of the cultivated crop. The method is effected by cytogenetically selecting a population of genetically engineered crop plants in which at least one engineered gene responsible for the genetically engineered, commercially desirable trait is localized on one or more of the multiple genomes of the cultivated crop, and one or more of the multiple genomes is genetically incompatible with the genome of the undesirable interbreeding species thereby obtaining a cultivated crop capable of mitigating the effects of introgression of the genetically engineered, commercially desirable genetic trait of the cultivated crop to the undesirable interbreeding species.

For example, the D genome of wheat is compatible with the D genome of *Aegilops cylindrica* (goatgrass) a problematic weed in the western plain states of the U.S. Transgenes can introgress from wheat to this *Aegilops* (Zemetra et al., 1998). Likewise, transgenes easily introgress from the B genome of oilseed rape to many *Brassica* weeds and wild species (Darmency, 1994; Bing et al., 1996; Brown and Brown, 1996; Jorgensen and Andersen, 1994; Kerlan et al., 1993; Landbo et al., 1996; Lefol et al., 1996a, b Metz et al., 1997; Mikkelsen et al., 1997; Scheffler et al., 1995). Selecting for wheat and oilseed rape transgenic plants in which no transgenes are integrated in the D or B genomes, will mitigate the possibility of introgression of the transgenic trait to *Aegilops cylindrica* and *Brassica* weeds and wild species, respectively.

Conventional methods of gene mapping in plants and the availability of genetic markers being specific to the chromosomes of the various genomes can be employed using well known and developed cytogenetic techniques to select for genetically engineered crop plants in which a gene or genes responsible for the trait are localized on one or more of the multiple genomes of the crop, which genome is not compatible with the genome of the weed.

According to yet another aspect of the present invention there is provided a method of mitigating the effects of introgression of a genetically engineered trait of a crop to a weed. The method according to this aspect of the invention is effected by cytogenetically selecting for or producing genetically engineered crop plants in which a gene or genes responsible for the trait are genetically linked to an endogenous trait of the crop, the endogenous being deleterious to the weed.

According to yet another aspect of the present invention there is provided a method of obtaining a cultivated crop capable of mitigating the effects of introgression of at least one genetically engineered, commercially desirable genetic trait to an undesirable interbreeding species related to the cultivated crop. The method according to this aspect of the invention is effected by transforming a population of plants of the cultivated crop to express the at least one genetically engineered commercially desirable genetic trait in the crop under genetic control of at least one genetic control element which is inexpressible by undesirable interbreeding species related to the cultivated crop.

Accordingly, the present invention provides a genetic construct for genetically modifying a cultivated crop to express a genetically engineered, commercially desirable genetic trait while mitigating the effects of introgression of said genetically engineered, commercially desirable genetic trait of the crop to an undesirable interbreeding species related to the cultivated crop. The genetic construct comprises a first polynucleotide encoding for the genetic trait and at least one additional polynucleotide comprising at least one control element which is expressible by the cultivated crop, yet inexpressible by the undesirable interbreeding species. These constructs can be tandemly produced, or the same effect can be achieved by co-transformation and co-locus integration.

One example of a control element which is expressible by a cultivated crop, yet is inexpressible by related undesirable interbreeding species (weeds) is the 35S promoter which was originally derived from cauliflower mosaic virus (CaMV) and which is silenced in plants infected by the virus (Al-Kaff et al., 1998)—i.e., most cruciferous weed plants in the wild. One of the basic and fundamental mechanisms in the process of speciation (species formation) is loss or gain of genetic control functions. It is therefore expected that a plurality of genetic control element will be functional in one species, yet non-functional in even a closely related species.

According to yet another aspect of the present invention there is provided a method of obtaining a cultivated crop capable of mitigating the effects of introgression of at least one genetically engineered, commercially desirable genetic trait to an undesirable, uncultivated interbreeding species related to the cultivated crop (e.g. a weed). The method is effected by transforming a population of plants of the cultivated crop to co-express the at least one genetically engineered, commercially desirable genetic trait, and at least one genetically linked, mitigating genetic trait. The mitigating genetic trait is selected such that an undesirable, uncultivated interbreeding species related to the cultivated crop expressing the mitigating genetic trait is less fit than an undesirable uncultivated interbreeding species related to the cultivated crop not expressing the mitigating genetic trait, thereby obtaining a cultivated crop capable of mitigating the effects of introgression of the genetically engineered, commercially desirable genetic trait of the cultivated crop to the undesirable, uncultivated interbreeding related species. In a preferred embodiment, the mitigating genetic trait is innocuous or somewhat valuable to the cultivate crop yet deleterious to the undesirable interbreeding related species (weed).

As used herein the term genetically linked refers to a genetic distance smaller than 50 centiMorgan, preferably smaller than 40 centiMorgan, more preferably smaller than 30 centiMorgan, more preferably smaller than 20 centiMorgan, more preferably smaller than 10 centiMorgan, more preferably smaller than 5 centiMorgan, more preferably smaller than 1 centiMorgan, most preferably in the range of 0 to 1 centiMorgan, wherein 0 centiMorgan refers to juxtaposed sequences.

Accordingly, the present invention also provides a genetic construct for mitigating the effects of introgression of a genetically engineered commercially desirable genetic trait of a cultivated crop to an undesirable, interbreeding species related to the cultivated crop. The genetic construct comprises a first polynucleotide encoding at least one commercially desirable genetic trait and a second polynucleotide encoding at least one mitigating genetic trait. Expression of the commercially desirable and the mitigating genetic trait is genetically linked. The polynucleotide encoding the first, primary genetic trait is preferably flanked on both sides by polynucleotides encoding the second, mitigating genetic trait, to thereby reduce the risk of loosing the second, mitigating genetic trait due to mutation or crossing over.

However, it will be appreciated that in many cases while using conventional transformation techniques genetic traits carried on two different vectors end up integrating to the same locus.

Thus, according to a further aspect of the present invention there is provided a cultivated crop genetically modified to include the above described genetic constructs and to express the traits encoded thereby.

In one embodiment, the second, mitigating genetic trait is selected from the group consisting of anti-seed shattering, abolished secondary dormancy, dwarfism, uniform or delayed ripening, seed stalk bolting, seed coat defects, uniform germination, root storage promotion, biennial growth, non-flowering and sterility, these traits being benign or somewhat valuable to the cultivated crop, yet deleterious to the undesirable, interbreeding related species (weed). Numerous specific examples of such genetic traits are listed herein and are further discussed in the Examples section that follows.

One such mitigating trait is abolished secondary dormancy. Genetically abolished secondary dormancy would be neutral to the crop, or advantageous to some crops having some residual secondary dormancy, but deleterious to the weed. Tillage, crop rotation, and preplant use of herbicides, all standard practices, would control the uniformly-germinating weed seeds lacking secondary dormancy during the following season.

Another such mitigating trait is uniform or delayed ripening. For example, methods and constructs for controlling the ripening of fruits and vegetables are disclosed in U.S. Pat. Nos. 5,512,466 and 5,702,933 to Klee et al, which teaches the expression of an ACC metabolizing enzyme in the fruit to inhibit the production of ethylene, and U.S. Pat. No. 6,118,049 to Bestwick et al, which teaches the expression of heterologous S-adenosylmethionine hydrolase under control of a fruit-specific E4/E8 promoter.

Yet another such mitigating trait is of anti-shattering of ripe seeds. Uniform ripening and anti-shattering genes would be a negative trait for weeds, neutral for uniformly ripening and non-shattering crops (e.g., rice), and positive, for example, for oilseed rape, which still has a shattering problem.

Still another such mitigating trait is dwarfism. Examples for dwarfism genes include genes relating to hormone production (Azpiroz et al., 1998; Schaller et al., 1998) as well as those dealing with shade avoidance, such as, but not limited to, over expressed phytochrome genes which prevents recognition of shading and thus the plant remains short (Robson et al., 1996). Additional examples are provided in the Examples section that follows.

Additional traits suitable for mitigation of introgression, whose phenotypic expression is benign or advantageous to a cultivated crop, yet deleterious to a weed or weedy variety of the crop include, but are not limited to, seed stalk bolting, seed coat defects that facilitate uniform germination, root storage promotion, biennial growth and non-flowering.

Thus, these introgression-mitigating, anti-weediness traits are combined, according to the present invention, with the desirable genetically engineered traits, which genetically engineered traits include, but are not limited to, traits imposing resistance to herbicides, disease, insects, nematodes and other plant pests and pathogens, resistance to environmental stress such as, but not limited to, cold, salinity, etc., and traits affecting yield, ripening, productivity, modified agronomic quality, bioremediation, as well as expression of heterologous products and genetically modified plant products such as starches and oils, etc. Such traits for which genes has been isolated are well known in the art, for example, genes modifying fatty content [delta(12)-fatty acid dehydrogenase (fad2), fatty acid desaturase, and thioesterase (TE)], fertility restoration genes (barnase ribonuclease inhibitor barnase, barstar, PAT), herbicide tolerance genes (5-enolpyruvylshikimate-3-phosphate synthase (EPSPS), acetolactate synthase, glyphosate oxidoreductase, nitrilase, phosphinothricin N-acetyltransferase), insect resistance genes [Cry1Ab delta-endotoxin (Btk HD-1), Cry1Ac delta-endotoxin, cry1F delta-endotoxin, Cry2Ab delta-endotoxin, cry3A delta-endotoxin, cry3Bb 1 delta-endotoxin, cry9c delta-endotoxin, protease inhibitor], male sterility genes (barnase ribonuclease DNA adenine methylase), genes for modified color (dihydroflavonol reductase, flavonoid 3p, 5p hydroxylase), genes conferring favorable mutations (acetolactate synthase (ALS) and acetyl-CoA-carboxylase), genes for reduced nicotine in tobacco [nicotinate-nucleotide pyrophosphorylase (carboxylating)], genes for delayed ripening (1-amino-cyclopropane-1-carboxylic acid synthase, polygalacturonase, S-adenosyl-methionine hydrolase), and numerous viral resistance genes [helicase replicase (RNA dependent RNA polymerase) and various specific viral coat protein genes]. Additional suitable genes are listed in Tables 1-8, and summarized in many recent texts such as Galun and Breiman, 1997.

Traits for which genes have yet not been isolated, but may be isolated by well known protein and nucleic acid screening methods include biennial growth promotion, etc.

Once a gene responsible for a mitigating trait has been selected, it must be engineered for plant expression along with the desirable trait that confers an advantage thereto. To introduce such genes into a plant, a suitable chimeric gene and transformation vector must be constructed. A typical chimeric gene for transformation into a plant will include a promoter region, a heterologous structural DNA coding sequences and a 3' non-translated polyadenylation site. A heterologous structural DNA coding sequence means a structural coding sequence that is not native to the plant being transformed. Heterologous with respect to the promoter means that the coding sequence does not exist in nature in the same gene with the promoter to which it is now attached.

Chimeric means a novel non-naturally occurring gene which is comprised of parts of different genes. In preparing the transformation vector, the various DNA fragments may be manipulated as necessary to create the desired vector. This includes using linkers or adaptors as necessary to form suitable restriction sites or to eliminate unwanted restriction sites or other like manipulations which are known to those of ordinary skill in the art.

Promoters which are known or found to cause transcription of selected gene or genes in plant cells can be used to implement the present invention. Such promoters may be obtained from plants, plant pathogenic bacteria or plant viruses and include, but are not necessarily limited to, strong constitutive promoter such as a 35S promoter (Odell et al (1985) Nature 313, 810-812), a 35S'3 promoter (Hull and Howell (1987) Virology 86, 482-493) and the 19S promoter of cauliflower mosaic virus (CaMV35S and CaMV19S), the full-length transcript promoter from the figwort mosaic virus (FMV35S) and promoters isolated from plant genes such as EPSP synthase, ssRUBISCO genes and promoters obtained from T-DNA genes of *Agrobacterium tumefaciens* such as the promoter of the nopaline synthetase gene ("PNOS") of the Ti-plasmid (Herrera-Estrella (1983) Nature 303, 209-213), the mannopine synthase promoter, or the promoter of the octopine synthase gene ("POCS" [De Greve et al (1982) J. Mol. Appl. Genet. 1 (6), 499-511]). Also useful can be expression in wound tissue, for example, using a second promoter which is a TR promoter such as the TRi' or TR2' promoter of the Ti-plasmid (Velten et al (1984) EMBO J. 3, 2723-2730). Selective expression in green tissue can be achieved by using, for example, the promoter of the gene encoding the small subunit of Rubisco (European patent application 87400544.0 published Oct. 21, 1987, as EP 0 242 246). Promoters can be selected so that the transgenes are expressed in specific cells, such as petal cells, leaf cells or seed cells, preferably in the outer layer of the seed coat. All of these promoters have been used to create various types of DNA constructs that have been expressed in plants. See, for example PCT publication WO 84/02913 (Rogers et al., Monsanto, herein incorporated by reference in its entirety). The particular promoter selected should be capable of causing sufficient expression to result in the production of an effective amount of the respective proteins to confer the traits.

Particularly useful promoters for use in some embodiments of the present invention are fruit specific promoters and the full-length transcript promoter from the figwort mosaic virus (FMV35S). The FMV35S promoter is particularly useful because of its ability to cause uniform and high levels of expression in plant tissues. The DNA sequence of a FMV35S promoter is presented in U.S. Pat. No. 5,512,466 and is identified as SEQ ID NO:17 therein. Other examples of fruit specific promoters include the E8, E4, E17 and J49 promoters from tomato (Lincoln et al., 1988), as well as the 2A11 promoter as described in U.S. Pat. No. 4,943,674. Tapetum and anther specific promoters can be used to isolate gene expression to reproductive organs, to achieve, for example, male sterility. Promoters that show this specificity are well known. Especially useful are the tapetum-specific promoter Tap1 as described in Nacken et al. Sol. Gen. Genet. 229, 129-136, 1991), the tapetum specific promoters A9 (WO 92/11379), T29, PTA 29, PTA 26 and PTA13 as well as any promoter of a gene encoding a tapetum-specific mRNA hybridizable to the genes TA29, TA26 or TA13 from which genes the PTA29, PTA26 and PTA13 promoters have been isolated (U.S. Pat. Nos. 5,652,354 and 6,046,382 to Mariani et al), the anther specific promoters described in WO 92/18625, WO 90/08826 and European patent application EP 93810455.1, and the tapetum specific promoter MFS14 (WO 97/04116). Examples of female organ-specific promoters and sterility promoters are: the style and/or stigma-specific promoters, such as PSTMG07, PSTMG08, PSTMG4B12 and PSTMG3C9, and the ovule-specific promoter corresponding to the cDNA clone pMON9608 as described in U.S. Pat. No. 5,633,441; as well as a promoter of a gene encoding i) a style-stigma specific or ii) an ovule-specific mRNA hybridizable respectively to i) a STMG-type style-stigma specific gene or ii) CDNA clone pMON9608 of U.S. Pat. No. 5,633, 441. Several other promoters are known in the art (see, e.g., McCormick et al. "Anther-Specific Genes: Molecular Characterization and Promoter Analysis in Transgenic Plants" in Plant Reproduction: From Floral Induction to Pollination, Lord et al. (ed.), 128-135, 1989; and Scott et al., 1992, The Plant Cell 4, 253, and U.S. Pat. No. 6,603,064 to Van Dun) and as long as they give specific expression in the reproductive system, choice of the promoter is not critical to the invention.

The promoters used for expressing the genes according to the present invention may be further modified if desired to alter their expression characteristics. For example, the CaMV35S promoter may be ligated to the portion of the ssRUBISCO gene which represses the expression of ssRUBISCO in the absence of light, to create a promoter which is active in leaves but not in roots. The resulting chimeric promoter may be used as described herein. As used herein, the phrase "CaMV35S" or "FMV35S" promoter includes variations of these promoters, e.g., promoters derived by means of ligation with operator regions, random or controlled mutagenesis, addition or duplication of enhancer sequences, etc.

The 3' non-translated region contains a polyadenylation signal which functions in plants to cause the addition of polyadenylated nucleotides to the 3' end of an RNA sequence. Examples of suitable 3' regions are the 3' transcribed, non-translated regions containing the polyadenylation signal of the tumor-inducing (Ti) plasmid genes of *Agrobacterium*, such as the nopaline synthase (NOS) gene, and plant genes like the 7s soybean storage protein genes and the pea E9 small subunit of the RuBP carboxylase gene (ssRUBISCO).

The RNAs produced by a DNA construct of the present invention also preferably contains a 5' non-translated leader sequence. This sequence can be derived from the promoters selected to express the genes, and can be specifically modified so as to increase translation of the mRNAs. The 5' non-translated regions can also be obtained from viral RNA's, from suitable eukaryotic genes, or from a synthetic gene sequence. The present invention is not limited to constructs wherein the non-translated region is derived from the 5' non-translated sequence that accompanies the promoter sequence. Rather, the non-translated leader sequences can be part of the 5' end of the non-translated region of the native coding sequence for the heterologous coding sequence, or part of the promoter sequence, or can be derived from an unrelated promoter or coding sequence as discussed above.

In a preferred embodiment according to the present invention, the vector that is used to introduce the encoded proteins into the host cells of the plant will comprise an appropriate selectable marker. In a more preferred embodiment according to the present invention the vector is a plant expression vector comprising both a selectable marker and an origin of replication. In another most preferred embodiment according to the present invention the vector will be a shuttle vector, which can propagate both in *E. coli* (wherein the construct comprises an appropriate selectable marker and origin of replication) and be compatible for propagation or integration in the genome of the plant organism of choice. In yet another embodiment, the construct comprising the promoter of choice, and the gene of interest is placed in a viral vector which is used to infect the cells. This virus may be integrated in the genome of the organism of choice or may remain non-integrated.

According to some embodiment of the present invention secretion of the protein or proteins out of the cell is preferred. In this embodiment the construct will comprise a signal sequence to effect secretion as is known in the art. For some applications, a signal sequence that is recognized in the active growth phase will be most preferred. As will be recognized by the skilled artisan, the appropriate signal sequence should be placed immediately downstream of the translational start site (ATG), and in frame with the coding sequence of the gene to be expressed.

Introduction of the construct into the cells is accomplished by any conventional method for transfection, infection or the like as is known in the art. In constructs comprising a selectable marker the cells may be selected for those bearing functional copies of the construct. If the plasmid comprising the gene of interest is episomal the appropriate selective conditions will be used during growth. Stable transfectants and stable cell lines may be derived from the transfected cells in appropriate cases, in order to conveniently maintain the genotype of interest. Cell growth is accomplished in accordance with the cell type, using any standard growth conditions as may be suitable to support the growth of the specific cell line.

A DNA construct of the present invention can be inserted into the genome of a plant by any suitable method. Suitable plant transformation vectors include those derived from a Ti plasmid of *Agrobacterium tumefaciens*, such as those disclosed by U.S. Pat. No. 4,940,838 and others. In addition to plant transformation vectors derived from the Ti or root-inducing (Ri) plasmids of *Agrobacterium*, alternative methods can be used to insert the DNA construct of this invention into plant cells. Such methods may involve, for example, the use of liposomes, electroporation, chemicals that increase free DNA uptake such as polyethylene glycol (PEG), vacuum filtration, particle gun technology (biolostic bombardment with tungsten or gold particles; see, for example, Sanford et al., U.S. Pat. No. 4,945,050; McCabe et al. (1988) Biotechnology, 6:923-926). Also see, Weissinger et al. (1988) Annual Rev. Genet., 22:421-477; Datta et al. (1990) Biotechnology, 8:736-740; Klein et al. (1988) Proc. Natl. Acad. Sci. USA, 85:4305-4309; Klein et al. (1988) Biotechnology, 6:559-563 (maize); Klein et al. (1988) Plant Physiol., 91:440-444; Fromm et al. (1990) Biotechnology, 8:833-839; and Tomes et al. "Direct DNA transfer into intact plant cells via microprojectile bombardment." In: Gamborg and Phillips (Eds.) Plant Cell, Tissue and Organ Culture: Fundamental Methods; Springer-Verlag, Berlin (1995); Hooydaas-Van Slogteren & Hooykaas (1984) Nature (London), 311:763-764; Bytebier et al. (1987) Proc. Natl. Acad. Sci. USA, 84:5345-5349; all of which are herein incorporated by reference) and other mechanical DNA transfer techniques, and transformation using viruses. Methods for the introduction of vectors into maize, or other monocot cells are well known in the art, as described, for example, in U.S. Pat. Nos. 6,002,070 and 5,641,661 to D'Halluin et al. Such techniques include, but are not limited to, injection methods or microprojectile methods, as described in detail herein below.

The construction of vectors capable of being inserted into a plant genome via *Agrobacterium tumefaciens* mediated delivery is known to those of ordinary skill in the art. See, for example, the methods described by Fraley et al., Biotechnology, 3:629 (1985) and Rogers et al., Methods in Enzymology, 153:253-277 (1987). Further, the integration of the Ti-DNA is a relatively precise process resulting in few rearrangements. The region of DNA to be transferred is defined by the border sequences and intervening DNA is usually inserted into the plant genome as described by Spielmann et al., Mol. Gen. Genet., 205:34 (1986) and Jorgensen et al., Mol. Gen. Genet., 207:471 (1987). Modern *Agrobacterium* transformation vectors are capable of replication in *Escherichia coli* as well as *Agrobacterium*, allowing for convenient manipulations as described by Klee et al., in Plant DNA Infectious Agents, T. Hohn and J. Schell, eds., Springer-Verlag, New York (1985) pp. 179-203. Further technological advances in vectors for *Agrobacterium*-mediated gene transfer have improved the arrangement of genes and restriction sites in the vectors to facilitate construction of vectors capable of expressing various polypeptide coding genes. The vectors described by Rogers et al., Methods in Enzymology, 153:253 (1987), have convenient multi-linker regions flanked by a promoter and a polyadenylation site for direct expression of inserted polypeptide coding genes and are suitable for present purposes.

*Agrobacterium*-mediated transformation of leaf disks and other tissues appears to be limited to plant species that *Agrobacterium tumefaciens* naturally infects. Thus, *Agrobacterium*-mediated transformation is most efficient in dicotyledonous plants. However, the transformation of Asparagus using *Agrobacterium* can also be achieved. See, for example, Bytebier, et al., Proc. Natl. Acad. Sci., 84:5345 (1987).

In those plant species where *Agrobacterium*-mediated transformation is efficient, it is the method of choice because of the facile and defined nature of the gene transfer. Although few monocots appear to be natural hosts for *Agrobacterium*, transgenic plants have been produced in asparagus using *Agrobacterium* vectors as described by Bytebier et al., Proc. Natl. Acad. Sci. U.S.A., 84:5345 (1987) and for sorghum, as described by Cai et al (U.S. Pat. No. 6,369,298. Where necessary, commercially important cereal grains such as rice, corn, and wheat can be transformed using alternative methods.

Application of these systems to different plant species depends upon the ability to regenerate that particular plant species from protoplasts. Illustrative methods for the regeneration of cereals from protoplasts are described in Fujimura et al., Plant Tissue Culture Letters, 2:74 (1985); Toriyama et al., Theor Appl. Genet., 73:16 (1986); Yamada et al., Plant Cell Rep., 4:85 (1986); Abdullah et al., Biotechnology, 4:1087 (1986). Typical plant cloning vectors comprise selectable and scorable marker genes, T-DNA borders, cloning sites, appropriate bacterial genes to facilitate identification of transconjugates, broad host-range replication and mobilization functions and other elements as desired.

If *Agrobacterium* mediated delivery is chosen, once the vector has been introduced into the disarmed *Agrobacterium* strain, the desired plant can then be transformed. Any known method of transformation suitable for the desired plant can be utilized.

Once transgenic plant tissue which contains an expression vector has been obtained, transgenic plants are regenerated from this transgenic plant tissue. The term "regeneration" as used herein, means growing a whole plant from a plant cell, a group of plant cells, a plant part or a plant piece. Transformed plant cells which are derived by any of the above transformation techniques are cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the nucleic sequence of interest. Regeneration techniques for regenerating plants from plant callus, explants, organs, or parts thereof are described generally in Klee et al. Ann. Rev. of Plant Phys. 38:467-486 (1987). The culture media will generally contain various organic components including vitamins, sugars, and plant hormones, such as auxin and cytokinins, as well as inorganic salts. The regenerated plants are transferred to standard soil conditions and cultivated in a conventional manner.

Confirmation of the transgenic nature of the cells, tissues, and plants may be performed by PCR analysis, antibiotic or herbicide resistance, enzymatic analysis and/or Southern blots to verify transformation. Progeny of the regenerated plants may be obtained and analyzed to verify whether the transgenes are heritable. Heritability of the transgene is further confirmation of the stable transformation of the transgene in the plant. Progeny may be sexually or asexually derived progeny.

After the desired genes or construct is stably incorporated into regenerated transgenic plants, they can be transferred to other plants by sexual crossing. The plants are then grown and harvested using conventional procedures.

Additional objects, advantages, and novel features of the present invention will become apparent to one ordinarily skilled in the art upon examination of the following examples, which are not intended to be limiting. Additionally, each of the various embodiments and aspects of the present invention as delineated herein above and as claimed in the claims section below finds experimental support in the following examples.

EXAMPLES

Reference is now made to the following examples, which together with the above descriptions, illustrate the invention in a non limiting fashion.

Introgression Failsafes

There are various failsafe mechanisms that can be used to prevent or reduce the risk of introgression of traits between genetically engineered crops and weeds.

Apomixis as a failsafe: One area that may develop is apomixis (Koltunow et al., 1995), where seed is actually of vegetative origin. This is being developed to establish hybrid vigour without crosses. If apomictic varieties are pollen free, then genes cannot introgress into other species or into varieties of a crop. The lack of viable pollen is probably the only failsafe that would be acceptable to some detractors, who fear intervarietal movement of transgenes.

Cytogenetic Failsafes: Some crops such as wheat and oilseed rape are composed of multiple genomes derived from different wild sources (Kimber and Sears, 1997; U, 1935). In any given locale it is possible that only one of the genomes of the crop is identical to that of a related weed allowing easy gene transfer. For example: the D genome of wheat is compatible with the D genome of *Aegilops cylindrica* (bearded goatgrass) a problematic weed in the western plain states of the U.S. Transgenes can introgress from wheat to this *Aegilops* (Zemetra et al., 1998). Likewise, transgenes easily introgress from the B genome of oilseed rape to many *Brassica* weeds and wild species (Darmency, 1994; Bing et al., 1996; Brown and Brown, 1996; Jorgensen and Andersen, 1994; Kerlan et al., 1993; Landbo et al., 1996; Lefol et al., 1996a, b Metz et al., 1997; Mikkelsen et al., 1997; Scheffler et al., 1995). The further the genetic distances of between crop and weed in these crosses, the greater the needs for techniques such as embryo rescue to save hybrids abortion, and the greater the incidence of infertile offspring. The natural integration of a transgene on the D genome of wheat or the B genome of oilseed rape in interspecific crosses is quite simple. This should not be the case if the transgene is on the incompatible A or B genomes of wheat or the C genome of oilseed rape. When the transgene is on one of the incompatible genomes, rare homologous recombination (crossing over) is required to integrate the transgene into stable and fertile offspring. Thus, cytogenetic mapping of transgenes, and releasing only those transgenic lines where the transgene is on genome incompatible with local weeds will lower the risk of introgression with weeds by orders of magnitude (Gressel and Rotteveel, 1999). Surprisingly, such risk lowering has not appeared among the requirements of regulatory authorities (Anonymous, 1994a, b, 1997; Be et al., 1996; Waters, 1996).

Transgenetic Mitigation (TM) Mitigating "Flow" of "Leaked" Primary Transgenes

Figure 9:
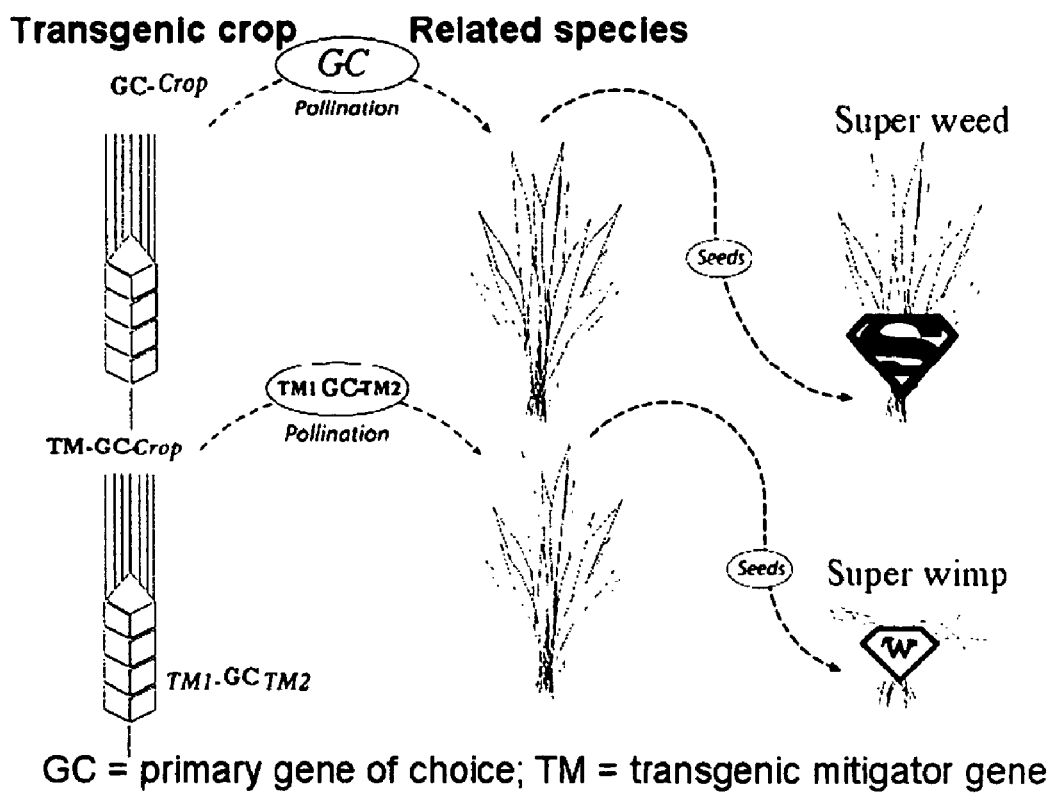
FIG. 9 is a schematic illustrating the concept of transgenic mitigation of introgression of genetically engineered traits (TM) into undesirable species (weedy varieties and volunteer weeds)

The concept of using genetic engineering to mitigate any positive effects transgenes may confer, in the event of introgression, is based on the following premise: If a transgene construct has a small fitness disadvantage, it will remain localized as a very small proportion of the population. Therefore, gene flow should be mitigated by lowering the fitness of recipients below the fitness of the wild type so that they will not spread. This concept of "transgenic mitigation" (TM) was proposed (Gressel, J. 1999: Tandem constructs: preventing the rise of superweeds. Trends Biotech. 17: 361-366), (see FIGS. 9 and 10) in which mitigator genes are added to the desired primary transgene, which would reduce the fitness advantage to hybrids and their rare progeny, and thus considerably reduce risk (see also WO 04/46362, from which the present invention claims priority).

The TM approach is based on the facts that: 1) tandem constructs act as tightly linked genes, and their segregation from each other is exceedingly rare, far below the natural mutation rate; and 2) The TM traits chosen are selected to be nearly neutral or favorable to the cultivated crops, but deleterious to non-crop progeny (weeds, etc) due to a negative selection pressure; and 3) Individuals bearing even mildly harmful TM traits will be kept at exceedingly low frequencies in weed populations because weeds typically have a very high seed output and strongly compete amongst themselves, eliminating even marginally unfit individuals (Gressel, J. 1999: Tandem constructs: preventing the rise of superweeds. Trends Biotech. 17: 361-366).

Figure 10:
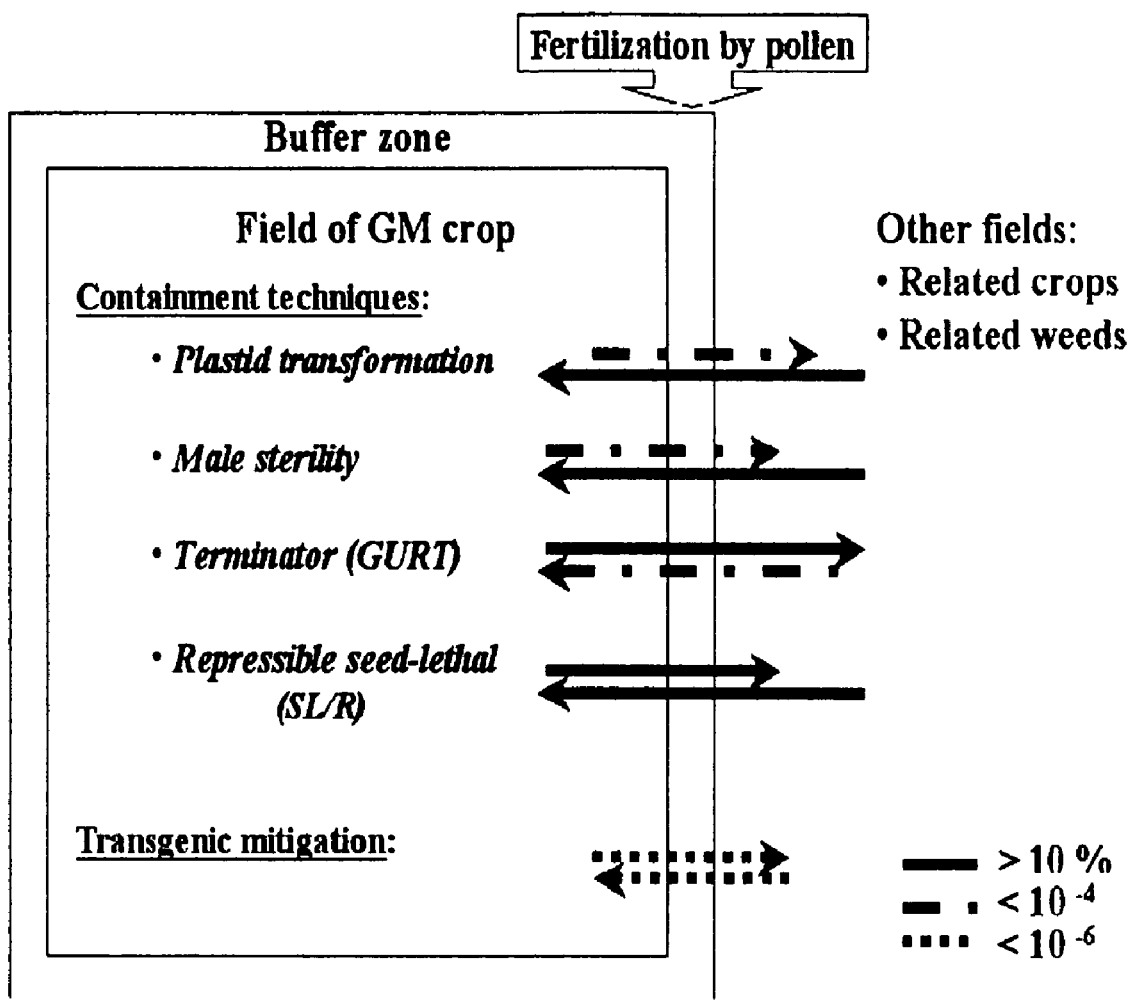
FIG. 10 is a schematic illustrating the efficacy of mitigation strategies vs. containment strategies. Note the difference of orders of magnitude between projected frequencies of "leakage" with containment strategies and the low frequency of introgression events with TM mitigation.

Thus, if the primary gene of agricultural advantage being engineered into a crop is flanked by TM gene(s), such as dwarfing, uniform seed ripening, non-shattering, anti-secondary dormancy, or non-bolting genes in a tandem construct, the overall effect would be deleterious after introgression into weeds, because the TM genes will reduce the competitive ability of the rare transgenic hybrids so that they cannot compete and persist in easily noticeable frequencies in agroecosystems (Gressel, J. 1999: Tandem constructs: preventing the rise of superweeds. Trends Biotech. 17: 361-366). Weeds are usually copious pollen producers and set large numbers of seeds, many of which germinate during the following season. Thus there is strong competition, and pollen or seeds bearing TM constructs are bound to be competed to a very low frequency in the population as illustrated in FIG. 10:

One TM trait has already been introduced into transgenic crops, albeit inadvertently: the use of the 35S promoter in gene constructs of desirous traits in oilseed rape (*Brassica*

*napus*). The 35S promoter was originally derived from cauliflower mosaic virus (CaMV). This promoter is silenced in plants infected by the virus (Al-Kaff et al., 1998)—i.e., most cruciferous weed plants in the wild. Thus, a wild and weedy related *Brassica* that introgresses herbicide resistance from oilseed rape is suddenly herbicide sensitive in a CaMV-infected weed. One could consider the advertent use of such promoters.

Other TM traits that could be used are best visualized when observing the individual differences between crops and weeds. This is best illustrated with the examples of: (i) rice and weedy red rice (both *Oryza sativa*) as well as rice with wild rices Oryza spp.; (ii) oilseed rape (*Brassica napus*) and feral and weedy Polish rape/wild radish *B. campestris=B. rapa*, (iii) sugar beets (*B. vulgaris*) and weed beets (sea beets) and (iv) corn and maize, as summarized below.

TM Traits Which are Available as Gene Sequences

Some of the traits suggested for use as TM genes have been characterized as sequenced genes. Others are known to exist as named traits that are inherited, and yet others have been mapped as genes to positions on various chromosomes. Thus, not all TM traits are as yet available for insertion in tandem constructs. However, as in the case of dwarf or semi-dwarf phenotype, there can be many different ways for a plant to confer a TM trait, and thus, more than one gene can be used as a mitigator gene. Further, various well known methods for screening and gene identification are readily available to one of ordinary skill in the art, such that genes for transformation can be rapidly sought and found, especially with the availability of transposon tagging as a method for such screening and searching.

An interim solution may be to select transformants that have randomly introgressed the primary gene to a point in close linkage to a TM trait. Many of these TM traits are already mapped in major crops, such as dormancy in rice (Wan et al, 1998; Lin et al., 1998). The closer the linkage distance, the lesser the likelihood of segregation. Using technologies for site specific insertion of genes into chromosomes, the primary desirable genes could be spliced close to TM genes, without having to know the sequence of the TM gene.

Seed dormancy: Weed seeds typically have secondary dormancy with seeds from one harvest germinating bit by bit throughout the following season, and over a number of years (Vleeshouwers et al., 1995). This evolutionary trait is considered to be a risk-spreading strategy for weeds and wild species that maximizes fitness while reducing losses due to sib competition (Hyatt and Evans, 1998; Lundberg et al., 1996). Staggered secondary dormancy prevents all the weeds from being controlled by tillage before the crop is planted, or controlled by tillage or herbicides during crop rotation. Rare mutants lacking secondary dormancy were selectively propagated during crop domestication, as the loss of secondary dormancy is desirable to the farmer, who wants uniform germination after planting the crop. Crop seed that germinates uniformly after planting gives a uniform harvest. This can well be seen when comparing crops with their weedy progenitors and relatives (Ling-Hwa, 1997). Seed dormancy is closely associated with the control of gibberellic acid (GA), and signal modifiers associated with alpha amylase expression. Recently, Zentalla et al (The Plant Cell, 2002; 14:2289-2301) reported successful abolition of dormancy with RNAi constructs comprising sequences of SLN1, a repressor of GA action. Additional dormancy regulatory factors can be genetically modified, as i the abolition of dormancy by overexpression of the RGL2 gene in *Arabidopsis*(Lee, et al, Genes and Development, 2002; 16:416-58). Secondary dormancy is also related to abscissic acid. Thus, for example, second dormancy can be prevented by an anti-sense construct including a gene or sequence of the abscissic acid biosynthesis or signal recognition pathway, such as the AREB 1-3 elements (GenBank accession Nos. AB01760, AB01761, and AB01762, respectively) (see Finkelstein et al The Plant Cell, 2002;14S:s15-s45). Genetically abolishing secondary dormancy would be neutral to the crop, but deleterious to the weed. Tillage, crop rotation, and preplant use of herbicides, all standard practices would control the uniformly-germinating weed seeds lacking secondary dormancy during the following season.

Ripening and shattering: Physiologically, one way to avoid seed shattering is to have uniform ripening. Early maturing soybean and oilseed rape seeds on indeterminate continuously flowering varieties typically shatter. Thus, determinacy, with its single uniform flush of flowering is one method to prevent shattering, but this often shortens the season, reducing yield. The hormonology of the abscission zone controls whether shattering will occur and it is possible that if cytokinins are overproduced, then shattering will be delayed. In sorghum the genes that control shattering seem to be on QTLs (Paterson et al., 1995) as discussed above.

Weeds disperse their seed over a period of time and much of the ripe seed "shatters" to the ground. This ensures replenishment of the soil seed bank. A proportion of the weed seed is harvested with crop seed, contaminating crop seed, facilitating weed dispersal to wherever the crop seed will be grown. Weeds have evolved morphological and phenological "mimicries" to the crop seed (Barrett, 1983; Gould, 1991) necessitating continual evolution and refinement of seed cleaning techniques to remove the contaminating weed seed. Crop varieties have been selected for non-shattering, but recently domesticated crops such as oilseed rape still suffer from shattering (Simon, 1994; Prakash, 1988; Price et al., 1996). The first problem in domestication is control of shattering (Young, 1991; Levy, 1985). In addition to the loss of yield, the shattering of crop seed causes the crop to be a volunteer weed in the following crop (Lutman, 1993).

Uniform ripening and anti-shattering genes would confer a negative trait for the weeds, would be neutral for rice (because it ripens uniformly and does not shatter easily after thousands of years of selection), and positive for oilseed rape, which still has a shattering problem. The addition of anti-shattering genes such as the shatterproof gene of *Brassica* (GenBank Accession No. AAK00646) in a TM construct could also prevent cultivated oil seed rape from becoming a volunteer weed problem as well as being a TM gene. Crop seed contaminated with low levels of weed seed are typically used for feeding or processing, only weed free "certified" seed is sown.

Dwarfing: Vertical deprivation (dwarfing) has proven itself as a desirable trait in crops due to the increase in harvest index by virtue of having less stem and more seed. Many genes are known, via their physiological role, that control height.

Dwarfing has been especially valuable in generating "green revolution" crops, but also has value in normal cropping situations. The green revolution in rice and wheat is based on a modification of the harvest index, the ratio of grain to straw. For millennia these crops had been selected for height, to outgrow weeds, limiting the photosynthate available for grain. Weed evolution continued apace, giving rise to taller weeds. The advent of selective herbicides to kill weeds allowed for genetic dwarfing of these crops resulting in more seed harvest and less straw. Some of these dwarfing genes are tightly linked to genes reducing general yield potential. Still, the lowering of height, precluding the concomitant problem of tall plants "lodging" (falling over), and increased yield, especially after fertilizer use (which previously promoted lodging), allowed countries like India to become self sufficient, despite population increase.

Various new systems of genetically engineered height reduction are being introduced. These include genes relating to hormone production (Azpiroz et al., 1998; Schaller et al., 1998), such as mutants of the GAI gene from *Arabidopsis*, and Os-GRF1 from rice (GenBank Accession No. AF201895), as well as those dealing with shade avoidance. Much of stem elongation is in response to shading. This is advantageous when competing with other species, but not in a weed-free crop stand where only siblings are competing. The overexpression of specific phytochrome genes, such as the phytochrome B gene of *Arabidopis* (GenBank Accession No. AY466496) prevents recognition of shading and thus the plant remains short (Robson et al., 1996). This is advantageous for a crop and could also be used where the present dwarfing genes prevent obtaining the highest yields. This trait would be disadvantageous for a weed that must compete with the crops; it would be shaded over by the crop.

Gibberellins: It is well known that preventing the biosyntheses of gibberellins reduces the height. The genetic relationships between some dwarfing genes and gibberellin biosyntheses has been elucidated (Webb et al., 1998). This is the basis of many chemical dwarfing agents used commercially to lower stature and prevent lodging of wheat. The enzymes and genes controlling various steps in gibberellin biosyntheses are also known. Copalyl diphosphate synthase, ent-kaurene synthase, and ent-kaurene oxidase are responsible for early stages in the biosynthesis of all gibberellins (Smith et al., 1998; Yamaguchi et al., 1998, Hedden and Kamiya, 1997; Lange, 1998; Helliwell et al., 1998). *Arabidopsis* mutations bearing mutations in any of them are dwarfed, with the dwarfing being reversible by gibberellin treatment. Overexpression of a gene coding for ent-kaurene synthase, causing co-suppression mimicked the mutant phenotype.

Some processes, such as flower stalk bolting, are controlled by specific gibberellins; in radish, $GA_1$ and $GA_4$ are responsible for flower stalk bolting (Nishijima et al., 1998). It may be necessary to characterize the genes coding for the monooxygenases and dioxygenases that are responsible for these later steps (Hedden, 1997). Some of these genes have been isolated as well (Kusaba et al., 1998).

Brassinosteroids: This new group of hormones also causes elongation of stems in many plant species, and their absence results in dwarf plants. A 22 α-hydroxylase cytochrome P450 (GenBank Accession No. AF 044216) has recently been isolated that controls a series of these steps in brassinosteroid biosynthesis (Choe et al., 1998), and plants missing the enzyme are dwarfed (Azpiroz et al., 1998). Additionally, suppressive overexpression of a sterol C24-methyl transferase (GenBank Accession Nos. BT 002093 and AY 128389) also causes dwarfing (Schaller et al., 1998). Methods for genetic modification of brassinosteroid signaling in plants, using the phyB gene, are taught in, for example, U.S. Pat. No. 6,534,313 to Neff et al, which is incorporated herein by reference).

Shade avoidance: Various forms of the pigment phytochrome interact to detect whether a plant is being shaded (Smith and Whitelam, 1997; Devlin et al., 1998, Devlin et al Plant Physiol 1999;119:909-16; Torii et al., 1998; Auckerman et al., 1997). Phytochrome recognition of shading (red/far red light ratios) leads to stem elongation, which is unneeded in a weed-free crop. The engineering of suppressive overexpression constructs of one of the phytochromes led to plants that did not elongate as a results of shading (Robson et al., 1996).

Much of the gene isolation has been from *Arabidopsis*, such as the elm1 and phyB genes (Reed, et al Plant Physiol, 2000; 122:1149-60) yet in the transgenic plants the suppressive overexpression was active in dwarfing tobacco. Methods for genetic manipulation of the elf3 and similar genes are well known in the art (see, for example, U.S. Pat. No. 6,002,069 to Yanofsky, which is incorporated herein by reference).

QTLs: QTLs or other unidentified genes that have been shown to provide general weediness characters are known (Paterson et al., 1995). QTLs have also been identified controlling dormancy (Van der Schaar et al, 1997) and for the late stages of gibberellin biosyntheses (Lange et al., 1997), which might relate to stem dwarfing or seed stalk bolting.

Other TM traits: One could envision other mitigating genetic traits that would be disadvantageous to weeds but neutral to crops. These include modifying or eliminating seed coat characters that allow weed seeds to pass through animal digestive tracks intact and then be dispersed. Genes that promote root storage would be advantageous to cultivated beets but detrimental to annual wild beets. Genes that prevent bolting (i.e., promote biennial growth) would be excellent for carrots, celery, cabbage, lettuce, beets, and related crops, but would be highly deleterious to related weeds. Anti-flowering genes would prevent introgression of genes from potatoes into wild Andean relatives (the only place where hazards of introgression from potatoes exist to weeds). They would also prevent volunteer potatoes arising from true seed, where this is a problem. Sorghum provides an interesting case. Crosses between cultivated sorghum (*S. bicolor*) and johnsongrass (*S. halapense*) gave rise to sterile, perennial, vegetatively-propagating plants (Baker, 1991). The hybrids have thick rhizomes storing large amounts of material. Various of the QTL's reported by Peterson et al (1995) could severely decrease the fitness of any hybrids that form.

Presumably, comparisons of crop traits with weed traits will lead to finding other mitigator genes useful in the tandem TM constructs of the present invention.

Of particular interest is the method of altering plant biochemical/morphological/physiological characteristics by selective expression and/or overexpression of a cytokinin degradation control proposed by Schmulling et al (U.S. Patent Publication No. 20030074698, which is incorporated herein by reference).

TMs for vegetatively propagated crops: The genes for pollen sterility (Williams, 1995) would clearly be the simplest way to render potato or trees to be without true seeds. Such potatoes could not become volunteer weeds (from true seeds), or have pollen that introgresses into other potato varieties or into wild related Andean species (Love, 1994; Eijlander and Steikema, 1994).

TMs for biennial crops: Biennial crops such as beets, carrots, etc. usually require a period of cold vernalization before flower stalk formation (bolting). At the end of the vernalization there is typically a burst of endogenous gibberellin biosynthesis, which induces stalk elongation, and exogenous gibberellins can often replace the cold requirement. Possibly, bolting could be suppressed by including a TM RNAi antisense or suppressive overexpression construct for one of the enzymes of gibberellin biosynthesis, both on crop and of related weed, especially if the RNAi anti-sense or over-expressed trait is under the control of a seed stalk specific promoter. These genes are well known in the art (see above).

Balancing Desirous Transgenic Traits with TM Traits

There is considerable debate about the advantages that would accrue to weeds from the primary transgenic traits. Resistance by modified site of the herbicide binding site to its target should only confer an advantage when the specific herbicide is used. It is unknown whether there would be pleiotropic advantages of herbicide resistance due to introducing genes for metabolic inactivation of herbicides. Insect, or pathogen resistances would clearly provide an advantage to a weed, if the weed does not already have these resistances, and is affected by the pest. Many pest resistances were bred out of wild species during domestication; the endogenous chemicals weeds use to alleviate pest problems often taste bad or are toxic to mammals.

Still, let us assume that the primary desirable transgenic trait confers an advantage to a weed; how much will TM traits actually mitigate that advantage? Weeds are not only highly competitive with crops, they are competitive with weeds of other species as well as within their own species. Seed-producing weeds often produce thousands of seeds, in steady state conditions, to replace a single plant, suggesting extreme competition to be the replacement; the selection for high competitive fitness is intense. This has dual implications in the discussed situation. A weed that introgresses any advantageous transgenic trait, will proliferate and spread though a population very quickly, even if it has fitness advantage that is only marginally positive (Thill and Mallory-Smith, 1997; Crawford et al., 1997). Conversely, one can balance the disadvantage of TM traits against the advantage of the primary trait. This must be done in both in the presence and absence of the reason for using the primary trait. The primary trait only provides an advantage when it is needed; when there is pressure from the pest, herbicide, or stress. Some primary traits that were not intended to confer any plant protective advantage to the crop might still do so when introgressed into a weed, e.g., changed oil or starch composition. Membrane lipid compositions do change in response to temperature and other stresses, and the ability to adapt to certain environments might be enhanced or decreased (Cooper and Raybould, 1997; Linder, 1998); a plant with a modified starch might be less palatable to insects or less digestible by fungi, and thus have an advantage. In the absence of the selection pressure making expression of the primary trait desirable, such a primary trait should not confer any advantage, accentuating the utility of the TM traits. Indeed, when the primary selector is not present, the primary transgenic trait can be disadvantageous; this has been demonstrated with one herbicide resistance gene (Bergelson et al, 1996). Many herbicides have a short residual effect and when they are not present, there is no advantage to having transgenic herbicide resistance. Similarly, while some insect pests disease pathogens are continually present, there are many others that appear in damaging levels only in certain seasons, or even only once every few years, when the climatic conditions are just right for their causing pandemics. If resistance to a disease or insect has only occasional value, and the resistance mechanism carries a "fitness penalty" in the absence of appropriate selection pressure, the value of the primary gene is depleted, and TM genes will confer a net decrease in fitness.

As used herein the phrase "commercially desirable genetic trait" refers to any inheritable trait that confers an advantage or increased value to a commercially cultivated crop, while the phrase "mitigating genetic trait" refers to any inheritable trait which is deleterious when expressed in an undesirable, interbreeding species (weed) of the commercially cultivated crop, but is benign or advantageous when expressed in the commercially cultivated crop. In most cases requiring mitigation of the effects of "leakage" of genetically engineered traits from cultivated crops to weeds, genes for specific traits can be readily categorized as either "commercially desirable" or "mitigating" in character. However, it is conceivable that in some cases, candidate genetic traits can be categorized as being both "commercially desirable" and "mitigating" traits, although such dual categorization can only occur when the identity and character of the crop targeted for genetic manipulation, and the significant weedy varieties thereof are unknown. Since when applying the present method the identities, and respective characters of the cultivated crop plant and its undesirable, interbreeding species (weed) are known, an ordinary skilled artisan would be more than capable of selecting the appropriate mitigating genetic trait to be utilized in tandem expression with the commercially desirable genetic trait in transforming the crop plant of interest to produce a cultivated crop capable of mitigating the effects of introgression of the commercially desirable genetically engineered primary trait. Specific examples of such commercially desirable and mitigating traits are provided herein.

Likelihood of TM Genes Segregating from Advantageous Genes

Often, the expression of one gene of a tandem construct is lost in the primary transgenic plant, and sometimes the expression is lost after a few generations. The reasons for these losses are not always clear nor relevant for this discussion, as only stabilized progeny of transformants are released to agriculture. If all traits of a tandem construct are co-expressed after 4-5 generations of development, it is fair to consider such a tandem gene pair as stable, i.e., as stable as any native, tightly-linked adjacent genes. The likelihood of the TM mitigator trait and desired, primary trait segregating from each other is infinitesimally lower than for the TM trait being inactivated by a mutation. Thus, if the mutation frequency of inactivation of the TM gene is $10^{-6}$ to $10^{-7}$, that would be the frequency of the loss of the TM trait as the frequency of crossing over is many orders of magnitude lower. In the rare cases wherein the frequency of crossing over of tightly linked traits presents an unacceptably high risk, then one can consider using two TM genes, flanking the primary gene on either side. The frequency of loss of two mitigator genes once stably transformed can be predicted as $10^{-12}$ to $10^{-14}$. Each TM trait should work in a balance with the primary trait, and where the primary gene gives a strong advantage to a weed, it might be necessary to have more than one TM trait in a construct. The risk of losing a TM mitigator trait can be further decreased by combination with a cytogenetic failsafe, where it is available. If the tandem construct is located on a non-homologous chromosome (where such exist), then only rare homologous recombination can move it. As there is no selective advantage to losing the TM mitigator trait on the non-homologous chromosome, one can compound the frequency of likelihood of homologous recombination with the frequency of loss of the TM trait(s).

Do TM genes have to give 100% safety: No risk situations are completely impossible but how low a risk do we need to attain? This is really a question for regulators, but when they do deliberate the issue they must ask; when will the related weed evolve the trait in question by natural means. This is best illustrated by an example: one company in the United states engineered resistance of ALS (acetolactate synthase)—inhibiting herbicides into sunflowers (*Helianthus annuus*) but never even field tested them, because of fear that the gene might introgress into weedy wild sunflowers (also *H. annuus*), prevalent in the mid western plain states. Natural introgressions between this crop and related weed are common and cause problems (Arias and Riesenberg, 1994; Whitton et al., 1995). The mutations conferring resistance to ALS-inhibiting herbicides are naturally prevalent in plant populations in a frequency of one in a million, and ALS-inhibiting herbicides are widely used. Wild sunflowers have recently evolved resistance to ALS-inhibiting herbicides in monoculture cropping (White et al., 1998). If a TM construct had been inserted in tandem with an ALS gene, with a likelihood of segregating of $10^{-10}$, then the likelihood of getting ALS-resistant wild sunflowers would not have appreciably been changed by introgression from transgenics. Wild sunflowers could have been controlled in sunflower fields, lessening the possibilities of natural introgressions. Such analyses should be made wherever possible.

Table 4 below provides examples of such TM tandem constructs applicable to the mitigation of introgression of a number of primary transgenes and phenotypes. Specific examples of the efficient use of such Transgenic Mitigation are presented in the Examples section herein below.

TABLE 4

Primary traits field tested for major crops requiring containment and mitigation, and suitable mitigators. (Note secondary advantages to primary crops).

| Crop[a] | Primary transgenes[a] | Main introgressional problems | Mitigator genes |
|---|---|---|---|
| Oilseed rape | pharmaceuticals | *Brassica* weeds, | Δ*gai* |
| | herbicide resistance | other oilseed rape, | anti-gibberellic acid pathway |
| | | volunteer problems | antishattering |
| | disease resistance | | |
| | insect resistance | | anti-brassinosteroids |
| | improved quality | | |
| Secondary advantages of mitigators to crop: higher yields; less shattering | | | |
| Sugar beet (Carrot/root crops) | herbicide resistance | Feral and wild beets (wild carrot) | antibolting, reversible male sterility |
| | disease resistance | | |
| | insect resistance | | |
| Secondary advantages of mitigators to crop: no premature crop bolting in adverse conditions | | | |
| turf grass | herbicide resistance | related weeds | Δ*gai*/pollen promoter |
| | disease resistance | anti-GMO neighbors | gibberellic acid pathway |
| | insect resistance | | |
| Secondary advantages of mitigators to crop: no allergenic pollen, less cutting | | | |
| Corn | herbicide resistance | | |
| | disease resistance | | |
| | insect resistance | | |
| | agronomic properties | | |
| | nutritional quality | | |
| | polymers | | |
| | pharmaceuticals | | Shrunken endosperm genes |
| Secondary advantages of mitigators to pharmaceutical crop: easier product extraction | | | |
| Rice | herbicide resistance | red (feral) rice | anti-gibberellic acid pathway |
| | disease resistance | anti-shattering | |
| | insect resistance | | |
| | pharmaceuticals | | |
| Secondary advantages of mitigators to crop: can dwarf tall, non green-revolution high quality varieties such as "Basmati", where flavor is polygenic, with increased "green revolution" type yield | | | |
| Poplar | herbicide resistance | native poplars | *barnase*/ tapetum promoter |
| (Pine) | disease resistance | (native pines) | female sterility |
| | insect resistance | | |
| | decreased lignin | | |
| | increase cellulose | | |
| Secondary of mitigators advantages; higher yields; no allergenic pollen | | | |

[a]Source: USDA-APHIS website.

Example 1

Transgenic Litigation of Introgression of Herbicide Resistance by the Dwarfing Δgai Gene in Tobacco One of the traits suitable for Transgenic Mitigation in constructs with a primary, desirable trait is dwarfing, which is caused by the well characterized Δgai gene (such as GenBank Accession No. AY142002, from *Arabidopsis*). While dwarfing is desirable in many crops, preventing lodging and producing less straw with greater yield, dwarfing would be disadvantageous to the rare weeds introgressing the TM construct, as these hybrids could no longer compete with other crops or with fellow weeds. In order to determine whether co-transformation of a desirable transgene with a mitigator gene would prevent proliferation of hybrids having the primary trait in the case of breach of containment, a tandem construct was made containing an ahas$^R$ (acetohydroxy acid synthase) gene (GenBank Accession No. X51514) for herbicide resistance as the primary desirable gene, and the dwarfing Δgai (gibberellic acid-insensitive) mutant gene as a mitigator, and used to transform tobacco (*Nicotiana tabacum*).

Experimental Procedures

Assembling the Tandem Construct

The genes: The genomic ahas$^R$ gene cloned in the pAC456 plasmid was kindly provided by Dr. Roy Chaleff, American Cyanamid Co. It contains the *Arabidopsis thaliana* ahas promoter, ahas$^R$ coding sequence and ahas terminator. The genomic Δgai gene cloned in pλg/SK+ plasmid containing the *A. thaliana* gai promoter, Δgai coding sequence and gai terminator, was kindly provided by Drs. Donald Richards and Nick Harberd, Dept. of Molecular Genetics, John Innes Centre, Norwich, UK. The two complete genes were used to assemble the TM tandem construct. The complete sequences of both clones were determined by sequencing different critical DNA segments within both genes, using an ABI Prism 3700 sequencer. Similarity alignments with BLAST genomic database of *A. thaliana* chromosome 3 (from nucleotide 35,863 to nucleotide 41,580 of the GenBank accession AL133315), showed that the mutated ahas$^R$ is identical to the *Arabidopsis* csr1.2 gene (GenBank accession X51514) containing a substitution of serine at amino acid residue 653 with asparagine (Sathasivan K, Haughn G W, Murai N (1990) *Nucleic Acids Research* 18, 2188-2188) Sequenced segments of Δgai aligned with the database of *A. thaliana* chromosome 1 from nucleotide 115,566 to nucleotide 120,773 of the GenBank accession AC006917. The Δgai was oriented with the gai promoter close to the XbaI site, and the gai terminator close to the EcoRI site of the pλg/SK+ vector.

pPZP212-ahas$^R$-Δgai-1 tandem construct (TM 1): The 5,712 base pairs (bp) XbaI ahas$^R$ fragment was isolated from the pAC456 plasmid and cloned in both orientations into the XbaI site that is 15 bp upstream of the Δgai gene of the pλg/SK+ plasmid. Both genes were in direct orientation in the pSK+-ahas$^R$-Δgai-1 clone as confirmed by sequencing analysis using the universal T3 and T7 primers. The pSK+-ahas$^R$-Δgai-1 clone was first digested with NotI. Klenow polymerase was used to blunt the 3' NotI sticky end and SalI was then used to release the complete ahas$^R$-Δgai-1 fragment. This fragment was ligated into the SmaI and SalI predigested binary vector pPZP212 (Hajdukiewicz P, Svab Z, Maliga P (1994) Plant Molecular Biology 25, 989-994) to produce the pPZP212-ahas$^R$-Δgai-1 (TM 1) plasmid (FIGS. 3a,c). The TM plasmid contained the aadA gene conferring bacterial resistance to spectinomycin, and the kan gene encoding neomycin phosphotransferase II (NPTII), conferring plant resistance to kanamycin. Both selectable genes were carried within the native T-DNA of the pPZP212 binary vector (Hajdukiewicz P, Svab Z, Maliga P (1994). Plant Molecular Biology 25, 989-994). The TM 1 plasmid was partially sequenced to confirm the makeup of the TM 1 construct, which was consistent with the KpnI/SalI enzymatic digestion of the TM 1 construct (FIG. 3d).

Tobacco transformation: The TM 1 construct was electroporated into *Agrobacterium tumefaciens* strain EHA 105, which was used to transform *Nicotiana tabacum* cv. Samsun NN leaf disks, as described in Horsch et al (*Science* 1985; 227, 1229-1231). Primary transgenic plants were transferred to soil and pollinated by wild type *N. tabacum* cv. Samsun NN. Segregating seeds of TM $T_0$ (=BC) plants were collected for genetic analysis and for the competition experiments. The 1:1 (hybrid to wild type) segregating population precluded the need to further mix transgenic with wild type seed.

Gene Integration Analyses of Tobacco Transformants

Leaf callus-inducing assay: Axenic young leaves from regenerated wild type and putative primary TM transformants were cut and placed on MS callus-inducing medium (Murashige T, Skoog F (1962) *Physiologia Plantarum* 15, 473-497) in different petri-dishes containing 0.2 μg mL$^{-1}$ 2,4-D and various concentrations of imazapyr to verify resistance. All treatments were repeated twice. The fresh weight of the calli that developed on each leaf cutting was measured after 3 weeks.

Polymerase chain reaction (PCR): Total plant genomic DNA was prepared by the cetyltrimethylammonium bromide (CTAB) method of Rogers and Bendich (Rogers S O, Bendich A J (1994) Extraction of total cellular DNA from plants, algae and fungi. In: *Plant Molecular Biology Manual* (eds Gelvin S B, Schilperoort R A), pp. D1:1-8. Kluwer Academic Publishers, Belgium), or by the Puregene® kit for genomic DNA purification (Gentra Systems, Minneapolis, Minn., USA) using leaf discs of primary semi-dwarf and imazapyr-resistant tobacco transformants. The DNA was analyzed by PCR for the presence of intact tandemly linked ahas$^R$ and Δgai genomic insert. Four different DNA segments within the genomic TM T-DNA insert were amplified over the positions indicated in FIG. 3a: Segment A at the right border of T-DNA and the beginning of the ahas promoter [forward primer 5'-GCTTTACACTTTATGCTTCC-3' (SEQ ID NO: 1)—reverse primer 5'-TAACACTTTTTCTTTTTTTG-3' (SEQ ID NO: 2]; Segment B at the end of the ahas terminator and over the 15 bp linker between the ahas$^R$ and into the Δgai gene, and the beginning of the gai promoter [forward primer 5'-GGTTATGATGGCAGGATGTGG-3' (SEQ ID NO: 3)—reverse primer 5'-CGTTACATCATTTTCTCACAA-3' (SEQ ID NO: 4)]; Segment C of the Δgai-DELLA deletion region [forward primer 5'-TAGAAGTGGTAGTGGAGTGA-3' (SEQ ID NO:5)—reverse primer 5'-CGACGGAGAGAGACGG-TAAA-3' (SEQ ID NO: 6)]; Segment D, the kan gene located at the left border of the T-DNA [forward primer: 5'-TCATTTCATTTGGAGAGGAC-3' (SEQ ID NO: 7) and reverse primer: 5'-CATGATATTCGGCAAGCAGG-3' (SEQ ID NO: 8)]. PCR reactions were carried out in 50 μL aliquots containing about 200 ng genomic DNA, 5 μL of 10×DyNAzyme™ II buffer (Finnzymes Oy, ESPOO, Finland), 1.5 U of DyNAzyme™ II DNA polymerase (Finnzymes Oy, ESPOO, Finland), 5 μL of 2.5 mM of each dNTP(s) (Roche Diagnostics, GmbH), and 35 pmol of each primer, in sterile distilled water. The mixture was denatured for 3 min at 94° C. and amplified for 35 cycles (94° C. for 30 s, 51° C. (DNA segments A and C) or 57° C. (segments B and D) for 30 s, 72° C. for 1 min) with a final cycle of 7 min at 72° C. The PCR products (15 μL) were loaded directly onto 1% (w/v) agarose gels to verify single bands. The remaining PCR products were purified using the QIAquick PCR Purification Kit® (Qiagen, Hilden, Germany) according to the manufacturer's instructions, and sequenced to confirm the integration of the TM T-DNA.

In vivo AHAS enzyme assay: A rapid leaf-disc AHAS microtiter plate assay described by D. Shaner [Shaner, 2002and pers. comm.] was used to measure tobacco AHAS resistance to imazapyr. Briefly, triplicate 4 mm diameter leaf discs were taken from parallel positions on both sides of the midrib from young leaves of each plant, and floated on 100 μL volumes of 10% (w/v) MS salts (Duchefa Biochimie, Haarlem, Neiderlande) to which were added: 10 mM $KH_2PO_4$, 1% (w/v) L-alanine and 500 μL 1,1-cyclopropanedicarboxylic acid (CPCA; Sigma-Aldrich, St Louis, Mo., USA), one disc in medium with 5 μL imazapyr and the other without. The lowest imazapyr dose inhibitory to AHAS in the untransformed leaves (0.5 μL) was determined (data not shown). The samples in the plates were placed under 85 $\mu E\ m^{-2}s^{-1}$ fluorescent lighting for 8 h at room temperature, and stored overnight at –20° C. After thawing, 25 μL of 5% (v/v) $H_2SO_4$ were added to each well and incubated at 60° C. for 15 min to terminate the enzymatic reaction and complete the chemical conversion of acetolactate to acetoin. Then, 150 μL of 2.5% (w/v) α-naphthol (Fluka, Switzerland) and 0.25% (w/v) creatine (Fluka, Switzerland) in 2 N NaOH were added to each sample and the plates were incubated in the dark at 60 ° C. for another 15 min to accelerate red color development in the solution surrounding discs from imazapyr resistant plants. The concentration of acetoin-naphthol-creatin complex was determined spectrophotometrically at $A_{530}$, and the AHAS activity was presented as percent activity in the absence of the herbicide. Total soluble proteins were determined from untreated leaf tissues by the method of Bradford.

Inheritance of the TM Construct Transgenes

Seed germination in the presence of kanamycin or imazapyr: A discriminatory dose level of Nitsch (Nitsch JP (1969) *Phytomorphology* 19, 389-404) agar medium containing 85.8 μM kanamycin or 0.3 μM imazapyr inhibiting the growth of non-transformed plants was determined. Surface sterilized seeds of wild type, the backcross of primary transformants with wild type $T_0$ (=BC), $T_1$, $T_2$, and $T_3$ tobacco plants were planted on either medium. Sensitive seedlings were identified as those that stopped growing within 10 days, forming only short roots and cotyledons, while resistant seedlings grew well, forming long roots and true leaves, continuing their growth past 10 days. The segregation ratio of wild type to TM of each line was calculated. Resistant/dwarfed seedlings were grown to maturity in soil and the plants were analyzed for AHAS resistance (phenotype) and for $ahas^R$ and Δgai insert by PCR (genotype), as described herein above.

Chlorophyll measurement: Chlorophyll was extracted from ten 8 mm diameter leaf disks from four leaves per plant using the 80% acetone method of Porra et al. (*Biochimica et Biophysica Acta* 1989; 975: 384-394). The absorbance of the supernatant was spectrophotometrically measured at 470, 646.6, and 663.6 nm, using the 80% acetone buffer as a blank. Chlorophyll a and b were determined using the equations in Porra et al. (*Biochimica et Biophysica Acta* 1989; 975: 384-394), and carotenoid using the equations in Hill etal. (*Bioscience Reports* 1985; 5: 775-781).

Productivity of tobacco transformants without self competition: Several growth parameters were determined at intervals on wild type and TM transgenic plants grown separately in 13 cm diameter 1 L pots filled with a 1:1:1 mixture of peat, crushed tuff rock, and loam and spaced 40 cm between pots such that the canopies never overlapped. Growth parameters included: plant height, number of leaves, number of opened flowers, stem thickness measured at maturity at 5 cm above soil, and leaf internode spacing measured from the first basal leaf toward the apical branches carrying flowers and flower buds. Leaf longevity was measured by recording whether each leaf was green vs. yellow or dried at each internode at various times and calculating the $t_{0.5}$ of the leaves. The fresh weights of the shoots and roots were separately measured at maturity.

Competition of TM transgenics with the wild type, and self competition of each alone: The transgenic TM tobacco was used to simulate a TM introgressed hybrid or transgenic volunteer crop, and the wild type tobacco was used to simulate a non-transgenic crop, weed, or wild plant. The competitive interactions between the transgenic and wild type plants were assessed in two separate internally replicated greenhouse experiments. In both experiments, seeds obtained from the first backcross $T_1$ (=$BC_1$) of a representative TM line $T_1$-7 (pollen recipient) and wild type (pollen donor) were used to grow mixed TM and wild type cultures. The segregation ratio of the TM linked genes in the backcross was 1:1 hemizygous TM to wild type, as confirmed by seed selection on a medium containing the lowest discriminatory dose of imazapyr (0.3 μM) that killed the wild type segregants, but did not affect the development of the resistant plants. Randomly chosen $T_2$ (=$BC_2$) segregating nursery seedlings were transplanted at 2.5-, 5- and 10-cm spacing (experiment I), or at 1-, 2.5-, and 5-cm spacing (experiment II), without using the selective herbicide. The experiments were conducted in 55×41×22 cm plastic containers filled with a mixture of peat, crushed tuff rock, and loam (1:1:1). Monoculture controls of wild type alone (seeds obtained from pure wild type line), and TM alone ($T_2$ =$BC_2$) seedlings pre-selected with 0.3 μM imazapyr medium to cull the wild type segregants were also grown at the same spacing. Plants were grown under ambient greenhouse light, 30±3° C., with a higher light intensity in the first experiment than that in the second one (780±50.3 and 474±17.2 $\mu E\ m^{-2}s^{-1}$, respectively). Light intensities are the averages (±SE) of noontime measurements made on seven occasions during the growing season. All the replicates were randomly placed on glasshouse benches to minimize microenvironmental effects. Optimal water was supplied, and all plants were treated against diseases and arthropods when necessary. The young putative-TM, phenotypically dwarf plants were assayed for resistant AHAS enzyme activity by the leaf disc test (as described above). All resistant transgenic plants had more compact canopies and darker green leaves than the wild type. After AHAS enzyme screening, the plants were labeled with a numbered tape attached to the stem for future reference. The leaf discs of the taller less-compact plants all contained herbicide susceptible AHAS.

Two months after transplanting and at time intervals thereafter, various growth parameters were measured at the different spacings including: plant height and live leaf number of 10-15 randomly chosen plants of each biotype in each box. The number of flowers formed per each plant, and the number of surviving plants of each biotype were also recorded. The vegetative fitness (based on plant height) and the reproductive fitness (based on flower and fruit number formed per $m^2$) of TM plants relative to wild type, were calculated at the different spacings and time intervals as a TM/wild type ratio. The below-ground competition was not measured in our experiments due to extreme root intertwining at the close spacing, however, it was assumed that below-ground competition would manifest itself in above ground growth parameters.

Statistical analyses: Tandem trait segregation data were statistically analyzed by the chi-square test. The chlorophyll content and the tobacco productivity and fitness data were analyzed using the JMP® program (version 4.0.1; SAS Institute 2000) by one-way analysis of variance (ANOVA) and comparison of the least significant differences (LSD). Differences were considered to be statistically insignificant at $P>0.05$.

Results

Expression of the TM construct in tobacco transformants: Seven independent primary semi-dwarf, kanamycin and imazapyr-resistant tobacco lines were obtained by transformation with the TM 1 construct (pPZP212-ahas$^R$Δgai-1) (FIG. 1). All the $T_0$ lines had similar semi-dwarf phenotypes, with thicker stems, shorter internodes, compact canopy, more leaves that were darker green and felt thicker (and had a greater mass per unit area), and had more apical branches and flowers than those of the wild type. $T_2$, $T_3$, and $T_4$ segregants included similar semi-dwarf (hemizygous) as well as dwarf (homozygous) individuals.

Figure 2:
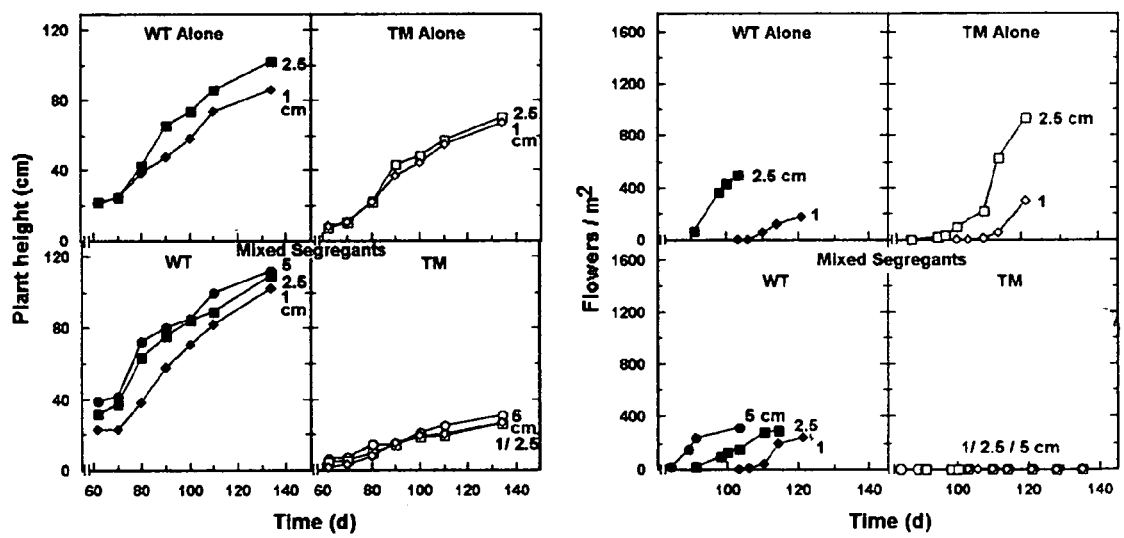
FIG. 2 illustrates the suppression of growth and flowering of TM (transgenic mitigator) bearing tobacco plants carrying a dwarfing mitigator gene in tandem with the primary herbicide resistance transgene (open symbols) when in competition with the wild type (closed symbols) (right panels), and their normal growth when cultivated separately without herbicide (left panels). The wild type and transgenic hemizygous semi-dwarf/herbicide resistant plants were planted at 1, 2.5, and 5 cm from themselves or each other, in soil.
Figure 3:
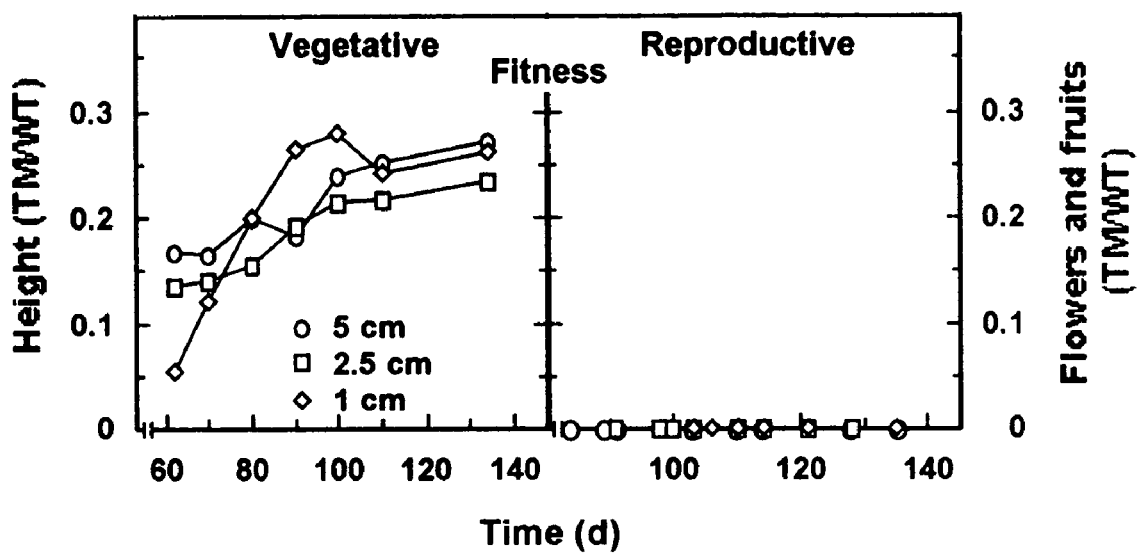
FIG. 3 illustrates the suppressed vegetative and reproductive fitness of TM transgenic tobacco plants in competition with wild type tobacco. The points represent the calculated ratio of data for TM to wild type plants in FIG. 2.

The dwarf and imazapyr resistant TM transgenic hybrid tobacco plants (simulating a TM introgressed hybrid) were more productive than the wild type when cultivated alone. They formed many more flowers than the wild type, which is an indication of a higher harvest index (FIG. 2). Conversely, the TM transgenics were weak competitors and highly unfit when co-cultivated with the wild type in ecological simulation competition experiments (FIGS. 2,3). The lack of flowers on the TM plants in the competitive situation (FIG. 2) led to a zero reproductive fitness of the TM plants grown in a 1:1 mixture with the wild type at the spacings used, which are representative of those of weeds in the field (FIG. 2). The highest vegetative fitness was less than 30% of the wild type (FIG. 3).

Thus, it is clear that the tandem construct of a herbicide resistance gene with a dwarfing transgenic mitigation gene is advantageous to a crop growing alone, while disadvantageous to a crop-weed hybrid growing in a competitive environment. If a rare pollen grain bearing such tandem transgenic traits bypasses containment, it must compete with multitudes of wild type pollen to produce a hybrid. Its rare hybrid progeny must then compete with more fit wild type cohorts during self-thinning and establishment. Even a small degree of unfitness conferred by the tandem TM construct would bring about the elimination of the vast majority of progeny in all future generations as long as the primary gene provides no selective advantage while the linked mitigator gene confers unfitness. Further large-scale field studies will be needed with crop/weed pairs to continue to evaluate the positive implications of risk mitigation.

Dual mitigating effect of Δgai—inhibiting the production of fertile pollen: The backcross generations containing the TM constructs described above, are all the result of pollination of the transgenic crops by the wild type, as the pollen of the TM transformants was sterile in all the primary transformation events. This means that the Δgai mitigator gene acts as both a containment mechanism precluding outcrossing to wild type, and as a mitigator, preventing out-crossing in any rare hybrid offspring resulting from incoming pollination by the wild type. Thus, the TM construct-bearing crop is also inherently protected from becoming a voluntary weed. This is not disadvantageous for the crop, as tobacco, along with other crops, is not grown commercially for its seed, but rather for the leaves, and the production of seeds is prevented in leaf production fields.

Figure 4:
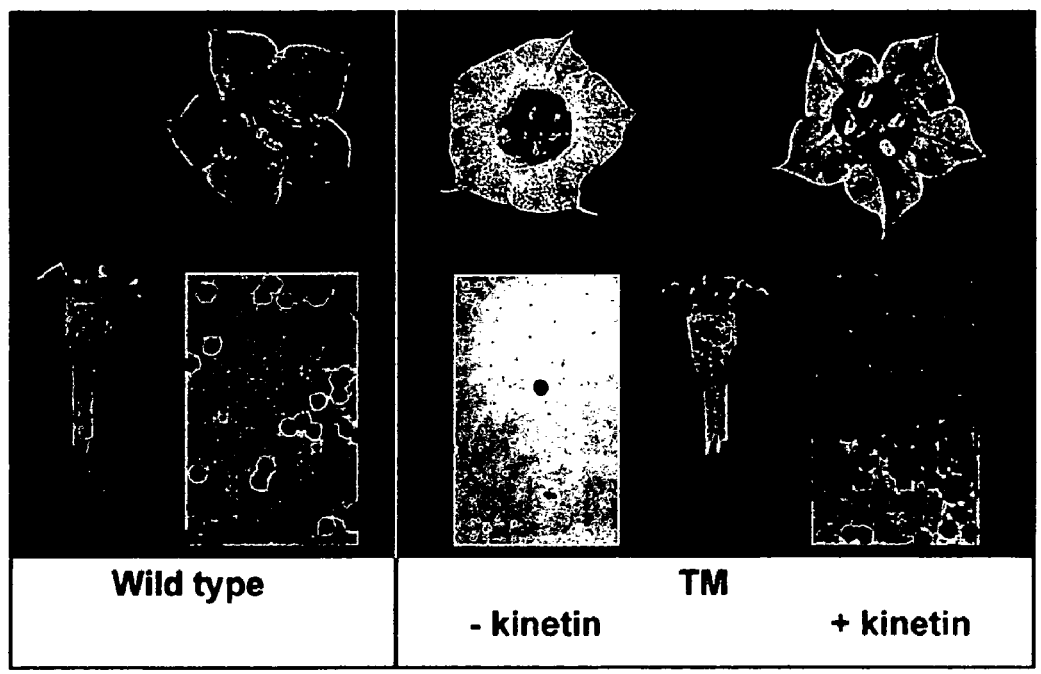
FIG. 4 is a photograph demonstrating the restoration of fertility by kinetin application to transgenic TM tobacco plants transformed with dual-mitigating construct. Restoration of fertility was by spraying of kinetin. Representative kinetin-restored tobacco flowers on Δgai-transformed male sterile plants (TM, +kinetin) were morphologically normal and had pollen viability similar to that of the self-pollinated wild type flowers. Note shriveled anthers and mainly non-viable pollen in TM-transformed tobacco without kinetin (TM, −kinetin) and normal anthers and pollen when kinetin is used for restoration.

Seed production on Δgai male sterile plants: The Δgai effect on pollen production is not irreversible: treatment of plants with cytokinins results in plants producing fertile pollen, and capable of self fertilization. Hemizygous imazapyr resistant and semi-dwarf primary TM tobacco transformants (lines 7, 8, and 10) were transferred to soil and grown to flowering. After male sterility was observed in the first few flowers, 3 plants from each line were sprayed with 15 mg of kinetin (Sigma, St Louis, Mo.) per plant. The chemicals were in an aqueous solution containing 0.1% (v/v) Tween 20 surfactant. The control group received the surfactant solution only, or none at all. All applications were made through foliar spray every other day for 2 weeks. Female fertility was assessed by backcrossing wild type pollen donors were backcrossed to one plant from each line without kinetin application (FIG. 4). At maturity, the capsules formed on each plant were counted and the dry weight of seed set of up to 5 capsules per each plant was measured. Normal seed set was observed.

Anthers were collected from three flowers per plant. A minimum of three plants per biotype were analyzed. Pollen viability was scored by staining the pollen with cotton blue stain [Phillips, R. L. in G. Clark, ed. "Staining Procedures", Willimas & Wilkins, Baltimore pp. 361-6] and counting the numbers of nonviable and deeply stained viable grains with normal morphology. Normal pollen was observed on the kinetin treated plants, a few malformed pollen grains were found on the untreated transformed plants.

Floral bud and pistil development of the TM transgenic plants were similar to that of wild type plants. In contrast, the anthers of these transgenic plants were noticeably smaller and lighter in weight already at an early stage of development. Application of kinetin, a synthetic cytokinin, restored the fertility to the transgenic plants and resulted in normal fertilization and seed development. As shown in FIG. 4, flower anthers from one of the kinetin-restored transgenic lines (line 7) were visibly shedding pollen. Pollen viability, scored by staining tests, of these restored lines was >93% compared to approximately 0% of non-treated plants (FIG. 4). The kinetin-restored flowers were morphologically normal and had typical seed yields, similar to those of the self-pollinated wild type flowers and the TM sterile flowers crossed with the wild type pollens. Thus, seed production, although normally prevented in the plants transformed with the tandem TM construct, is inducible with well known effectors, producing normal fertilization and seed development.

Example 2

Mitigation of Transgene Introgression in Oilseed Rape (*B. napus*) by Tandem Constructs using the Dwarfing Δgai Gene A large variety of different primary genes have been inserted into oilseed rape, the crop source of canola oil (Table 2). Oilseed rape (*Brassica napus*) is an open-pollinated crop that crosses freely with a weedy relative (*B. rapa*) with which it shares one of its two similar genomes, and less freely with various other related species. The open pollinated nature of the species has already led to inadvertent stacking of herbicide resistance transgenes (Hall et al, Weed Sci 2000;48:688-94), and movement of herbicide resistance traits, in the related weedy species and in the volunteer weeds, could lead to control problems in rotational crops, especially when stacked, even further limiting the control options. The volunteer weed problems are exacerbated by the fact of oilseed rape not being fully domesticated. Many varieties prematurely shatter large numbers of seed—guaranteeing a volunteer weed problem. Thus, genetically engineered disease and insect resistances could offer fitness advantages to weedy and wild relatives. Further, the introgression of pharmaceutical protein-encoding genes as well as those encoding polymer synthesizing genes or genes for industrial enzymes would be undesirable, and potentially problematic in other varieties. Thus there is a strong need to mitigate the flow of genes from transgenic varieties.

In order to determine whether the effects of transgene introgression into weedy and volunteer varieties of oilseed rape can be mitigated by TM genes, the same tandem herbicide-resistant-dwarfing TM construct described herein above in Example 1 was transformed into oilseed rape. Expression of the transgenes and survival of the selfed progeny, as well as the hybrids with the weedy variety Brassica campestris=B. rapa was measured, as described herein below, revealing efficient transgenic mitigation of introgression in oilseed rape by the dwarfing Δgai gene.

Figure 5:
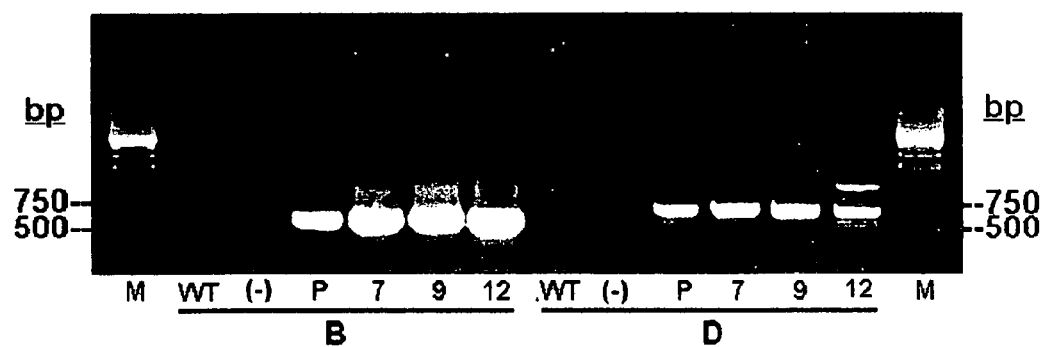
FIG. 5 shows the transformation of Brassica plants with a dwarf/herbicide resistant TM construct. Detection of the transformed primary AHAS resistance and Δgai dwarfing mitigator genes in primary transgenic B. napus plants is performed by PCR, as described herein below. Lane M, Molecular marker (1 kb DNA ladder); lane WT, wild-type; lane (−), control without template DNA; lane P, TM 1 plasmid control; lanes 7, 9, and 12 denote representative independent putative TM transgenic plants; B and D denote the sites chosen for PCR amplification within the TM T-DNA, as indicated on the TM 1 plasmid map described in Example 1, FIG. 1a herein above.
Figure 6:
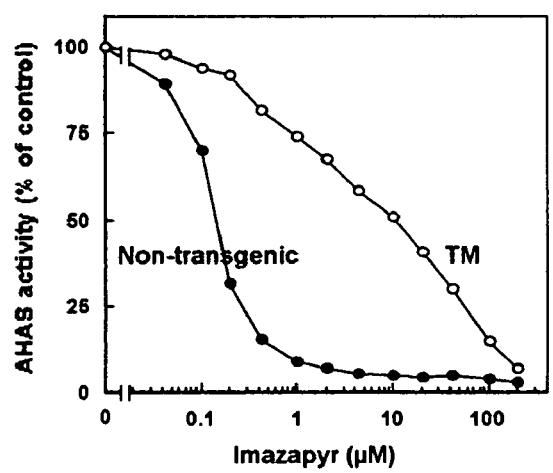
FIG. 6 is a graph showing the expression of imazapyr resistance in TM transgenic dwarf/herbicide resistant B. napus. The AHAS enzyme activity was spectrophotometrically assayed in leaf discs and presented as percent activity of controls tested in the absence of the herbicide. The enzyme activity of the non-transgenic and TM controls=0.054 and 0.070 μmol acetolactate cm$^{-2}$ leaf discs h$^{-1}$, respectively. The individual plants assayed were non-transgenic (closed circles), and hemizygous TM transformants (open circles). The TM curve represents the mean of three independent transgenic events. One cm$^2$ of untreated leaf discs contains 88.5±2.5 μg soluble proteins.

Experimental Procedures:

Transformation of oilseed rape (B. napus cv. Westar): The Agrobacterium tumefaciens-mediated transformation protocol of Moloney, et al (Plant Cell Reports 1989; 8,238-242) using excised cotyledonary petioles of B. napus cv. Westar seedlings was followed with some modifications. Excised cotyledons of axenic B. napus cv. Westar seedlings were inoculated by dipping the cut end of a 2 mm petiole in a suspension of A. tumefaciens strain EHA105 or EHA 101 containing the same TM 1 construct described in detail in Example 1. Non-transformed cotyledons served as negative controls. After co-cultivation for 2.5 days, the cotyledons were regenerated on Murashige-Skoog (MS) medium containing 500 mg/L carbenicillin to kill A. tumefaciens and 20 mg/L kanamycin as the primary plant selectable marker. Some healthy calli developed on the cut petioles and regenerated into green shoots which were then sub-cultured onto shoot elongation medium containing 300 mg/L carbenicillin and either 20 mg/L kanamycin or 0.2 μM imazapyr herbicide as secondary selectable marker of the putative transformants. The shoots were then rooted, potted, and transferred to the greenhouse to grow flower and set seed. The putative transformants were tested by PCR (FIG. 5) and by AHAS enzymatic assay (as described in Example 1 herein above) (FIG. 6) to confirm TM transformation. Southern blot analysis according to Sambrook et al (1989) was used to test the stability and the number of copies of the integrated ahas$^R$ and Δgai tandem genes. Semidwarf and imazapyr resistant plants were selfed and crossed with weedy B. campestris as described below.

Inheritance of the Tandem TM Construct Transgenes in Oilseed Rape

Seed germination in the presence of kanamycin or imazapyr: A discriminatory dose level of Nitsch (Nitsch, Nicotiana. Phytomorphology 1969; 19, 389-404) agar medium containing 150 mg/L kanamycin or 0.3 μM imazapyr inhibiting the growth of non-transformed plants was determined. Surface sterilized seeds of non-transgenic, and TM B. napus plants were planted on either medium. Sensitive seedlings stopped growing within 10 days forming only short roots and cotyledons, while resistant seedlings formed long roots and true leaves and continued their growth. The segregation ratio of non-transgenic to TM of each line was calculated. Resistant/dwarfed seedlings were grown to maturity in soil and the plants were analyzed for AHAS resistance and for ahas$^R$ and Δgai insert by PCR, as described above.

Crossing of transgenic B. napus genes into weedy B. canipestris and analyses:

Manual pollination procedure: TM transgenic B. napus plants (lines 9, 9B, 16, 18) (male parent); were manually crossed with weedy wild type B. campestris (female parent). Maternal flowers were emasculated prior to anthesis, pollinated by rubbing two to three male parent anthers on the stigma surface, and covered with glassine pollination bags for 10 days to prevent uncontrolled cross pollination. Surplus flowers on maternal plants were removed. Mature siliques were harvested and the seeds were sorted and counted as fully developed, pre-maturely germinated within siliques, or aborted (small and shrunk). Fully developed seeds were used to grow $T_1$ hybrid plants.

Inheritance of ahas$^R$ Δgai activity in the TM $T_1$ hybrid progeny Introgressed $T_1$ hybrid offspring plants were selected according to their expression of ahas$^R$ and Δgai genes. Fully developed seeds obtained from the (B. napus×B. campestris) crosses were germinated on imazapyr selective medium. The resistant/semi-dwarf hybrid plants were cultivated in the greenhouse, and were analyzed by AHAS assay and PCR as described herein above (Example 1).

Backcross of TM $T_1$. hybrids to the parental weedy B. campestris: TM $T_1$ hybrids (male) were backcrossed to the parent B. campestris (female) by hand pollination. The produced seeds were selected and used to grow the TM T1-BC$_1$ plants, which were allowed to be selfed and set seed. Also, the T1-BC$_1$ plants (male) were manually backcrossed again to B. campestris (female) to obtain the TM T1-BC$_2$ progeny.

Productivity of Brassica biotypes without self competition: TM transgenic vs. non-transgenic Brassica crops, hybrids, as well as the backcrosses plants were grown separately in 13 cm diameter 1L pots filled with a 1:1:1 mixture of peat, crushed tuff rock, and loam and with considerable spacings between pots such that the plants were not competing with each other. The plants were grown under ambient glasshouse light (1589.7±56.3 μE m$^{-2}$s$^{-1}$), 32.3±1.2° C. Light intensities are the averages (±SE) of noontime measurements made on seven occasions during the growing season. The plants were randomized every 2 weeks to minimize microenvironmental effects. Optimal water was supplied, and the plants were treated weekly against diseases and arthropods. The young transgenic vs. non-transgenic plants were assayed for resistant AHAS enzyme activity by the leaf disc test (as described herein above, Example 1).

Phenotypic characteristics were determined at intervals on all biotypes. Plant height was measured from the apical meristem of each plant down to soil surface level. The number of live leaves of each plant, the number of stem branches were counted. Stem thickness was measured at maturity at 5 cm above soil, and leaf internode spacing was measured from the first basal leaf toward the apical branches carrying flowers and siliques. The fresh weights of the shoots and roots were separately measured at different growth stages. The lifetime seed production was quantified to compare the performance of TM transgenic vs. non-transgenic Brassica plants of the different biotypes. When the plants stopped flowering, the number of siliques was counted for each plant (if they appear to contain at least one developed seed). Ten mature, undehisced siliques were randomly selected from two to three branches per plant for seed counts. In the few cases wherein it was not possible to retrieve 10 siliques a smaller sample was used. The average number of fully developed seeds per silique and the number of seeds per plant (number of siliques×average number of seeds per fruit) were then calculated. The total seeds were sorted and counted as: fully developed, prematurely germinated within siliques, or aborted (small and shrunk). Total weight of cleaned, fully developed seeds per each plant was also measured. The mature plants were then cut at the soil surface, and the dry weight of the shoots were measured for each plant separately, and the harvest index was calculated.

Competition of TM transgenic vs. non-transgenic *Brassica napus* plants and self competition of each alone: The competitive interactions between the TM transgenic vs. non-transgenic *Brassica napus* plants were assessed in replicated greenhouse experiments. In the first experiment seeds obtained from the selfed homozygous TM lines $T_1$-J9-4 and -6 were used to grow the TM plants in mixed cultures with the non-transgenic plants in a 1:1 TM/WT ratio. All the $T_2$ progeny were TM transgenic, as confirmed by seed selection on a medium containing a discriminatory dose of imazapyr (0.5 μM) that inhibited the growth of the non-transgenic segregants, but did not affect the development of the resistant TM plants. The non-transgenic seeds were obtained from pure non-transgenic lines that were regenerated by tissue culture techniques, the same that used to generate the TM transformants, but without using *Agrobacterium*. In yet another trial, the progeny of a heterozygous TM line J9-2 and J9-3 segregated as 3:1 TM/WT were used, representing a mixed population. Both experiments were conducted in 55×41×22 cm plastic containers filled with a mixture of peat, crushed tuff rock, and loam (1:1:1). Each container was divided with a string to give 4 micro-plots. The TM transgenic vs. non-transgenic *Brassica napus* mixed seeds were hand-sown in soil at 2.5- and 5-cm spacing (about 360 and 90 seeds/container, respectively), without using the selective herbicide. Monoculture controls of non-transgenic plants alone and homozygous transformed TM plants alone were also grown at the same spacings, and at 10-cm spacing of non-transgenic *Brassica napus* (about 30 seeds/container). Plants were grown under ambient greenhouse light (987.91±52.7 $\mu E\ m^{31}\ 2s^{31\ 1}$), 25.5±1.85° C. Light intensities are the averages (±SE) of noontime measurements made on ten occasions during the growing season. All replicates were randomly placed on glasshouse benches to minimize micro-environmental effects. Optimal water was supplied, and the plants were weekly treated against disease and arthropods. The young plants were assayed for resistant AHAS enzyme activity by the leaf disc test (as described herein above, Example 1). All resistant dwarf transgenics had distinguishable compact canopies and darker green leaves than the non-transgenics. After AHAS enzyme screening, the plants were labeled with a numbered tape attached to the stem for future reference. The leaf discs of the non-transgenic plants all contained wild-type, herbicide susceptible AHAS.

Performance and reproductivity of transgenic TM *B. napus*: The performance and reproductivity of survived TM transgenic vs. non-transgenic *Brassica* plants was quantified by measuring various growth parameters at time intervals, as described above in the productivity of *Brassica* biotypes without self competition. The number of surviving plants of each biotype were also recorded.

Potential for competition between wild type *B. campestris* and TM $T_1$, hybrid offspring as well as backcross generation (TM $BC_1$) to *B. campestris* was evaluated in screen-house conditions, each group being internal triplicated.

The vegetative fitness (based on plant height) and the reproductive fitness (based on the total seed number formed per plant and the total seed output/biotype/unit area) of TM hybrids or BC relative to wild type *B. campestris* plants, will be calculated at the time intervals as a TM/WT ratio.

Results

Expression of Tandem Herbicide Resistance-Dwarfism TM Construct Confers Superior Growth in Transgenic *Brassica* Biotypes Grown Alone.

Figure 7:
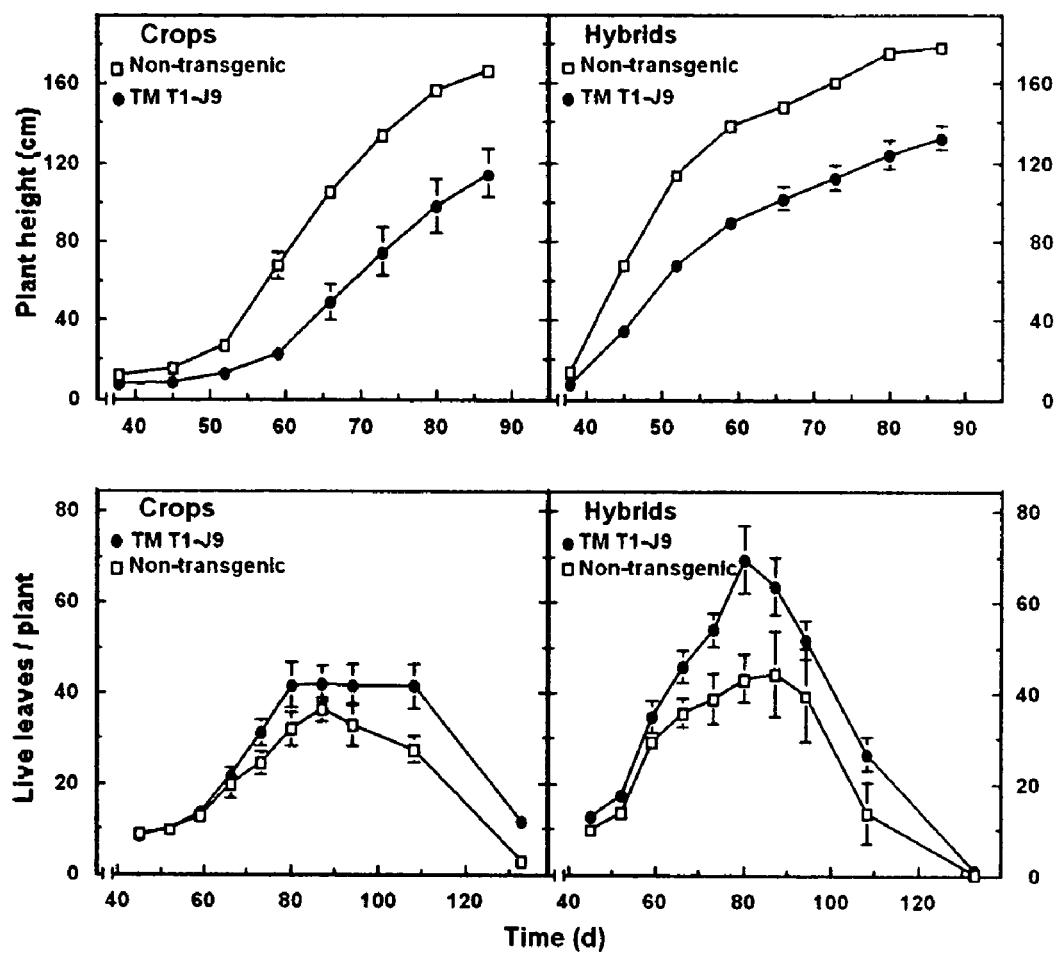
FIG. 7 is a graphic representation of the growth of transgenic TM Brassica grown without self competition. The growth parameters (plant height-upper panels, and leaf bearing-lower panels) were determined at intervals on the non-transgenic (open squares) and the TM (line 9) transgenic plants (closed circles) grown separately in 1L pots with considerable distance between them. The points are the mean (±SE) of 13-15 non-transgenic (open squares) and TM (closed circles) plants. Absence of SE bars indicates that the standard errors (SE) were smaller than the data points.

Sixteen independent plantlets were regenerated and were observed to have formed long, healthy roots in the presence of 20 mg/l kanamycin, which inhibits the non-transgenics. Southern hybridization analysis of genomic DNA from representative TM *B. napus* $T_0$ transformants showed single gene copies of the ahas$^R$- Δgai tandem insert in lines TM $T_0$-7, 8, 9, and 12. All the TM Brassica crops, hybrids, and backcrosses (BC) with the wild type weedy *B. campestris* had similar dwarf phenotypes, characterized by delayed growth and flowering. Dwarfism was clearly expressed at the rosette stage more than after bolting. The transgenic TM plants had also more abundant, darker green, and thicker leaves, and thicker stems than those of the non-transgenic biotypes (FIG. 7). The transgenic TM crops were more productive than the non-transgenic plants when grown alone, and the dry weight of total fully developed seeds per TM plant was greater than that of the non-transgenics.

Figure 8:
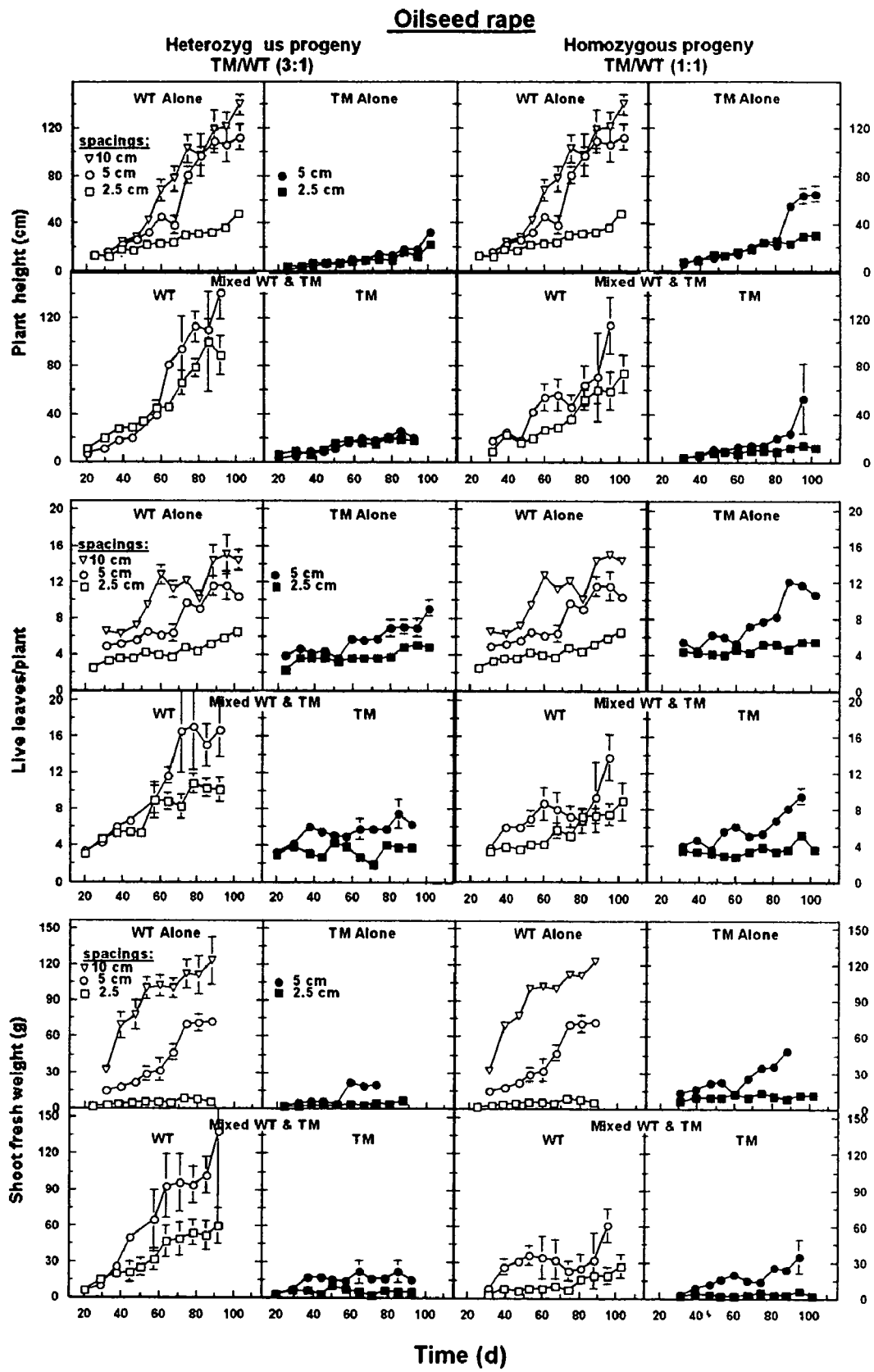
FIG. 8 is a graphic representation of the impaired growth of transgenic TM dwarf/herbicide resistant Brassica grown with non-transgenic Brassica. The growth parameters (plant height-upper panels, leaf bearing-middle panels, and shoot fresh weight-lower panels) indicate vegetative fitness of dwarf/herbicide resistant TM transgenic oilseed rape when in competition with non-transgenic crop plants, simulating introgression of the transgenic TM construct. Non-transgenic (open symbols) and dwarf/herbicide resistant (closed symbols) plants, were planted at 2.5 and 5 cm from each other in soil without herbicide, at two different transgenic:wild-type ratios (TM/WT 3:1, left panels; TM/WT 1:1, right panels). Absence of SE bars indicates that the standard errors (SE) were less than the data points.

Expression of Tandem Herbicide Resistance-Dwarfism TM Construct Confers Significant Competitive Disadvantage to Transgenic *Brassica* Biotypes Co-Cultivated with Wild Type:

Both the transgenic TM heterozygous and homozygous transgenic *B. napus* plants were weak competitors when co-cultivated with the non-transgenic crop plants in ecological competition experiments (FIG. 8). By the time the non-transgenics had finished flowering and formed many siliques, all the surviving TM plants cultivated at 2.5-cm spacing failed to flower and had formed only very small canopies, indicating that the reproductive fitness of the TM plants was much lower than that of the non-transgenic competing plants. Significantly, it was observed that those TM plants successful in forming weak flower buds at 5-cm spacing were only those growing close to the edges of the containers, able to receive more light than those growing in the middle of the containers. However, both the weakly flowering and the non-flowering transgenic TM plants failed to produce mature siliques or viable seeds.

In oilseed rape, unlike in tobacco, the Δgai dwarfism gene is active at the rosette stage, and does not seem to act when the plants start bolting. The TM plants were fertile, obviating the need to restore fertility with cytokinins, as in Example 1. As demonstrated herein above, the rare hybrid offspring from escaped pollen bearing transgenic mitigator genes would not pose a dire threat, especially to wild species outside cultivated fields, as the amount of pollen reaching the pristine wild would be minimal, and the transgenic TM hybrids of impaired vigor and robustness.

Dual Mitigation of Introgression of Primary Trait into *Brassica* with Dwarfism and Shatterproof Genes In order to determine the effect of the expression of additional mitigator genes in transgenic oilseed rape, the coding sequence of the shatterproof gene of *Brassica* (GenBank Accession No. AF226865, SEQ ID NO. 9, as described by Lilegren, S. J.,et al SHATTERPROOF MADS-box genes control seed dispersal in *Arabidopsis*. Nature 2000; 404:766-770) was spliced into the construct to further flank the primary transgene of choice. Transformation and expression of the shatterproof gene were verified by PCR, as described in Examples 1 and 2. Surprisingly, the resulting transgenic oilseed rape lacks the high level of seed-shatter characteristic of wild type *Brassica*, precluding much of the volunteer weed problem, and guaranteeing that the very rare hybrids that do manage to flower despite expression of the Δgai mitigator gene, end up with their seeds harvested along with the crop and sent to the oil-crusher, thus further mitigating the introgression of primary traits into unintended crops.

Example 3

Mitigation of Introgression of Genetically Engineered Pharmaceutical (and other) Transgenes in Corn—Precluding Volunteer Weed Problems and Gene Outflow A large number of genes have been engineered into corn (Table 5), and corn with herbicide resistance genes and Bt insect resistance are in widespread agronomic use. For example, the US Environmental Protection Agency has recently (November 2003) approved the sale and use of Yield-Gard Plus corn by Monsanto, Inc, a variety of corn having genetically engineered resistance to corn borer and rootworm. Most of the genes engineered into corn pose no rational biosafety risk outside of the center of origin of corn, except were it is considered undesirable to have gene flow to organically cultivated crops. Nonetheless, a strong and very vocal opposition to the cultivation and use of genetically engineered corn has grown, exemplified by the costly and damaging recall of many corn products containing Aventis CropScience's "Starlink" Bt corn from the world market in 2000.

TABLE 5

Examples of primary genes inserted into corn for potentially commercial purposes - USA field releases

| Type of gene/phenotype | Gene or protein encoded | APHIS[#a] |
|---|---|---|
| Herbicide Resistance | | |
| Glufosinate | *pat* | 03-301-04 |
| Glyphosate | EPSP synthase | 03-301-13 |
| | Glyphosate oxireductase | 96-099-02 |
| Imidazolinone group | CBI | 03-301-08 |
| Protox inhibitors | CBI | 03-021-02 |
| Isoxazole group | CBI | 02-070-19 |
| Chloroacetanilide group | CBI | 00-073-06 |
| Cyanamide | CBI | 00-021-03 |
| Dalapon | CBI | 00-024-02 |
| Insect Resistance | | |
| Coleopteran | CBI | 03-301-13 |
| | Bt | 03-140-03 |
| Lepidopteran | CBI | 03-301-04 |
| | Cry 1A Bt | 03-022-01 |
| Disease Resistance (fungi) | | |
| *Rhizoctonia* | CBI | 03-202-12 |
| *Fusarium* ear rot | CBI | 03-021-02 |
| Southern corn leaf blight | CBI | 02-079-13 |
| CBI | CBI | 01-123-01 |
| *Botrytis* | CBI | 01-131-01 |
| *Aspergillus* | Chitinase | 00-096-04 |
| | Chitinase + glucanase | 98-322-03 |
| Smut | CBI | 00-021-03 |
| Gray leaf spot | CBI | 99-028-01 |
| Northern corn leaf blight | CBI | 99-032-02 |
| *Septoria* | CBI | 99-032-02 |
| *Helminthosporium* | CBI | 98-292-03 |
| *Alternaria* | CBI | 98-078-15 |
| *Cercospora* | antifungal + ribosome inactivating proteins | 96-106-04 |

TABLE 5-continued

Examples of primary genes inserted into corn for potentially commercial purposes - USA field releases

| Type of gene/phenotype | Gene or protein encoded | APHIS[#a] |
|---|---|---|
| Disease Resistance (Bacterial) | | |
| CBI | CBI | 01-123-01 |
| Disease Resistance (viral) | | |
| CBI | CBI | 01-123-01 |
| MDMV | MDMV coat protein | 95-328-04 |
| MCMV | MCMV coat protein | 94-048-03 |
| Agronomic Quality[a] | | |
| Seed Quality | CBI | 03-303-04 |
| Environmental stress | CBI | 03-290-03 |
| Yield increase | CBI | 03-288-10 |
| Germination increase | CBI | 03-276-06 |
| Drought tolerant | CBI | 03-276-10 |
| Seed color altered | BI regulatory gene | 03-258-07 |
| Male sterile | B cell lymphoma related gene X | 03-121-02 |
| | Male sterility protein | 03-114-05 |
| | barnase | 03-077-15 |
| Fertility altered | Aldehyde dehydrogenase rf2a restorer genet | 03-091-19 |
| | TURF13 mitochondrial + aldehyde dehydrogenase | 03-091-12 |
| | adenine methylase + CBI | 03-015-01 |
| Senescence altered | CBI | 03-052-56 |
| Endosperm DNA synthesis altered | cyclin dependent kinase + retinoblastoma related protein | 03-050-08 |
| Development altered | Mu 1 transposable element | 02-3354-01 |
| Enhanced photosynthesis | CBI | 98-128-22 |
| Cold tolerant | CBI | 02-262-05 |
| Storage protein altered | CBI | 02-072-10 |
| Increased Stalk strength | | 02-023-01 |
| Tryptophan level | CBI | 02-070-26 |
| Gene expression altered | glutathione transferase | 02-032-20 |
| Carbohydrate metabolism altered | CBI | 98-041-05 |
| Product Quality[a] | | |
| Oil profile altered | CBI | 03-272-03 |
| | acetyl-CoA-carboxylase | 98-093-05 |
| Protein quality | CBI | 03-258-14 |
| | glutenin | 02-087-01 |
| | homoserine dehydrogenase + aspertokinase | 95-291-19 |
| | zein storage protein | 95-291-07 |
| Lysine level altered | CBI | 03-258-15 |
| | aspartokinase and dihydropicolinate synthase | 99-305-01 |
| Animal feed quality improved | CBI | 03-022-02 |
| Phytate reduced | CBI | 02-302-07 |
| Starch metabolism altered | starch synthase | 02-289-07 |
| | ADP glucose pyrophosphorylase | 02-261-03 |
| | isoamylase debranching enzyme | 99-302-11 |
| | Levansucrase | 98-238-04 |
| | amylase | 98-139-01 |
| Fumonisin degradation | CBI | 02-023-02 |
| methionine increased | CBI | 99-160-03 |
| | storage protein | 98-070-01 |
| Novel protein (Pharmaceutical) | CBI | 99-055-11 |
| Reduced lignin | Omethyltransferase | 98-215-05 |
| Colored seed | anthocyanin regulatory gene | 97-189-05 |
| Pharmaceutical traits | Man & mouse CBI genes | 03-143-01 |
| | CBI | 03-086-01 |
| | Hepatitis B virus surface antigen | 01-187-01 |
| | G-glycoprotein | 98-117-04 |
| | α and β human subunit hemoglobins | 98-117-01 |
| | Enterotoxin B | 01-190-01 |
| | human serum albumin | 98-117-03 |
| | antibody | 99-271-04 |
| | human procollagen | 98-117-02 |

TABLE 5-continued

Examples of primary genes inserted into corn for potentially commercial purposes - USA field releases

| Type of gene/phenotype | Gene or protein encoded | APHIS[#a] |
|---|---|---|
| Industrial enzyme produced | Turkey laccase | 02-113-09 |
| Novel protein | CBI | 02-081-10 |
| | Pentadiplandra brazzein | 02-081-13 |
| | Cecropin | 99-106-11 |
| | lipase | 99-091-04 |
| Polymer production | Ketothiolase + acetoacetylCoA reductase + polyhydrobutyrate synthase | 01-150-01 |

[a]Some product quality traits listed as agronomic traits by APHIS

It is mainly the industrial and pharmaceutical genes being engineered into corn that clearly pose a risk—most importantly, a risk of introgression into unintended crops by volunteerism. The containment of pharmaceutical transgenes has relied on "physical" methods [harvest, and roguing (physically removing) of volunteer transgenics], and is clearly inadequate. This was demonstrated in the recent "Prodigene" scandals, in which temporary volunteer escape of "Prodigene" genetically engineered maize contaminated subsequent conventional crops grown on a field used for the corn in the previous season, and in which suspicion of cross-pollination by genetically engineered corn lead to the destruction of hundreds of acres of nearby conventional corn. These mishaps resulted in both heavy fines from the EPA, and widespread concern regarding the introduction of the engineered corn into widespread use.

Thus, it will be appreciated that the biological containment strategies described herein can be preferable to dependence on physical containment, but the mitigation strategies would still be required due to the inherent imperfection of such methods of containment.

High Sucrose and "Shrunken Seed" Mutations as TM Mitigator Genes

Maize pharmaceutical transgenes are expressed in embryo tissues, and a potential tandem mitigating gene could be any dominant gene that affects the endosperm. One example of such a mitigator trait is the various "shrunken seed" loci, especially those where sugar transformation to starch is inhibited. Such shrunken seeds, with their high sugar content, are much harder to store than normal maize but are extremely unfit in the field: "The higher sucrose levels of (natural) sh2 corn contributes directly to lower kernel weight and density, increased mature pericarp thickness and higher bubble volume. The high sucrose levels were associated with higher leachate conductivity, greater susceptibility to soil pathogens, and inferior field germination and viability compared with near-isogenic counterparts" (Zan, G H; Brewbaker, J L 1999 Seed quality of isogenic endosperm mutants in sweet corn. Maydica 44: 271-277). Thus, high sucrose, shrunken seed corn kernels would most likely to be unable to survive over winter, and even in the event that they would, will be diseased and non-competitive in spring, preventing their transformation into volunteer weeds.

TM Construct Targeted for Expression in the Corn Embryo

Because the endosperm of corn is 67% pollen genes, it is important that expression of pharmaceutical encoding genes be limited to the embryo. For example, a tandem construct is designed whereby a primary pharmaceutical transgene of choice is flanked by mitigator sequences selected to confer inhibited starch biosynthesis, all under control of an endosperm-specific promoter sequence. Briefly, a primary pharmaceutical gene such as the antigenic Hepatitis B virus surface antigen gene (such as GenBank Accession Nos. AF 134134-134146) or the α and β human subunit hemoglobin genes (GenBank Accession Nos. J 00153 and AF 117710, respectively, and see Table 3 herein above) is cloned into a suitable plant transformation vector, such as *Agrobacterium tumefaciens* (see Examples 1 and 2 herein above) along with a suitable marker or selector gene, so as to be operably linked to an RNAi or anti-sense oriented sequence chosen from exon 1 of the isoamylase (su1) locus of maize (GenBank Accession No. AY290398) under the control of an endosperm-specific expression promoter, for example, the os-GT 1 and os-AGP rice glutein promoters, the maize zein zmGBS and zmGBS promoter, the wheat glutein Glu-1D-1 (HMWG-Dx5) promoter, barley endosperm-specific hordein promoters B(1)- or D-, or the like, to ensure endosperm-specific expression. Methods for endosperm-specific expression of transgenes in plants are well known in the art (see for example, U.S. Pat. No. 5,677,474 to Rogers, and U.S. Pat. No. 6,329,574 to Lundquist et al, both incorporated herein by reference, and Russel et al, Transgenic Res 1997; 6:157-68). The primary pharmaceutical transgene of choice can also be further operably linked to an additional RNAi or anti-sense oriented sequence chosen from Sh2 endosperm ADP-glucose pyrophosphorylase locus of maize (Bhave et al., 1990 —Genbank Accession # S48563), conferring the "shrunken seed" phenotype with further impaired starch biosynthesis (methods for the cloning and expression of sh2 sequences are described in detail in U.S. Pat. No. 5,589,618 to Hannah et al, which is incorporated herein by reference).

Mitigation of Introgression of Pharmaceutical Encoding Gene in Corn and Maize by Chimeric TM Construct:

Stable transformation, transgene expression and transfer of the transgenic phenotype to successive generations of the crop is determined as described herein above (see Examples 1 and 2). The resulting regenerated corn plants produce the pharmaceutical in the embryo, but, having endosperm resembling that of "supersweet" corn, volunteer seeds from the transgenic crop or any hybrids with nearby varieties are non viable. Introgression of the primary pharmaceutical gene of choice into unintended crops from corn is further prevented by the TM constructs described herein above since, in the unlikely event of rare shrunken seed appearance on neighboring varieties possibly resulting from cross pollination, these mutant seed phenotypes are identified and sorted out during any processing, due to their low weight and low bulk density (Ruan et al. Plant Cell, 2003; 15:952-64).

Example 4

Mitigating the Effects of Hybridization Between Rice and Feral Weedy (Red) Rice and Wild Rices According to the Food and Agriculture Organization (FAO) of the United Nations, rice is clearly a crop with problems:

(a) Rice culture has demographic problems due to the continuously increasing average age of rice farmers; transgenics are needed to replace labor;

(b) Rice has geographic problems; areas are being taken out of production faster than are being brought into cultivation due to urban encroachment, competing crops, soil degradation and salinization, and lack of water; transgenics are needed to increase yield on the remaining land.

(c) Rice culture has agronomic problems. Direct seeding has alleviated the labor problems of transplanting while exacerbating the weed problems; transgenics are needed to overcome weed problems.

Herbicide use in rice facilitates weed control in low stature, high harvest index "green revolution" rices, allowing fewer farmers to harvest far more nice. Return to the labor-intensive, herbicide-free, back breaking, transplanted and later hand-weeded rice seems less and less likely each day.

There are three weed groups that are globally distributed, pernicious, hard to control weeds that have become acute problems due to recently instituted cultural practices:

(a)*Echinochloa* spp. (especially *E. crus-gallis*, or barnyard grass)—have always been problem weeds in rice fields, but have recently been evolving resistance to the rice herbicides used for their control—they have evolved resistance to rice herbicides in the USA and elsewhere around the globe—over millions of hectares;

(b) The sedges (*Cyperus* and other) have never been well controlled by any herbicide chemistry, and therefore the weed-infested areas are rapidly expanding; and (c) The red rice (red sprangletop), weedy, and wild *Oryza* spp. have never been successfully selectively controlled in rice by herbicides (Baltazar, A. M., and Janiya, J. D. 1999. Weedy rice in the Philippines Wild and Weedy Rices. International Rice Research Institute, Manilla; Noldin, J. A., Chandler, J. M., and McCauley, G. N. 1999a. Red rice (*Oryza sativa*) biology. I. Characterization of red rice ecotypes. Weed Technology 13, 12-18; Noldin, J. A., Chandler, J. M., Ketchersid, M. L., and McCauley, G. N. 1999b. Red rice (*Oryza sativa*) biology. II. Ecotype sensitivity to herbicides. Weed Technology 13, 19-24). Control of red and weedy rice is especially amenable to biological and genetic engineering solutions that confer intra-generic and intra-specific selectivity. Such biological solutions, such as specific herbicide resistance, are futile, and potentially catastrophic if the rice crop transgenes for herbicide resistance (or other traits) introgress into the weedy rices, enhancing their competitive ability.

Some of the con-specific red rice and other *O. sativa* types can be considered as progenitors to, or as recently evolved feral forms of domestic rice. There are other *Oryza* spp. that have weedy characters, as well as wild species that are not competitive at present in agroecosystems (Vaughan, D. A. 1994. The Wild Relatives of Rice International Rice Research Institute, Manila). The various weedy rices shatter most of their seeds before cultivated rice is harvested, so the farmer loses rice yield while filling the soil seedbank with weeds (Baltazar, A. M., and Janiya, J. D. 1999. Weedy rice in the Philippines Wild and Weedy Rices. International Rice Research Institute, Manilla; Chin, Weed Biol and Manag, 2001;1: page 37). The problem is perpetuated since sufficient weed seed remains in the harvested crop to further sow farmers' fields with the weedy species. This weedy rice seed mimics rice seed; and it is extremely costly, and virtually impossible, to mechanically separate the weed from the rice seed.

Another feral aspect of red and weedy rice species is their protracted dormancy, germinating over a number of years, resulting in a prolonged problem in almost all rice felds (Chin, Weed Biol and Manag. 2001;1: page 37). Indeed, the similarities between domestic and weedy rice species are far-reaching, with characteristic shattering and dormancy of the weedy rices among the important distinctions. The weedy rice species have become greater problems since farmers rely more heavily on chemical means to control other weeds in rice. The domestic red and weedy rices resemble cultivated rice in their herbicide resistant character, as well, and are generally naturally-resistant to the same herbicides (Noldin, J. A., et al 1999b. Red rice (*Oryza sativa*) biology. II. Ecotype sensitivity to herbicides. Weed Technology 13, 19-24).

The easiest way to obtain selectivity among closely-related species such as rice and weedy rices is to engineer resistance into the cultivated crop. It has already been shown that red rice is easily controlled by glufosinate in fields of transgenic rice bearing the bar gene conferring resistance to this herbicide (Oard, J., et al Plant Science 2000; 157, 13-22) Many herbicide resistance genes have been engineered into rice and have been in pre-commercial field testing (Table 6).

TABLE 6

Examples of primary genes inserted into rice for potentially commercial purposes - field tested in the USA

| Type of gene/Phenotype | Gene(s) | HIS #AP |
| --- | --- | --- |
| Herbicide Resistance | | |
| Glyphosate | EPSPS | 03-190-04 |
| Glufosinate | CBI | 03-112-03 |
| Glufosinate | Strep.phosphinothricin acetyl transferase | 02-136-04 |
| CBI[a] but presumably Protox inhibiting herbicide R | CBI but presumably mutant protox gene | 02-066-19 |
| Disease Resistance (fungi) | | |
| *Rhizoctonia solani* | Arabidopsis glucanase + rice chitinase | 03-078-11 |
| *Rhizoctonia solani* + *Pyricularra oryzae* | Bean chitinase + tobacco glucanase + barley thionin + alfalfa glucanase + rice chitinases | 03-078-10 96-051-05 |
| *Rhizoctonia solani* | barley thionin | 01-127-06 |
| Disease Resistance (bacteria) | | |
| *Xanthomonase oryzae* | CBI + rice SAR 8.2 + Arabidopsis SAR 8.2 | 03-140-02 |
| | *Arabidopsis* npr1 | 02-126-08 |
| (leaf blight) | rice Xa21 receptor kinase | 01-122-10 |
| *Xanthomonas oryzae* + *Burkholderia glumae* | barley thionin | 01-127-06 |

TABLE 6-continued

Examples of primary genes inserted into rice for potentially commercial purposes - field tested in the USA

| Type of gene/Phenotype | Gene(s) | HIS #AP |
|---|---|---|
| *Insect Resistance* | | |
| Lepidopteran | CBI | 03-98-10 |
| Coleopteran | Cry IIIA | 99-70-03 |
|  | Cry IA(a) | 93-056-02 |
| Lepidopteran R | Cry IA(a) | 92-10-01 |
| *Other properties* | | |
| Yield increase | CBI | 03-203-08 |
|  | maize ADP-glucose pyrophosphorylase | 02-070-04 |
| Male sterile | CBI + organomercurylyase + mercuric | 03-112-03 |
| Heavy metal remediation | ion reductase | 03-058-01 |
| Pharmaceuticals/enzymes | human antitrypsin + CBI + Forsythia dirgent protein + Forsythia laccase + human lactoferrin + human lysozyme + Forsythia pinoresinol reductase + Forsythia pinoresino/lariciresinol reductase + Forsythia secoisolariciresinol dehydrogenase | 01-206-01 |
|  | human antithrombin + human antitrypsin + human serum albumin | 98-008-01 |
|  | human aminoglycoside-3'adenyltransferase + others above | 96-355-01 |

These genetically engineered strains of rice have not yet been released, and should not be released based on a recent studies by Gealy et al (Weed Science 2002;50,333-339; Weed Sci. Soc. Amer.-2002 Abstracts 42,139), in which herbicide resistant rice (a mutational resistance) was intentionally cultivated in fields contaminated with red rice. When the herbicide was used, excellent control (ca. 95% kill) of the red rice was achieved. However, although there was <0.05% outcrossing of the herbicide resistance trait into the remaining red rice, the hybrid offspring of these outcrosses are resistant. Calculating the rate of growth of the red rice, from the seed density and the outcrossing rate, it was projected that within two years there would be a total infestation of the red rice—as serious as. had initially been, and by which time the containment technology will have been rendered useless (Oard et al, Plant Science 2000;157:13-22). Thus, there is a need for mitigation technologies based on the significant differences between cultivated rice and its feral weedy variant, to maintain the competitive advantage of transgenic cultivated species and render the hybrids less fit. Domestic rice is semi dwarf, the plants do not tiller heavily, the seeds remain on the stalk until harvest, and the seeds germinate uniformly when planted. The feral weedy rices are competitively tall and heavily tillering, shatter most of their seeds before harvest (guaranteeing replenishment), and they have variable secondary dormancy (guaranteeing that no single agronomic anti-weed measure will deplete them entirely). Mitigator genes that guarantee dwarfism, prevent tillering and shattering, or overcome dormancy in the hybrids, when transfected separately or preferably in groups, will render hybrid progeny of domestic and feral (or wild) rices unfit to compete with the domestic rice crop. Hybrids having introgressed engineered constructs comprising primary traits such as herbicide resistance genetically linked with the abovementioned TM traits will suffer an even greater competitive disadvantage compared with non-hybrid weeds that escape herbicide treatment, since the native weedy species are tall, tillering and shattering.

In rice, the major biosafety issue is not long distance gene flow from genetically engineered populations. It will be appreciated that with all except pharmaceutical primary transgenes, in which any, even very low frequency gene flow is problematic, the main concern is with short distance gene flow, specifically within the field, to closely related weedy rice. Methods of mitigation proven effective with red and weedy rice before commercial release should be encouraged.

Genetic engineering of primary transgene and TM phenotypes in cultivated rice In rice, biolistic co-transformation leads to a very high insertion rate (70%) of co-transformed genes into the same locus (Tang et al., Planta 1999;208 552-563). Thus, in addition to the tandem constructs described herein above (Examples 1-3), the desired polynucleotide sequences can be prepared separately for biolistic transformation. Briefly, a construct comprising a functional plant promoter (see detailed description of suitable plant promoters in Examples 1, 2 and 3 herein above) and a polynucleotide sequence conferring the dwarf or semi-dwarf phenotype, such as Δgai (see Examples 1 and 2, or U.S. Pat. No. 6,307,626 to Harberd) or sequences of a gene for gibberellic acid sensitivity (such as the *Oryza* AAT gene, GenBank Accession No. BAA03844) whose natural mutational deficiency is known to be responsible for green revolution dwarfing of rice (Ikeda et al, Plant Cell 2001;13:999-1010) in an antisense orientation, are cloned in bacteria using available methodologies. Likewise, the gene for the desired pest or herbicide resistance, or other primary gene (Table 4) is cloned. The rice ortholog of the shatterproof shattering gene (Lilegren et al., 2000) is also cloned as RNAi or in the antisense orientation. A selectable marker gene, such as antibiotic resistance (suitable selectable marker genes are well known in the art and include, but are not limited to, genes encoding resistance to kanamycin [neomycin phosphotransferase (npt) II (Fraley et al. (1986) CRC Critical Reviews in Plant Science 4:1-25)], ampicillin/carbenicillin, streptomycin/spectinomycin, gentamycin, and tetracycline) is added when herbicide resistance is not the primary trait. The DNA for all these genes is purified and mixed, and biolistically transformed into rice meristem cells using methods well known in the art (see, for example, Tang et al., 1999; Anand, et al, J Exp Bot 2003;54:1101-11; Wu, et al Yi Chuan Xue Bao 2000;27:992-8, and U.S. Pat. No. 5,736,369 to Bowen et al, incorporated herein by reference, for a detailed description of the biolistic transformation of cereal grains, and also the methods described in detail herein above). Progeny are first selected for herbicide resistance, and then partially sequenced to ascertain that the genes are now tandem (see Example 1).

Expression of the two TM mitigator genes-dwarfism and "shatterproof" has no effect on the cultivated rice crop, as the cultivated crop is already dwarfed or semi-dwarf due to a mutation (which is overcome in the hybrid progeny—however, the hybrid cannot overcome the dwarfing by expression of the anti-GA gene). Likewise, domestic rice does not shatter. Hybrid disadvantage is tested by identifying and isolating hybrid weedy-species progeny having a primary transgene and TM mitigator genes, exposing such hybrids to herbicides (if the primary transgene is one of the herbicide resistance genes), and assessing survival as compared to the parent cultivated and weedy species.

The competitive disadvantage of the transgenic cultivated-weedy species hybrid can be observed by comparing the growth of such hybrids alone, co-cultivated along with the transgenic cultivated crop, and in competition with the wild-type weedy species. Red rice and weedy rice species were transformed with the herbicide-resistant-anti-shattering or herbicide-resistant-semi-dwarf constructs described above, to simulate introgression. Following selection and propagation as described above, the hybrid progeny is grown alone, and co-cultivated along with either wild-type weedy rice strains, or transformed, herbicide-resistant- "shatterproof" rice, as described for tobacco and oilseed rape in Examples 1 and 2 herein above. Mitigation of introgression of the primary transgene (herbicide resistance) in the weedy species is demonstrated by the failure of the hybrid progeny to transmit herbicide resistance to significant numbers of subsequent generations when co-cultivated with wild-type weedy species, compared to the absence of significant growth impairment for the transformed, herbicide-resistant- "shatterproof" rice strains as compared with non-TM, herbicide-resistant strains.

The hybrid dwarfs are unable to compete successfully with red-rice when grown together, thus preventing proliferation of the primary transgenic trait in the red rice population. Due to the "shatterproof" TM mitigator gene, any seed that does form on the hybrid is harvested and processed along with the cultivated rice, and does not replenish the seed bank in the field. Further, anthocyanin biosynthesis can also be transgenically suppressed (see details of RNAi, ribozyme, antisense, etc., down regulation of gene expression, herein above) in the seeds as part of the construct, using the system devised by Schweizer et al. (Plant Journal, 2000; 24: 895-903) under a seed-specific promoter. The rare hybrid seed, no longer red, would be undetectable, reducing dockage of the crop for red rice and lost revenue. Yet further, part of the second dormancy characteristic of the weedy rice species can be prevented by adding an anti-sense construct for a gene of the abscissic acid biosynthesis or signal recognition pathway, such as the AREB1-3 genes (GenBank accession No.s AB01760, AB01761, and AB01762, respectively) under the control of a seed-specific promoter, conferring impaired response to ABA in seeds, but not in vegetative tissues.

Multiple TM Traits for Tall Rice Varieties, Using the Rice GA 2-Oxidase Gene for Dwarfing:

The green revolution was predicated on reducing the height of rice by mutational breeding, increasing the harvest index. Many high quality rice varieties could not be dwarfed in this manner because their quality traits were polygenic and lost during the crossing and backcrossing with the semi-dwarf varieties. There are many primary genes (Table 4) that are advantageous in these tall varieties, and to ensure that these phenotypes are not transferred to feral or wild rice, mitigation is imperative, and should be doubly assured with these high quality tall varieties. Thus, in another embodiment of the method of the present invention, an additional group of transgenic rices is made, using biolistic co-transformation, both adding to the primary gene (Table 4), as well as adding dwarfing genes to the anti-shattering genes. The dwarfing gene construct contains the rice GA 2-oxidase (OsGA20ox1) open reading frame operably linked to the promoter of the rice OsGA3ox2 gene, which is expressed mainly in vegetative tissues. GA deactivation is restricted to the sites of synthesis within the leaves and stems, as described by Sakamoto et al. (Nature Biotechnology, 2003; 21: 909-913).

Example 5

Mitigation of Transgene Introgression in "Root" Crops (*B. vulgaris* and *D. carota*) by Tandem Constructs using the "Anti-Bolting" GA3 or AtGA2ox Gene for Preventing Precocious Flowering The various root (or enlarged hypocotyls or stem) crops such as beets, radishs, carrots and onions have a need for transgenes to provide weed free fields as they are poor competitors with weeds (needing herbicide resistance), disease resistance, virus resistance, etc., and a considerable number of primary genes have reached the point of field testing (Table 7).

TABLE 7

Examples of primary genes inserted into sugar beet and carrot for potentially commercial purposes and field tested in the USA

| Type of gene/phenotype | Gene | APHIS #[a] |
|---|---|---|
| A. Sugar Beet Herbicide Resistance | | |
| Glyphosate | CBI | 03-205-10 |
| Glyphosate | EPSPs (Agro) | 01-341-06 |
| Protoporphyrinogen oxidase | CBI | 01-341-03 |
| Glyphosate R | EPSP synthase | 01-046-23 |
| Glufosinate | Strep.phosphinothricin acetyl transferase | 00-214-02 |
| Glyphosate resistance | EPSP synthase + glyphosate oxireductase | 96-057-03 |
| Virus resistance | | |
| BNYVV resistance | CBD | 03-092-01 |
| BNYVV | coat protein | 98-065-18 |
| CBI | CBI | 97-044-02 |
| B. carrot Herbicide Resistance | | |
| Glyphosate | CBI | 00-075-11 |
| Nematode Resistance | | |
| Root knot nematode R | Cowpea cystein proteinase | 00-073-07 |
| Disease Resistance | | |
| Alternaria dauci | CBI | 99-277-01 |
| | Tobacco chitinase, glucanases and osmitin, petunia osmitin | 95-019-01 |
| Nutritional quality altered | CBI | 93-340-01 |

[a]Examples from 155 APHIS requests

The problem is that introgression of such desirable primary transgenes might offer a fitness advantage to related weeds that interbreed with them. Carrots and the annual weed Queens Anne's Lace are the same species, and radish and beets have very closely related members of the same and related genera that readily interbreed in the field.

For example, weed beets, most often of the sea beet (*B. vulgaris* ssp. *maritima*) pose a serious problem for sugar beet *Beta vulgaris* crops and traditionally, the only efficient method of weed control has been manual removal. The introduction of transgenic herbicide-resistant sugar beets provides an alternative solution because non-tolerant weed beets can be destroyed by herbicide. Desplanque et al., (J. Appl. Ecol., 2002; 39: 561-571) and Arnaud et al (Proc. R. Soc. Lond. 2003;270:1565-71) recently evaluated the possibility that new, transgenic, weed beets may arise by gene flow between wild and crop plants. Weed beets arise from a long-lived seed bank. Crop-wild hybrids and triploid variety bolters (individuals with a low vernalization requirement) were present in low densities in virtually all sugar beet fields. They found gene flow to be possible between all forms, illustrated by both overlapping flowering periods in the field and successful controlled cross-pollinations. The F-1 crop-wild hybrids result from pollination in the seed-production region by wild plants possessing the dominant bolting allele B for flowering without experiencing a period of cold, and hybrids with transgenes for herbicide tolerance incorporated will bolt. The appearance of transgenic weed beets is possible but they suggest it can at best be retarded if the transgene for herbicide tolerance is incorporated into the tetraploid pollinator breeding line. Thus, the best containment procedure proposed is leaky.

The transgenic prevention of bolting of the crop in crop production fields would prevent the appearance of flowers, a prerequisite for sexual hybridization. Even if not absolute, the rare individual forming a hybrid would not usually flower in the first year, and the weedy annual relatives of these root crops must flower to produce seed. Thus, a plant carrying an anti-bolting gene will always be at a selective disadvantage. Bolting of the root crops during the season can cause considerable loss of yield, so an anti-bolting gene would have a positive effect on the crop.

Transformation of Root Crops with Anti-Bolting TM Constructs

In order to confer "anti-bolting" characteristics, an ent-kaurene oxidase GA3 gene sequence, in an RNAi or anti-sense orientation (GA3 is a key gene in the gibberellic acid biosynthesis pathway, and a key gene expressed when bolting is initiated by gibberellins-see Helliwell et al., PNAS USA 1999; 95:9019-24), such as GenBank Accession Nos. NM122491, from Arabidopsis and AY462247, from Fragaria, is operatively linked in tandem with a herbicide resistance gene such as glyphosate resistance as primary gene of interest (alternatively, other primary genes described in Table 5 can be used as primary transgenes) and transformed via *Agrobacterium* (as described in detail in Examples 1 and 2) into sugar beets (*B. vulgaris*), radish (*R. sativus*) and carrots (*D. carota*), and the plants regenerated and tested for the presence and expression of the construct by PCR and partial sequencing. Stable transformants are selected by herbicide resistance, ent-kaurene oxidase enzyme assay, and GA assay, and propagated. Also, additional TM constructs are prepared comprising a primary transgene of interest, for example, herbicide resistance, operatively linked in tandem to an expressible coding sequence of GA oxygenase degradation enzymes (Schomburg et al Plant Cell Rev 2003;15:151-63) such as GenBank Accession Nos. NM106491 and NM129007 from *Arabidopsis*, AJ315663 from cucumber, AY242858 from tobacco, and BG59238 from potato, plants regenerated, tested, selected and propagated as described above.

The competitive disadvantage of the transgenic cultivated-weedy species hybrid can be observed by comparing the growth of such hybrids alone, co-cultivated along with the transgenic cultivated crop, and in competition with the wild-type weedy species. Sea beets are transformed with the herbicide-resistant-anti-bolting construct described above, to simulate introgression. Following selection and propagation as described above, the hybrid progeny is grown alone, and co-cultivated along with either wild-type sea beet, or transformed, herbicide-resistant- "anti-bolting" sugar beets, as described for tobacco and oilseed rape in Examples 1 and 2 herein above. Mitigation of introgression of the primary transgene (herbicide resistance) in the weedy species is demonstrated by the failure of the hybrid progeny to transmit herbicide resistance to significant numbers of subsequent generations when co-cultivated with wild-type weedy species, compared to the absence of significant growth impairment for the transformed, herbicide-resistant- "anti-bolting" sugar beets as compared with non-TM, herbicide-resistant strains.

Seeds are obtained on the resulting transgenic crop containing "anti-bolting" mitigator genes by treating mature plants with gibberellic acid, both in the initial regeneration and in field production for seeds. Reversal of inhibition of flowering in plants by application of gibberellic acid is well known in the art, for example, as described in U.S. Pat. No. 5,006,154 to Kaplan et al., incorporated herein by reference. Should one of the wild relatives be present and hybridize in these seed production areas, bolting (flowering) of the rare hybrid outcrossed progeny will not occur due to the presence of the TM transgene, thus eliminating further transmission, and thus introgression of the primary transgene into wild-type, weedy beet species.

Example 6

Mitigation of Transgene Introgression in Trees by Tandem Constructs using Tapetum-Specific Expression of a Barnase "Sterility" Gene Transgenic, vegetatively propagated poplar, pine, and eucalypts bearing traits for pest and herbicide resistance (Gressel 2002 Molecular Biology of Weed Control—Taylor & Francis, London) and especially decreased or modified lignin, are being tested prior to commercialization (Table 8).

TABLE 8

Examples of commercially important primary genes inserted into Populus spp (poplars, aspens, cottonwoods) being field tested in the USA

| Type of gene/phenotype | gene(s) | APHIS # |
|---|---|---|
| Herbicide resistance | | |
| CBI | CBI | 03-008-04 |
| Glyphosate | CBI | 00-073-07 |

TABLE 8-continued

Examples of commercially important primary genes inserted into Populus spp (poplars, aspens, cottonwoods) being field tested in the USA

| Type of gene/phenotype | gene(s) | APHIS # |
|---|---|---|
| Glyphosate + Glufosinate | EPSP synthase/phosphinothricin acetyltransferase | 95-031-01 |
| Glyphosate | EPSP synthase + glyphosate oxyreductase | 96-026-02 |
| *Insect resistance* | | |
| Coleopteran | CBI | 02-094-04 |
|  | Bt Cry IIIA | 98-149-11 |
| Phratora and cottonwood leaf beetle | Bt CryIIIA | 97-175-02 |
| Lepidopteran | Bt CryIA(c) | 93-039-02 |
| *Disease Resistance (Fungal)* | | |
| *Septoria* | wheat antimicrobial peptide + *E. coli* oxalate oxidase | 00-131-03 |
| *Septoria/Venturia/Melamtsora/ Marssonina* | *Halobacterium* bacteropsin | 98-013-02 |
| *Disease Resistance (Bacterial)* | | |
| Crown gall | *Agrobacterium* IAA monooxygenase | 98-128-25 |
| *Improved pulping quality* | | |
| Modified lignin content | poplar caffeateO methyl transferase + poplar 4 coumarate CoA ligase | 03-247-08 |
|  | poplar 4 coumarate CoA ligase | 00-329-06 |
|  | aspen 4 coumarate CoA ligase | 98-128-20 |
|  | aspen cinnamate 4 hydrolase + aspen caffeate o methyltransferase + aspen 4 coumarate: CoA ligase + aspen 0-methyltransferase | 98-077-02 |
| Modified cellulose | *Clostridium* cellulose binding protein | 98-086-02 |
| *Bioremediation* | | |
| CBI | CBI | 03-099-10 |
| Mercury removal | mercuric ion reductase + organomercurylyase | 03-044-01 |
|  | mercuric ion reductase | 01-218-04 |
| Halogenated hydrocarbons | human cytochrome P450 | 99-295-11 |

Condensed from 85 APHIS records

Reduced or modified lignin considerably decreases the cost of paper production by reducing the amounts of chemical required for delignification. This in turn reduces environmental impact of chemical wastes. These trees are typically vegetatively propagated for planting (vegetative propagation of trees is well known in the art. See, for example, Mehra-Palta, et al, U.S. Pat. No. 4,550,528, incorporated herein by reference). There is concern that pollen from such trees will pollinate native relatives, giving rise to hybrid offspring having the genetically modified traits. This is not of great concern with primary transgenic traits such as herbicide resistance, but pest resistances or wood characters can change the delicate ecological balance within forests.

Thus, proposed strategies for containment of desirable transgenic traits have been based on the use of lines of trees having male sterility (natural or transgenic), and plastid transformation. Since male sterility is not absolute, and some viable pollen may escape, there remains the concern that only 50% of pollen bearing the primary trait will bear the male sterility trait, as a result of chromosome segregation.

As described earlier, plastid transformation is also not an absolutely fail safe containment method. In dicots some pollen contains plastid DNA (and plastid-borne traits), and in pine all pollen carries the entire plastid genome. Thus, neither containment strategy described (male sterility or plastid transformation) above precludes pollen inflow into a transgenic tree plantation, formation of hybrids, and subsequent dispersal of progeny.

Conversely, transgenic mitigation, wherein the mitigator transgene is covalently linked to the primary gene in a TM construct, assures that all rare hybrid offspring bear the mitigator trait, and thus provides an otherwise unattainable solution to the significant disadvantages of containment strategies.

Transformation of Trees with TM Constructs.

In order to confer the male sterility phenotype, a cytotoxic element, such as the barnase gene from *B. amyloliquefaciens* (for example, GenBank Accession Nos. X15545, M14442, X12871) (for constructs, methods of transformation and expression of *barnase* see, for example, WO 89/10396; U.S. Pat. No. 6,372,960, to Michiels et al; and Custers et al., 1997, all incorporated herein by reference), under control of a tapetum specific promoter such as the TA29 sequence from tobacco or the taz promoter from petunia, is operatively linked in tandem with a lignin modifying gene such as poplar 4 coumarate CoA ligase as primary gene of interest (alternatively, other primary genes described in Table 6 can be used as primary transgenes), along with a selectable marker such as kanamycin (suitable selectable marker genes are well known in the art and include, but are not limited to, genes encoding resistance to kanamycin [neomycin phosphotransferase (npt) II (Fraley et al. (1986) CRC Critical Reviews in Plant Science 4:1-25)], ampicillin/carbenicillin, streptomycin/spectinomycin, gentamycin, and tetracycline). The resulting constructs are transformed via *Agrobacterium* (as described in detail in Examples 1 and 2) into trees such as poplar and cottonwood (*Populus*),pine (*Pinus*), and eucalypts (gum tree) (*Eucalyp-*

*tus*). The resulting seedlings are regenerated and tested for presence and expression of the construct by PCR and partial sequencing. Stable transformants are selected by, for example, kanamycin resistance, poplar 4 coumarate CoA ligase enzyme assay, tapetum specific cytotoxicity and/or male sterility, and propagated.

The competitive disadvantage of the transgenic cultivated-wild species hybrid can be observed by comparing the growth of such hybrids alone, co-cultivated along with the transgenic cultivated crop, and in competition with the wild-type species. Non-transgenic poplars (or other tree species mentioned herein above) were transformed with the lignin-modifying-barnase construct described above, to simulate introgression. Following selection and propagation as described above, the hybrid progeny is grown alone, tapetum-specific expression of the *barnase* gene confirmed by PCR and partial sequencing, and male sterility confirmed by morphological and functional assay of anther tissue from the hybrid plants. Mitigation of introgression of the primary transgene (lignin modification) into the wild type species is demonstrated by the failure of the hybrid progeny to produce viable progeny. In contrast with the some of the methods taught for sexually propagated species, there is no need for the barstar restoration system, as the transgenic trees are vegetatively (asexually) propagated.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety. Citation or identification of any reference in this application shall not be construed as an admission that such reference is available as prior art to the present invention.

REFERENCES

1. Al-Kaff, N. S., S. N. Covey, M. M. Kreike, A. M. Page, R. Pinder and P. J. Dale. , 1998. Transcriptional and postranslational plant gene silencing in response to a pathogen. Science 279:2113-2115.
2. Anon., 1994a. Assessment criteria for determining environmental safety of plants with novel traits. Directive Dir. 94-08 Plant Products Division, Agriculture and Agri-Food Canada, Nepean Ontario. (http://www.cfia-acia.agr.ca/English/food/pbo/dir9408.html).
3. Anon., 1994b. The biology of *Brassica napus* L (canola/rapeseed). Directive Dir. 94-09 Plant Products Division, Agriculture and Agri-Food Canada, Nepean Ontario. (http://www.cfia-acia. agr. ca/English/food/pbo/dir9409.html).
4. Anon., 1997 Consensus document on the biology of *Brassica napus* L. (oilseed rape). Series on the harmonization of regulatory oversight in biotechnology No. 7. Environ. Directorate. Org. for Econ. Co-op. and Devel., Paris.
5. Arias, D. M. and L. H. Riesenberg., 1994. Gene flow between cultivated and wild sunflowers. Theor. Appl. Genet. 89:655-660.
6. Aukerman, M. J., M. Hirschfeld, L. Wester, M. Weaver, T. Clack, R. M. Amasino and R. A. Sharrock., 1997. A deletion in the PHYD gene of the *Arabidopsis* Wassilewskija ecotype defines a role for phytochrome D in red/far-red light sensing. Plant Cell 9:13 17-1326.
7. Azpiroz, R., Y. Wu, J. C. LoCascio and K. A. Feldmann., 1998. An *Arabidopsis* brassinosteroid-dependent mutant is blocked in cell elongation. Plant Cell 10: 219-230.
8. Baker, H. G., 1974. The evolution of weeds. Aim. Rev. Ecol. Sys. 5:1-24.
9. Baker, H. G., 1991. The continuing evolution of weeds. Econ. Bot. 45:445-449.
10. Barrett, S. C. H., 1983. Crop mimicry in weeds. Econ. Bot. 37:255-282.
11. Be, D. B., S. G. Rogers, T. B. Stone, and F. S. Serdy. , 1996. Herbicide tolerant plants developed through biotechnology: Regulatory considerations in the United States. p. 34 1-346. In: S. O. Duke (ed.), Herbicide resistant crops: Agricultural, environmental, economic, regulatory, and technical aspects. CRC Press, Boca Raton.
12. Bergelson, J., C. B. Purrington, C. J. Palm, and J. C. Lopez-Guitierrez., 1996. Costs of resistance —a test using transgenic *Arabidopsis thaliana*. Proc. Roy. Soc. Lond. B. Biol. Sci. 262: 1659-1663.
13. Bewley, J. D., 1997. Breaking down the walls —a role for endo-beta-maimanase in release from seed dormancy? Trends Plant Sci. 2: 464-469.
14. Bing, D. B., R. K. Downey, and G. F. W. Rakow. , 1996 Assessment of transgene escape from *Brassica rapa* (B. *campestris*) into B. *nigra* or *Sinapis arvensis*. Plant Breed. 115:1-4.
15. Boudry, P., M. Mirchen, P. Saumitou-Laprade, H, Vemet, and H. Van Dijk., 1993. The origin and evolution of weed beets: consequences for the breeding and release of herbicide-resistant transgenic sugar beets. Theor. Appl. Genet. 87:471-478.
16. Brown, J., and A. P. Brown., 1996. Gene transfer between canola (*Brassica napus* L. and B. *campestris* L.) and related weed species. Ann. Appi. Biol. 129:513-522.
17. Choe, S. B. P. Dilkes, S. Fugioka, S. Takatsuto, A. Sukarai, and K. A. Felmann. , 1998. The DWF4 gene of *Arabidopsis* encodes a cytochrome P450 that mediates multiple 22 α-hydroxylation steps in brassinosteroid biosynthesis. Plant Cell 10:231-144.
18. Conner, A. J., and P. J. Dale., 1996. Reconsideration of pollen dispersal data from field trials of transgenic potatoes. Theor. Appl. Genet. 92:505-508.
19. Cooper, J. L. and A. F. Raybould. , 1997. Transgenes for stress tolerance: consequences for weed evolution. Brighton Crop Protect. Conf.-Weeds. pp. 265-272.
20. Crawford, J., G. Squire, and D. Bum., 1997. Modeling spread of herbicide resistant oilseed rape. In: A. J. Gray, C. Glidden and F. Amjee (eds.). Environmental Impact of Genetically Modified Crops. Dept. of Environment, London, (in press).
21. Crawley, M. J., R. S. Hails, M. Rees, D. Kohn, and J. Buxton. , 1993. Ecology of transgenic oilseed rape in natural habitats. Nature 363:620-623.
22. Darmency, H., 1994. The impact of hybrids between genetically modified crop plants and their related species: introgression and weediness. Mol. Ecol. 3:37-40.
23. DeKathen, A., 1998. The debate on risks from plant biotechnology: the end of reductionism? Plant Tissue Culture and Biotechnology 4: 136-148.
24. Devlin, P. F., S. R. Patel and G. C. Whitelam., 1998. Phytochrome E influences internode elongation and flowering time in *Arabidopsis*. Plant Cell 10:1479-1488.
25. Diepenbrock, W. and J. Leon. , 1988. Quantitative effects of volunteer plants on glucosinolate content in double-low rapeseed (*Brassica napus* L.): a theoretical approach. Agronomie 8:373-377.
26. Eijlander, R., and W. J. Stiekema., 1994. Biological containment of potato (*Solanum tuberosum*): outcrossing to the related wild species black nightshade (*Solanum nigrum*) and bittersweet (*Solanum dulcamara*). Sex Plant Reprod. 7: 29-40.

27. Foley, M. E., and S. A. Fennemore. , 1998. Genetic basis for seed dormancy. Seed Sci. Res. 8:173-182.

28. Galun, E. and A. Breiman. , 1997. Transgenic Plants. Imperial College Press, London, 376 pp.

29. Goldburg, R., J. Rissler, H, Shand, and C. Hassebrook. , 1990. Biotechnology's bitter harvest. Environmental Defense Fund, New-York.

30. Gould, F., 1991. The evolutionary potential of crop pests. Amer. Sci. 79: 496-507.

31. Gressel, J., 1997. Genetic engineering can either exacerbate or alleviate herbicide resistance. Proc. 50th New Zealand Plant Protection Conf. p. 298-306.

32. Gressel, J., and A. W. Rotteveel. , 2000. Risks from Biotechnologically-Derived Herbicide-Resistant Crops: Decision Trees for Assessment. Plant Breeding Rev., 18:251-303.

33. Haas, H., and J. C. Streibig., 1982. Changes in weed distribution patterns as a result of herbicide use and other agronomic factors. p. 57-80. In: H. M. LeBaron and J. Gressel (eds.), Herbicide resistance in plants. Wiley, New-York.

34. Hedden, P., 1997. The oxidases of gibberellin biosynthesis: Their function and mechanism. Physiol. Plant. 101: 709-719.

35. Hedden, P., and Y. Kamiya. , 1997. Gibberellin biosynthesis: Enzymes, genes and their regulation. Ann. Rev. Plant Physiol. Plant Mol. Biol. 48: 431-460.

36. Helliwell, C. A., C. C. Sheldon, M. R. Olive, A. R. Walker, J. A. D. Zeevaart, W. J. Peacock and E. S. Dennis., 1998. Cloning of the *Arabidopsis* ent-kaurene oxidase gene GA3. Proc. Natl. Acad. Sci. U.S.A. 95:9019-9024.

37. Holm, L., J. Doll, B. Holm, J. Pancho, and J. Herberger. , 1997. Worlds weeds: Natural histories and distributions. Wiley, New York.

38. Holt, J. S., 1988. Ecological and physiological characteristics of weeds. P. 7-23. In: M. A. Altieri and M. Liebman (eds.), Weed Management in Agroecosystems: Ecological Approaches. CRC Press, Inc. Boca Raton, Fla.

39. Hyatt, L. A., and A. S. Evans. , 1998. Is decreased germination fraction associated with risk of sibling competition? OIKOS. 83: 29-35

40. Jorgensen, R. B., and B. Andersen. , 1994. Spontaneous hybridization between oilseed rape (*Brassica napus*) and weedy B. *campestris*: a risk of growing genmodified oilseed rape. Am. J. Bot. 81: 1620-1626.

41. Kareiva, P., I. M. Parker, and M. Pascual. , 1996. Can we use experiments and models in predicting the invasiveness of genetically engineered organisms? Ecology 77:1670-1675.

42. Keeler, K. H., C. E. Turner, and M. R. Bollick. , 1996. Movement of crop transgenes into wild plants. p. 303-330 In: S. O. . Duke (ed.), Herbicide resistant crops: Agricultural, environmental, economic, regulatory, and technical aspects. CRC Press, Boca Raton.

43. Kerlan, M. C., A. M. Chevre, and F. Eber, F., 1993. Interspecific hybrids between a transgenic rapeseed (*Brassica napus*) and related species: cytogenetical characterization and detection of the transgene. Genome 36:1099-1106.

44. Khan, A. A. , 1997. Quantification of seed dormancy: Physiological and molecular considerations. Hortsci. 32: 609-614.

45. Kimber, G., and E. R. Sears., 1987. Evolution of the genus *Triticum* and the origin of cultivated wheat. In: E. G. Heyne (ed.), Wheat and wheat improvement. Agronomy Monograph No. 13. ASA-SCCA-SSSA, Madison Wis., pages. 154-164.

46. Kjellsson, G., V. Simonsen, and K. Ammann, (eds.)., 1994. Methods for risk assessment of transgenic plants. Vol. 2. Pollination, gene transfer and population impacts. Birkhaeuser, Basel.

47. Kling, J., 1996. Could transgenic supercrops one day breed superweeds? Science 274:180-181.

48. Kloppenburg, J., Jr. , 1988. First the seeds: The political economy of plant biotechnology, Cambridge Univ. Press, Cambridge.

49. Koltunow, A .M., R. A. Bicknell, and A. M. Chaudhury., 1995. Apomixis: Molecular strategies for the generation of genetically-identical seeds without fertilization. Plant Physiol. 108:1345-1352.

50. Krimsky, S., and R. Wrubel. , 1996. Agricultural biotechnology: Science, policy, and social issues. Univ. Ill. Press, Urbana.

51. Kusaba, S., M. Fukumoto, C. Honda, I. Yamaguchi, T. Sakamoto, and Y. Kano-Murakami. , 1998. Decreased GA(1) content caused by the overexpression. of OSH1 is accompanied by suppression of $GA_{20}$ and oxidase gene expression. Plant Physiol. 117:1179-1184.

52. Landbo, L., 13. Andersen, and R. B. Jorgensen., 1996. Natural hybridization between oilseed rape and a wild relative: hybrids among seeds from weedy *B. campestris*. Hereditas 125:89-91.

53. Lange, T. , 1998. Molecular biology of gibberellin synthesis. Planta 204:409-419.

54. Lange, T., S. Robatzek, and A. Frisse. , 1997. Cloning and expression of gibberellin 2β,3β-hydroxylas cDNA from pumpkin endosperm. Plant Cell 9:1459-1467.

55. Lefol, E., V. Danielou, and H. Darmency., 1996a. Predicting hybridization between transgenic oilseed rape and wild mustard. Field Crops Res. 45: 153-161.

56. Lefol, E., A. Fleury, and H. Darmency. , 1996b. Gene dispersal from transgenic crops II. Hybridization between oilseed rape and the wild hoary mustard. Sex. Plant Reprod. 9:189-196.

57. Levy, A., 1985. A shattering-resistant mutant of *Papaver bracteatum* Lindl: characterization and inheritance. Euphytica 34: 811-815.

58. Li, B. L., and M. E. Foley. , 1997. Genetic and molecular control of seed dormancy. Trends Plant Sci. 2:384-389.

59. Lin, S. Y., T. Sasaki, M. Yano. , 1998. Mapping quantitative trait loci controlling seed dormancy and heading date in rice, *Oryza sativa*L., using backcross inbred lines. Theor. Appi. Genet. 96:997-1003.

60. Lincoln, J. and Fischer, R., 1988. Diverse mechanisms for the regulation of ethylene-inducible gene expression. Mol. Gen. Genet. 212:71-75.

61. Linder, C. R., 1998. Potential persistence of transgenes: seed performance of transgenic canola and wild X canola hybrids. Ecol. Appli. 8:1180-1195.

62. Ling-Hwa, T., and H. Morishima, 1997. Genetic characterization of weedy rices and the inference on their origins. Breeding Sci. 47:153-160

63. Love, S. L. , 1994. Ecological risk of growing transgenic potatoes in the United States and Canada. Amer. Potato J. 71:647-658.

64. Lundberg, S., P. Nilsson, and T. Fagerstrom., 1996. Seed dormancy and frequency dependent selection due to sib competition: The effect of age specific gene expression. J. Theor. Biol. 183:9-17.
65. Lutman, P. J. W., 1993. The occurrence and persistence of volunteer rapeseed (*Brassica napus*). Asp. Appl. Biol. 35:29-36.
66. Metz, P. L. J., E. Jacobsen, J. P. Nap, A. Pereira, and W. J. Steikema., 1997. The impact of biosafety on the phosphinothricin-tolerance transgene in interspecific *B. rapa* x *B. napus* hybrids and their successive backcrosses. Theor. Appl. Gen. 95 :442-450.
67. Mikkelsen, T. R., J. Jensen, and R. B. Jorgensen., 1996. Inheritance of oilseed rape (*Brassica napus*) RAPD markers in a backcross with progeny with *Brassica campestris*. Theor. Appi. Genet. 92:492-497.
68. Nishijima, I., N. Katsura, M. Koshioka, H. Yamazaki, M. Nakayama, H. Yamane, I. Yamaguchi, T. Yokota, N. Murofushi, N. Takahashi, and M. Nonaka., 1998. Effects of gibberellins and gibberellin-biosynthesis inhibitors on stem elongation and flowering of *Raphanus sativus* L. J. Jap. Soc. Hort. Sci. 67:325-330.
69. Pantone, D. J., and J. B. Baker. , 1991. Weed-crop competition models and response-surface analysis of red rice competition in cultivated rice: A review. Crop Sci. 31:1105-1110.
70. Paterson, A. H., K. F. Schertz, Y-R. Lin, S-C. Liu and Y-L. Chang., 1995. The weediness of wild plants: Molecular analysis of genes influencing dispersal and persistence of johnsongrass, *Sorghum halepense* (L.) Pers. Proc. Natl. Acad. Sci. U.S.A. 92: 6127-6131.
71. Powell, M. , 1997 Science in sanitary and phytosanitary dispute resolution. Discussion Paper 97-50, Resources for the Future, Washington, D.C.
72. Prakash, S. , 1988. Introgression of resistance to shattering in *Brassica napus* from *Brassica juncea* through non-homologous recombination. Z. Pflanzenzuch. 101:167-168.
73. Price, J. S, R. N. Hobson, M. A. Nealle, and D. M. Bruce., 1996. Seed losses in commercial harvesting of oilseed rape. J. Agr. Engineer. Res. 65:183-191.
74. Regal, P. J., 1994. Scientific principles for ecologically based risk assessment of transgenic organisms. Molec. Ecol. 3:5-13.
75. Rissler, J. and M. Mellon., 1993. Perils amidst the promise—ecological risks of BD-HRCs in a global market. Union of Concerned Scientists, Cambridge Mass.
76. Robson, P. R. H., A. C. McCormac, A. S. Irvine, and H. Smith. , 1996. Genetic engineering of harvest index in tobacco through overexpression of a phytochrome gene. Nature Biotech. 14:995-998.
77. Schaller, H., P. Bouvier-Naveo and P. Benveniste., 1998. Overexpression of an *Arabidopsis* cDNA encoding a sterol-C24-methyltransferase in tobacco modifies the ratio of 24-methyl cholesterol to sitosterol and is associated with growth reduction. Plant Physiol. 118:461-469.
78. Scheffler, J. A., R. Parkinson, and P. J. Dale., 1995. Evaluating the effectiveness of isolation distances for field plots of oilseed rape (*Brassica napus*) using a herbicide resistant transgene as a selectable marker. Plant Breed. 114: 317-321.
79. Simon, U., 1994. "Alko" the first seed-shattering resistant cultivar of meadow foxtail *Alopecurus pratensis* L. Acta Hort. .355: 143-146.
80. Sindel, B.M., 1997. Outcrossing of transgenes to weedy relatives. p. 43-81. In: G. D. McLean, P. M. Waterhouse G. Evans and M. J. Gibbs (eds.), Commercialisation of BD-HRCs: Risk, benefit and trade considerations. Coop. Res. Center for Plant Sci. and Bur. of Resource Sci., Canberra.
81. Smith, H., and G. C. Whitelam., 1997. The shade avoidance syndrome: Multiple responses mediated by multiple phytochromes. Plant Cell Environ. 20: 840-844.
82. Smith, M. W., S. Yamaguchi, I. Ait-Ali, and Y. Kamiya., 1998. The first step of gibberellin biosynthesis in pumpkin is catalyzed by at least two copalyl diphosphate synthases encoded by differentially regulated genes. Plant Physiol. 118: 1411-1419.
83. Snow, A. A., P. Moran-Palma, L. H. Rieseberg, A. Wszelaki, and G. J. Seiler., 1998. Fecundity, phenology, and seed dormancy of $F_1$ wild-crop hybrids in sunflower (*Helianthus annuus*, Asteraceae). Amer. Jour. Bot. 85:794-801
84. Steber, C. M., S. E. Cooney, P. McCourt, , 1998. Isolation of the GA-response mutant sly1 as a suppressor of ABII-1 in *Arabidopsis thaliana*. Genetics 149:509-521
85. Thill, D. C., and C. A. Mallory-Smith., 1997. The nature and consequence of weed spread in cropping systems. Weed. Sci. 45:337-342.
86. Timmons, A. M., Y. M. Charters, J. W. Crawford, D. Burn, S. E. Scoff, S. J. Dubbels, N. J. Wilson, A. Robertson, E. T. O'Brien, G. R. Squire and M. J. Wilkinson. 1. Risks from BD-HRCs. Nature 380: 487.
87. Torgersen, H., 1996. Risk assessment in transgenic plants: what can we learn from the ecological impacts of traditional crops? BINAS News 2: (3 &4) (http://www.binas.unido.org/binas/News/96 issue34/risk.html)
88. Torii, K. U., T. W. McNellis, and X.-W. Deng., 1998. Functional dissection of *Arabidopsis* COP1 reveals specific roles of its three structural modules in light control of seedling development. EMBO J. 17:5577-5587.
89. Turner, C.E., 1988. Ecology of invasions by weeds. Weed Management in Agroecosystems: Ecological Approaches. pp. 41-54. In: M. A. Altieri and M. Liebman (eds.), Weed Management in Agroecosystems: Ecological Approaches. CRC Press, Inc. Boca Raton, Fla.
90. N. , 1935. Genome analysis in *Brassica* with special reference to the experimental formation of *B. napus* and the peculiar mode of fertilization. Japan. J. Bot. 7: 389-452.
91. Van der Schaar, W., C. L. A. Blanco, K. M. Kloosterziel, R. C. Jansen, J. W. Van Ooijen, and M. Koornneef. , 1997. QTL analysis of seed dormancy in *Arabidopsis* using recombinant inbred lines and MQM mapping. Heredity 79: 190-200.
92. Vleeshouwers, L. M. , 1988. The effect of seed dormancy on percentage and rate of germination in *Polygonum persicaria*, and its relevance for crop-weed interaction. Ann. Appi. Biol. 132:289-299.
93. Wan, J., T. Nakazaki, K. Kawaura, and H. Ikehashi., 1997. Identification of marker loci for seed dormancy in rice (*Oryza sativa* L.) Crop Sci. 37: 1759-1763.
94. Waters, S. , 1996. The regulation of herbicide-resistant crops in Europe. p. 347-362. In: S. O. Duke (ed.), Herbicide resistant crops: Agricultural, environmental, economic, regulatory, and technical aspects. CRC Press, Boca Raton.
95. Webb, S. E., N. E. J. Appleford, P. Gaskin, and J. R. Lenton., 1998. Gibberellins in internodes and ears of wheat containing different dwarfing alleles Phytochemistry 47:671-677.

96. White, A. D., M. K. E. Owen, and R. G. Hartzler. , 1998. Evaluation of common sunflower (*Helianthus annuus* L.) resistance to acetolactate synthase inhibiting herbicides. Weed Sci. Soc. Am. Abstr. 38:1120.
97. Whitton, J., D. E. Wolf, D. M. Arias, A. A. Snow, and L. H. Reiseberg., 1995. The persistence of cultivar alleles in wild populations of sunflowers five generations after hybridization. Theor. Appl. Genet. 95:35-40
98. Williams, M. E. , 1995. Genetic engineering for pollen control. Trends Biotech. (TIBTECH) 13:344-349.
99. Williamson, M., 1993. Invaders, weeds, and risks from genetically manipulated organisms. Experientia 49:219-224.
100. Yamaguchi, S., T. P. Sun, H. Kawaide, and Y. Kamiya., 1998. The $GA_2$ locus of *Arabidopsis thaliana* encodes ent-kaurene synthase of gibberellin biosynthesis. Plant Physiol. 116:1271-1278.
101. Young, B. A., 1991. Heritability of resistance to seed shattering in kleingrass., 1991. Crop Sci. 31:1156-1158.
102. Zemetra, R. S., J. Hansen, and C. A. Mallory-Smith. , 1998. Potential for gene transfer between wheat (*Triticum aestivum*) and jointed goatgrass (*Aegilops cylindrical*). Weed Sci. 46: 313-317.

What is claimed is:

1. A method to provide a mitigation to effects of introgression of at least one advantageous genetically engineered trait to an uncultivated interbreeding species related to the transformed cultivated crop, the method comprising transforming a population of plants of the cultivated crop to co-express the at least one advantageous genetically engineered trait, and at least one mitigating genetic trait, wherein:
   said at least one advantageous genetic trait is encoded by an advantageous gene conferring a trait selected from the group consisting of herbicide resistance, disease, insect and nematode resistance, environmental stress resistance, high productivity, modified agronomic quality, enhanced yield, modified ripening, bioremediation, expression of heterologous products and genetically modified plant products;
   said at least one mitigating genetic trait is encoded by a mitigating gene, said mitigating gene being an anti-shattering gene, an anti-bolting gene or a dwarfism gene;
   said advantageous gene and said mitigating gene having a genetic distance of no greater than 10 centimorgans from each other so as to produce tandem introgression of said advantageous and said mitigating traits into said uncultivated interbreeding species; and
   wherein introgression and expression of said mitigating genetic trait in said uncultivated interbreeding species related to the cultivated crop renders said uncultivated interbreeding species less fit compared to a similar uncultivated interbreeding species related to the cultivated crop and not expressing said mitigating genetic trait.

2. The method of claim 1, wherein said at least one mitigating genetic trait is an endogenous genetic trait of said cultivated crop.

3. The method of claim 1, wherein said cultivated crop is tobacco, rice or oilseed rape, said advantageous genetic trait is herbicide resistance, and said mitigating genetic trait is gibberellic acid insensitivity.

4. The method of claim 1, wherein said cultivated crop is sugarbeet, said advantageous genetic trait is herbicide resistance, and said mitigating genetic trait is antibolting.

5. The method of claim 1, wherein said advantageous genetic trait is herbicide resistance, and said mitigating genetic trait is anti-seed shattering.

6. The method of claim 5, wherein said cultivated crop is selected from the group consisting of tobacco, rice and oilseed rape.

7. The method of claim 1, wherein said cultivated crop is selected from the group consisting of tobacco, rice and oilseed rape.

8. The method of claim 1, wherein said herbicide resistance is conferred by a $ahas^R$ (acetohydroxy acid synthase) gene.

9. The method of claim 1, wherein said dwarfism gene is a Δgai (gibberellic acid-insensitive) mutant gene and said anti-shattering gene is a shatterproof gene.

10. A method to provide a mitigation to effects of introgression of an advantageous genetically engineered trait to an uncultivated interbreeding species related to the transformed cultivated crop, the method comprising transforming a population of plants of the cultivated crop to co-express the advantageous genetically engineered trait, and a mitigating genetic trait, wherein:
    said advantageous genetic trait is encoded by an advantageous gene encoding a protein conferring herbicide resistance;
    said mitigating genetic trait is encoded by an anti-shattering gene;
    said advantageous gene and said anti-shattering gene having a genetic distance of no greater than 10 centimorgans from each other so as to produce tandem introgression of said advantageous and said mitigating traits into said uncultivated interbreeding species; and
    wherein introgression and expression of said mitigating genetic trait in said uncultivated interbreeding species related to the cultivated crop renders said uncultivated interbreeding species less fit compared to a similar uncultivated interbreeding species related to the cultivated crop and not expressing said mitigating genetic trait.

11. The method according to claim 1, wherein sequences of the advantageous gene and the mitigating gene are juxtaposed.

* * * * *